US009896490B2

(12) United States Patent
Neufeld et al.

(10) Patent No.: US 9,896,490 B2
(45) Date of Patent: Feb. 20, 2018

(54) SEMAPHORIN 3C VARIANTS, COMPOSITIONS COMPRISING SAID VARIANTS AND METHODS OF USE THEREOF

(71) Applicant: RAPPAPORT FAMILY INSTITUTE FOR RESEARCH IN THE MEDICAL SCIENCES, Haifa (IL)

(72) Inventors: Gera Neufeld, Haifa (IL); Yelena Mumblat, Haifa (IL); Ofra Kessler, Haifa (IL)

(73) Assignee: RAPPAPORT FAMILY NSTITUTE FOR RESEARCH IN THE MEDICAL SCIENCES, Haifa (IL)

( * ) Notice: Subject to any disclaimer, the term of this patent is extended or adjusted under 35 U.S.C. 154(b) by 71 days.

(21) Appl. No.: 14/917,152

(22) PCT Filed: Sep. 7, 2014

(86) PCT No.: PCT/IL2014/050797
§ 371 (c)(1),
(2) Date: Mar. 7, 2016

(87) PCT Pub. No.: WO2015/033345
PCT Pub. Date: Mar. 12, 2015

(65) Prior Publication Data
US 2016/0311873 A1    Oct. 27, 2016

Related U.S. Application Data

(60) Provisional application No. 61/875,060, filed on Sep. 8, 2013.

(51) Int. Cl.
C07K 14/47 (2006.01)
A61K 38/00 (2006.01)
A61K 9/00 (2006.01)

(52) U.S. Cl.
CPC ........ *C07K 14/4702* (2013.01); *A61K 9/0019* (2013.01); *A61K 38/00* (2013.01); *C07K 2319/30* (2013.01)

(58) Field of Classification Search
CPC ................................................ C07K 14/4702
See application file for complete search history.

(56) References Cited

U.S. PATENT DOCUMENTS

2012/0101029 A1    4/2012    Neufeld et al.
2013/0028896 A1    1/2013    Ong et al.

FOREIGN PATENT DOCUMENTS

WO    WO2010/11792    10/2010

OTHER PUBLICATIONS

Neufeld et al., "The semaphorins: versatile regulators of tumour progression and tumour angiogenesis", Nat. Rev. Cancer, Jun. 26, 2008, vol. 8, pp. 632-645.
Miyato, H. et al., "Semaphorin 3C is involved in the progression of gastric cancer", Cancer Sci., Oct. 15, 2012) vol. 103, No. 11, pp. 1961-1966.
Becker et al., "Potent Inhibitors of Furin and Furin-like Proprotein Convertases Containing Decarboxylated P1 Arginine Mimetics", J. Med. Chem. 2010, Dec. 28, 2009, vol. 53, No. 3, pp. 1067-1075.
Seidah N.G. et al., "The biology and therapeutic targeting of the proprotein convertases", Nat Rev. Drug. Discov., May 2012, vol. 11, pp. 367-383.
Varshavsky et al. "Semaphorin-3B Is an Angiogenesis Inhibitor That Is Inactivated by Furin-Like Pro-Protein Convertases", Cancer Res., Sep. 1, 2008, vol. 68, No. 17, pp. 6922-6931.
Casazza et al., "Tumour growth inhibition and anti-metastatic activity of a mutated furin-resistant Semaphorin 3E isoform", EMBO Mol. Med., Mar. 8, 2012, vol. 4, No. 1-17, pp. 234-250.
Kontermann, "Strategies for extended serum half-life of protein therapeutics", Biotechnology, Aug. 20, 2011, vol. 22 pp. 868-876.
Herman et al. "Increased class 3 semaphorin expression modulates the invasive and adhesive properties of prostate cancer cells". International Journal of Oncology. May 2007, vol. 30, No. 5. pp. 1231-1238.
Hideyo et al. "Semaphorin 3C is involved in the progression of gastric cancer." Cancer Science. Nov. 15, 2012, vol. 103, No. 11. pp. 1961-1966.
Casazza et al. "Tumor growth inhibition and anti-metastatic activity of isoform" EMBO Molecular Medicine. Mar. 13, 2012, vol. 4 No. 3. pp. 234-250.
N. Banu "Semaphorin 3C regulates endothelial cell function by increasing intergrin activity" The FASEB Journal. Oct. 1, 2006, vol. 20 No. 12. pp. 2150-2152.
Tina Dietrich el al. "Inhibition of Inflammatory Lymphangiogenesis by Intergrin [alpha]5 Blockade" The American Journal of Pathology. Jul. 1, 2007, vol. 171 No. 1 pp. 361-372.
Esselens et al. "The Cleavage of Semaphorin 3C Induced by ADAMTS1 Promotes Cell Migration" Journal of Biological Chemistry. Nov. 13, 2009, vol. 285 No. 4. pp. 2463-2473.
Atsuko Sakurai et al. "Semaphorin signaling in angiogenesis, lymphangiogenesis and cancer" Cell Research. Jan. 1, 2012, vol. 22 No. 1. pp. 23-32.
International Search Report for International App. No. PCT/IL2014/050797 dated Jan. 9, 2015.

*Primary Examiner* — Amber D Steele
(74) *Attorney, Agent, or Firm* — Pearl Cohen Zedek; Latzer Baratz LLP

(57) ABSTRACT

The present invention relates, according to some embodiments, to variants of Semaphorin 3C (Sema3C) having amino acid modifications at furin-like pro-protein convertase cleavage sites, rendering these sites resistant to cleavage. The invention further provides, according to certain embodiments, compositions comprising the Sema3C variants, and methods of using the compositions for suppressing the growth of tumors and/or inhibiting the development of tumor metastases.

25 Claims, 19 Drawing Sheets

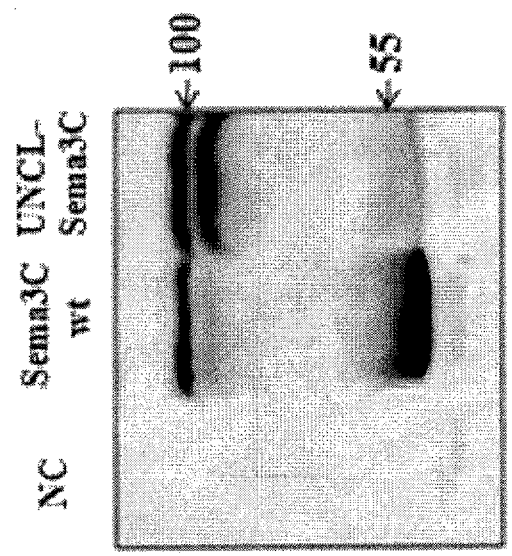
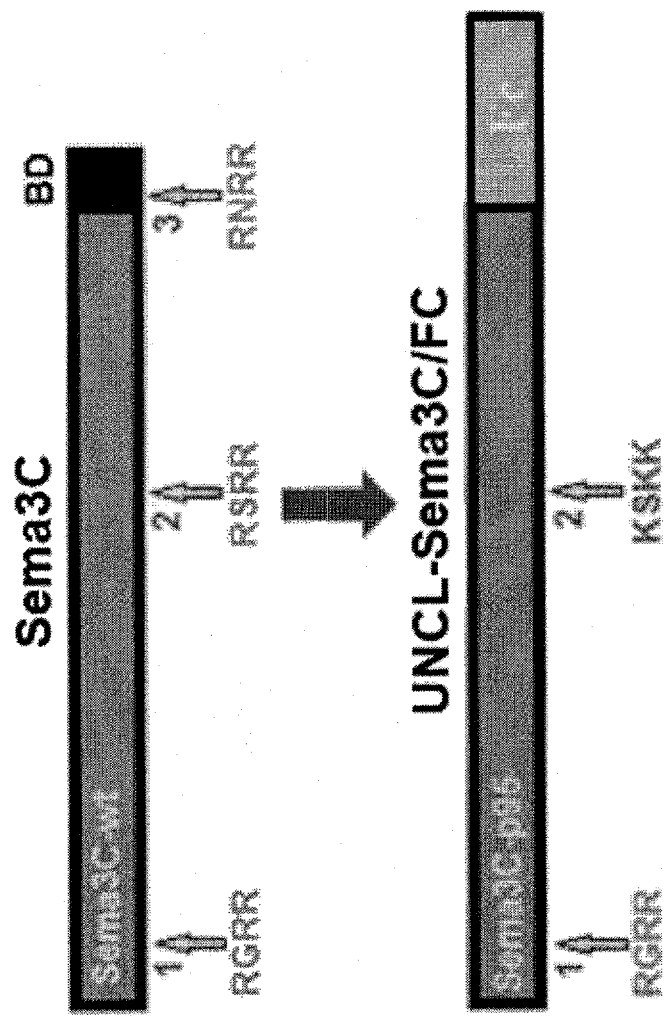
Fig. 1B
Fig. 1A

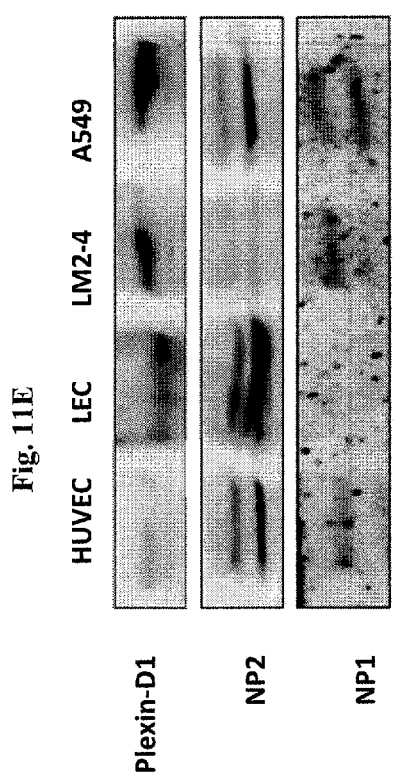

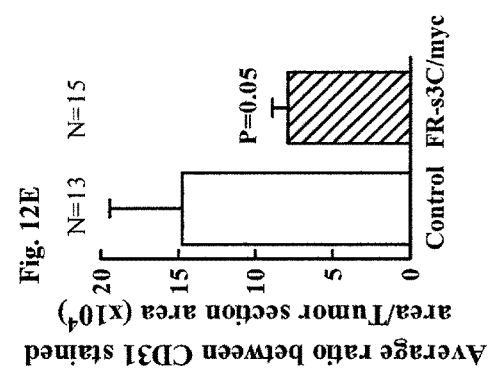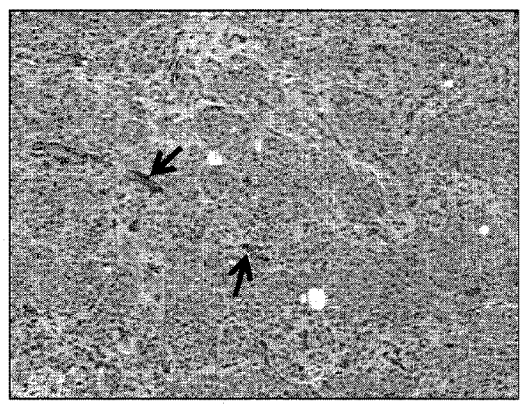

SEQUENCE LISTING

<160> NUMBER OF SEQ ID NOS: 36

<210> SEQ ID NO 1
<211> LENGTH: 751
<212> TYPE: PRT
<213> ORGANISM: Homo sapiens

<400> SEQUENCE: 1

```
Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
```

```
        225                 230                 235                 240
Tyr Phe Phe Phe Lys Glu Lys Leu Thr Asp Asn Asn Arg Ser Thr Lys
                    245                 250                 255

Gln Ile His Ser Met Ile Ala Arg Ile Cys Pro Asn Asp Thr Gly Gly
                260                 265                 270

Leu Arg Ser Leu Val Asn Lys Trp Thr Thr Phe Leu Lys Ala Arg Leu
            275                 280                 285

Val Cys Ser Val Thr Asp Glu Asp Gly Pro Glu Thr His Phe Asp Glu
        290                 295                 300

Leu Glu Asp Val Phe Leu Leu Glu Thr Asp Asn Pro Arg Thr Leu
305                 310                 315                 320

Val Tyr Gly Ile Phe Thr Thr Ser Ser Val Phe Lys Gly Ser Ala
                    325                 330                 335

Val Cys Val Tyr His Leu Ser Asp Ile Gln Thr Val Phe Asn Gly Pro
                340                 345                 350

Phe Ala His Lys Glu Gly Pro Asn His Gln Leu Ile Ser Tyr Gln Gly
            355                 360                 365

Arg Ile Pro Tyr Pro Arg Pro Gly Thr Cys Pro Gly Gly Ala Phe Thr
        370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                    405                 410                 415

Arg Pro Leu Ile Val Arg Ile Gly Thr Asp Tyr Lys Tyr Thr Lys Ile
                420                 425                 430

Ala Val Asp Arg Val Asn Ala Ala Asp Gly Arg Tyr His Val Leu Phe
            435                 440                 445

Leu Gly Thr Asp Arg Gly Thr Val Gln Lys Val Val Leu Pro Thr
        450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                    485                 490                 495

Gln Leu Tyr Val Ser Ser Asn Glu Gly Val Ser Gln Val Ser Leu His
                500                 505                 510

Arg Cys His Ile Tyr Gly Thr Ala Cys Ala Asp Cys Cys Leu Ala Arg
            515                 520                 525

Asp Pro Tyr Cys Ala Trp Asp Gly His Ser Cys Ser Arg Phe Tyr Pro
        530                 535                 540

Thr Gly Lys Arg Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
                    565                 570                 575

Glu Ile Val Gln Tyr Gly Val Lys Asn Asn Thr Thr Phe Leu Glu Cys
                580                 585                 590

Ala Pro Lys Ser Pro Gln Ala Ser Ile Lys Trp Leu Leu Gln Lys Asp
            595                 600                 605

Lys Asp Arg Arg Lys Glu Val Lys Leu Asn Glu Arg Ile Ile Ala Thr
        610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                    645                 650                 655
```

```
Ile Asn Phe Lys Val Leu Asp Ser Glu Met Val Ala Val Thr Asp
                660                 665                 670

Lys Trp Ser Pro Trp Thr Trp Ala Ser Ser Val Arg Ala Leu Pro Phe
    675                 680                 685

His Pro Lys Asp Ile Met Gly Ala Phe Ser His Ser Glu Met Gln Met
690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser Arg Lys Ser Arg Asn Arg Asn Gln Leu Pro Glu Ser
                740                 745                 750

<210> SEQ ID NO 2
<211> LENGTH: 4
<212> TYPE: PRT
<213> ORGANISM: Homo sapiens

<400> SEQUENCE: 2

Arg Gly Arg Arg
1

<210> SEQ ID NO 3
<211> LENGTH: 4
<212> TYPE: PRT
<213> ORGANISM: Homo sapiens

<400> SEQUENCE: 3

Arg Ser Arg Arg
1

<210> SEQ ID NO 4
<211> LENGTH: 4
<212> TYPE: PRT
<213> ORGANISM: Homo sapiens

<400> SEQUENCE: 4

Arg Asn Arg Arg
1

<210> SEQ ID NO 5
<211> LENGTH: 22
<212> TYPE: PRT
<213> ORGANISM: Homo sapiens

<400> SEQUENCE: 5

Lys Met Arg Gly Asp Tyr Gly Lys Leu Lys Ala Leu Ile Asn Ser Arg
1               5                   10                  15

Lys Ser Arg Asn Arg Arg
            20

<210> SEQ ID NO 6
<211> LENGTH: 548
<212> TYPE: PRT
<213> ORGANISM: Homo sapiens

<400> SEQUENCE: 6

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30
```

-continued

```
Phe Asp Glu Leu Arg Glu Thr Lys Thr Ser Glu Tyr Phe Ser Leu Ser
    35                  40                  45

His His Pro Leu Asp Tyr Arg Ile Leu Leu Met Asp Glu Asp Gln Asp
 50                  55                  60

Arg Ile Tyr Val Gly Ser Lys Asp His Ile Leu Ser Leu Asn Ile Asn
 65                  70                  75                  80

Asn Ile Ser Gln Glu Ala Leu Ser Val Phe Trp Pro Ala Ser Thr Ile
                 85                  90                  95

Lys Val Glu Glu Cys Lys Met Ala Gly Lys Asp Pro Thr His Gly Cys
                100                 105                 110

Gly Asn Phe Val Arg Val Ile Gln Thr Phe Asn Arg Thr His Leu Tyr
            115                 120                 125

Val Cys Gly Ser Gly Ala Phe Ser Pro Val Cys Thr Tyr Leu Asn Arg
            130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
        355                 360                 365

Arg Ile Pro Tyr Pro Arg Pro Gly Thr Cys Pro Gly Gly Ala Phe Thr
    370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445
```

```
Leu Gly Thr Asp Arg Gly Thr Val Gln Lys Val Val Leu Pro Thr
    450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
530                 535                 540

Thr Gly Lys Arg
545

<210> SEQ ID NO 7
<211> LENGTH: 777
<212> TYPE: PRT
<213> ORGANISM: Homo sapiens

<400> SEQUENCE: 7

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270
```

-continued

```
Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
        355                 360                 365

Arg Ile Pro Tyr Pro Arg Pro Gly Thr Cys Pro Gly Gly Ala Phe Thr
    370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445

Leu Gly Thr Asp Arg Gly Thr Val Gln Lys Val Val Leu Pro Thr
    450                 455                 460

Asn Asn Ser Val Ser Gly Glu Leu Ile Leu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
    530                 535                 540

Thr Gly Lys Arg Leu Glu Asp Lys Thr His Thr Cys Pro Pro Cys Pro
545                 550                 555                 560

Ala Pro Glu Leu Leu Gly Gly Pro Ser Val Phe Leu Phe Pro Pro Lys
                565                 570                 575

Pro Lys Asp Thr Leu Met Ile Ser Arg Thr Pro Glu Val Thr Cys Val
            580                 585                 590

Val Val Asp Val Ser His Glu Asp Pro Glu Val Lys Phe Asn Trp Tyr
        595                 600                 605

Val Asp Gly Val Glu Val His Asn Ala Lys Thr Lys Pro Arg Glu Glu
    610                 615                 620

Gln Tyr Asn Ser Thr Tyr Arg Val Val Ser Val Leu Thr Val Leu His
625                 630                 635                 640

Gln Asp Trp Leu Asn Gly Lys Glu Tyr Lys Cys Lys Val Ser Asn Lys
                645                 650                 655

Ala Leu Pro Ala Pro Ile Glu Lys Thr Ile Ser Lys Ala Lys Gly Gln
            660                 665                 670

Pro Arg Glu Pro Gln Val Tyr Thr Leu Pro Pro Ser Arg Glu Glu Met
        675                 680                 685
```

Thr Lys Asn Gln Val Ser Leu Thr Cys Leu Val Lys Gly Phe Tyr Pro
    690                 695                 700

Ser Asp Ile Ala Val Glu Trp Glu Ser Asn Gly Gln Pro Glu Asn Asn
705                 710                 715                 720

Tyr Lys Thr Thr Pro Pro Val Leu Asp Ser Asp Gly Ser Phe Phe Leu
                725                 730                 735

Tyr Ser Lys Leu Thr Val Asp Lys Ser Arg Trp Gln Gln Gly Asn Val
            740                 745                 750

Phe Ser Cys Ser Val Met His Glu Ala Leu His Asn His Tyr Thr Gln
        755                 760                 765

Lys Ser Leu Ser Leu Ser Pro Gly Lys
770                 775

<210> SEQ ID NO 8
<211> LENGTH: 967
<212> TYPE: PRT
<213> ORGANISM: Homo sapiens

<400> SEQUENCE: 8

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

```
Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Val Phe Lys Gly Ser Ala
                325                 330                 335

Val Cys Val Tyr His Leu Ser Asp Ile Gln Thr Val Phe Asn Gly Pro
                340                 345                 350

Phe Ala His Lys Glu Gly Pro Asn His Gln Leu Ile Ser Tyr Gln Gly
            355                 360                 365

Arg Ile Pro Tyr Pro Arg Pro Gly Thr Cys Pro Gly Gly Ala Phe Thr
370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
                420                 425                 430

Ala Val Asp Arg Val Asn Ala Ala Asp Gly Arg Tyr His Val Leu Phe
            435                 440                 445

Leu Gly Thr Asp Arg Gly Thr Val Gln Lys Val Val Leu Pro Thr
450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
                500                 505                 510

Arg Cys His Ile Tyr Gly Thr Ala Cys Ala Asp Cys Cys Leu Ala Arg
            515                 520                 525

Asp Pro Tyr Cys Ala Trp Asp Gly His Ser Cys Ser Arg Phe Tyr Pro
            530                 535                 540

Thr Gly Lys Arg Lys Ser Lys Lys Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Lys Asn Asn Thr Thr Phe Leu Glu Cys
                580                 585                 590

Ala Pro Lys Ser Pro Gln Ala Ser Ile Lys Trp Leu Leu Gln Lys Asp
            595                 600                 605

Lys Asp Arg Arg Lys Glu Val Lys Leu Asn Glu Arg Ile Ile Ala Thr
610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Thr Asp
                660                 665                 670

Lys Trp Ser Pro Trp Thr Trp Ala Ser Ser Val Arg Ala Leu Pro Phe
            675                 680                 685

His Pro Lys Asp Ile Met Gly Ala Phe Ser His Ser Glu Met Gln Met
            690                 695                 700
```

Ile Asn Gln Tyr Cys Lys Asp Thr Arg Gln His Gln Gln Gly Asp
705                 710                 715                 720

Glu Ser Gln Lys Met Arg Gly Asp Tyr Gly Lys Leu Lys Ala Leu Ile
            725                 730                 735

Asn Ser Leu Glu Asp Lys Thr His Thr Cys Pro Pro Cys Pro Ala Pro
            740                 745                 750

Glu Leu Leu Gly Gly Pro Ser Val Phe Leu Phe Pro Pro Lys Pro Lys
            755                 760                 765

Asp Thr Leu Met Ile Ser Arg Thr Pro Glu Val Thr Cys Val Val Val
770                 775                 780

Asp Val Ser His Glu Asp Pro Glu Val Lys Phe Asn Trp Tyr Val Asp
785                 790                 795                 800

Gly Val Glu Val His Asn Ala Lys Thr Lys Pro Arg Glu Glu Gln Tyr
            805                 810                 815

Asn Ser Thr Tyr Arg Val Val Ser Val Leu Thr Val Leu His Gln Asp
            820                 825                 830

Trp Leu Asn Gly Lys Glu Tyr Lys Cys Lys Val Ser Asn Lys Ala Leu
835                 840                 845

Pro Ala Pro Ile Glu Lys Thr Ile Ser Lys Ala Lys Gly Gln Pro Arg
850                 855                 860

Glu Pro Gln Val Tyr Thr Leu Pro Pro Ser Arg Glu Glu Met Thr Lys
865                 870                 875                 880

Asn Gln Val Ser Leu Thr Cys Leu Val Lys Gly Phe Tyr Pro Ser Asp
            885                 890                 895

Ile Ala Val Glu Trp Glu Ser Asn Gly Gln Pro Glu Asn Asn Tyr Lys
            900                 905                 910

Thr Thr Pro Pro Val Leu Asp Ser Asp Gly Ser Phe Phe Leu Tyr Ser
            915                 920                 925

Lys Leu Thr Val Asp Lys Ser Arg Trp Gln Gln Gly Asn Val Phe Ser
930                 935                 940

Cys Ser Val Met His Glu Ala Leu His Asn His Tyr Thr Gln Lys Ser
945                 950                 955                 960

Leu Ser Leu Ser Pro Gly Lys
                965

<210> SEQ ID NO 9
<211> LENGTH: 766
<212> TYPE: PRT
<213> ORGANISM: Homo sapiens

<400> SEQUENCE: 9

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

-continued

```
Gly Asn Phe Val Arg Val Ile Gln Thr Phe Asn Arg Thr His Leu Tyr
            115                 120                 125
Val Cys Gly Ser Gly Ala Phe Ser Pro Val Cys Thr Tyr Leu Asn Arg
        130                 135                 140
Gly Arg Arg Ser Glu Asp Gln Val Phe Met Ile Asp Ser Lys Cys Glu
145                 150                 155                 160
Ser Gly Lys Gly Arg Cys Ser Phe Asn Pro Asn Val Asn Thr Val Ser
                165                 170                 175
Val Met Ile Asn Glu Glu Leu Phe Ser Gly Met Tyr Ile Asp Phe Met
                180                 185                 190
Gly Thr Asp Ala Ala Ile Phe Arg Ser Leu Thr Lys Arg Asn Ala Val
            195                 200                 205
Arg Thr Asp Gln His Asn Ser Lys Trp Leu Ser Glu Pro Met Phe Val
        210                 215                 220
Asp Ala His Val Ile Pro Asp Gly Thr Asp Pro Asn Asp Ala Lys Val
225                 230                 235                 240
Tyr Phe Phe Phe Lys Glu Lys Leu Thr Asp Asn Asn Arg Ser Thr Lys
                245                 250                 255
Gln Ile His Ser Met Ile Ala Arg Ile Cys Pro Asn Asp Thr Gly Gly
            260                 265                 270
Leu Arg Ser Leu Val Asn Lys Trp Thr Thr Phe Leu Lys Ala Arg Leu
        275                 280                 285
Val Cys Ser Val Thr Asp Glu Asp Gly Pro Glu Thr His Phe Asp Glu
        290                 295                 300
Leu Glu Asp Val Phe Leu Leu Glu Thr Asp Asn Pro Arg Thr Thr Leu
305                 310                 315                 320
Val Tyr Gly Ile Phe Thr Thr Ser Ser Ser Val Phe Lys Gly Ser Ala
                325                 330                 335
Val Cys Val Tyr His Leu Ser Asp Ile Gln Thr Val Phe Asn Gly Pro
            340                 345                 350
Phe Ala His Lys Glu Gly Pro Asn His Gln Leu Ile Ser Tyr Gln Gly
        355                 360                 365
Arg Ile Pro Tyr Pro Arg Pro Gly Thr Cys Pro Gly Gly Ala Phe Thr
        370                 375                 380
Pro Asn Met Arg Thr Thr Lys Glu Phe Pro Asp Asp Val Val Thr Phe
385                 390                 395                 400
Ile Arg Asn His Pro Leu Met Tyr Asn Ser Ile Tyr Pro Ile His Lys
                405                 410                 415
Arg Pro Leu Ile Val Arg Ile Gly Thr Asp Tyr Lys Tyr Thr Lys Ile
            420                 425                 430
Ala Val Asp Arg Val Asn Ala Ala Asp Gly Arg Tyr His Val Leu Phe
        435                 440                 445
Leu Gly Thr Asp Arg Gly Thr Val Gln Lys Val Val Val Leu Pro Thr
        450                 455                 460
Asn Asn Ser Val Ser Gly Glu Leu Ile Leu Glu Leu Glu Val Phe
465                 470                 475                 480
Lys Asn His Ala Pro Ile Thr Thr Met Lys Ile Ser Ser Lys Lys Gln
                485                 490                 495
Gln Leu Tyr Val Ser Ser Asn Glu Gly Val Ser Gln Val Ser Leu His
            500                 505                 510
Arg Cys His Ile Tyr Gly Thr Ala Cys Ala Asp Cys Cys Leu Ala Arg
        515                 520                 525
```

```
Asp Pro Tyr Cys Ala Trp Asp Gly His Ser Cys Ser Arg Phe Tyr Pro
        530                 535                 540

Thr Gly Lys Arg Lys Ser Lys Lys Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Lys Asn Asn Thr Thr Phe Leu Glu Cys
            580                 585                 590

Ala Pro Lys Ser Pro Gln Ala Ser Ile Lys Trp Leu Leu Gln Lys Asp
        595                 600                 605

Lys Asp Arg Arg Lys Glu Val Lys Leu Asn Glu Arg Ile Ile Ala Thr
610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Val Thr Asp
                660                 665                 670

Lys Trp Ser Pro Trp Thr Trp Ala Ser Ser Val Arg Ala Leu Pro Phe
            675                 680                 685

His Pro Lys Asp Ile Met Gly Ala Phe Ser His Ser Glu Met Gln Met
        690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser Leu Glu Ser Arg Gly Pro Phe Glu Gln Lys Leu Ile Ser Glu
                740                 745                 750

Glu Asp Leu Asn Met His Thr Gly His His His His His His
        755                 760                 765

<210> SEQ ID NO 10
<211> LENGTH: 751
<212> TYPE: PRT
<213> ORGANISM: Homo sapiens

<400> SEQUENCE: 10

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140
```

```
Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
            165                 170                 175

Val Met Ile Asn Glu Glu Leu Phe Ser Gly Met Tyr Ile Asp Phe Met
        180                 185                 190

Gly Thr Asp Ala Ala Ile Phe Arg Ser Leu Thr Lys Arg Asn Ala Val
    195                 200                 205

Arg Thr Asp Gln His Asn Ser Lys Trp Leu Ser Glu Pro Met Phe Val
210                 215                 220

Asp Ala His Val Ile Pro Asp Gly Thr Asp Pro Asn Asp Ala Lys Val
225                 230                 235                 240

Tyr Phe Phe Lys Glu Lys Leu Thr Asp Asn Asn Arg Ser Thr Lys
            245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
            355                 360                 365

Arg Ile Pro Tyr Pro Arg Pro Gly Thr Cys Pro Gly Gly Ala Phe Thr
        370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445

Leu Gly Thr Asp Arg Gly Thr Val Gln Lys Val Val Val Leu Pro Thr
    450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
            485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
            515                 520                 525

Asp Pro Tyr Cys Ala Trp Asp Gly His Ser Cys Ser Arg Phe Tyr Pro
    530                 535                 540

Thr Gly Lys Arg Lys Ser Lys Lys Gln Asp Val Arg His Gly Asn Pro
545                 550                 555                 560
```

Leu Thr Gln Cys Arg Gly Phe Asn Leu Lys Ala Tyr Arg Asn Ala Ala
                565                 570                 575

Glu Ile Val Gln Tyr Gly Val Lys Asn Asn Thr Thr Phe Leu Glu Cys
            580                 585                 590

Ala Pro Lys Ser Pro Gln Ala Ser Ile Lys Trp Leu Leu Gln Lys Asp
        595                 600                 605

Lys Asp Arg Arg Lys Glu Val Lys Leu Asn Glu Arg Ile Ile Ala Thr
    610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Thr Asp
                660                 665                 670

Lys Trp Ser Pro Trp Thr Trp Ala Ser Ser Val Arg Ala Leu Pro Phe
            675                 680                 685

His Pro Lys Asp Ile Met Gly Ala Phe Ser His Ser Glu Met Gln Met
        690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser Arg Lys Ser Arg Asn Arg Arg Asn Gln Leu Pro Glu Ser
            740                 745                 750

<210> SEQ ID NO 11
<211> LENGTH: 4
<212> TYPE: PRT
<213> ORGANISM: Homo sapiens

<400> SEQUENCE: 11

Arg Ser Lys Arg
1

<210> SEQ ID NO 12
<211> LENGTH: 4
<212> TYPE: PRT
<213> ORGANISM: Homo sapiens

<400> SEQUENCE: 12

Lys Ser Lys Arg
1

<210> SEQ ID NO 13
<211> LENGTH: 4
<212> TYPE: PRT
<213> ORGANISM: Homo sapiens

<400> SEQUENCE: 13

Lys Ser Lys Lys
1

<210> SEQ ID NO 14
<211> LENGTH: 980
<212> TYPE: PRT
<213> ORGANISM: Homo sapiens

<400> SEQUENCE: 14

Met Ala Phe Arg Thr Ile Cys Val Leu Val Gly Val Phe Ile Cys Ser
1               5                   10                  15

```
Ile Cys Val Lys Gly Ser Ser Gln Pro Gln Ala Arg Val Tyr Leu Thr
             20                  25                  30
Phe Asp Glu Leu Arg Glu Thr Lys Thr Ser Glu Tyr Phe Ser Leu Ser
         35                  40                  45
His His Pro Leu Asp Tyr Arg Ile Leu Leu Met Asp Glu Asp Gln Asp
     50                  55                  60
Arg Ile Tyr Val Gly Ser Lys Asp His Ile Leu Ser Leu Asn Ile Asn
 65                  70                  75                  80
Asn Ile Ser Gln Glu Ala Leu Ser Val Phe Trp Pro Ala Ser Thr Ile
                 85                  90                  95
Lys Val Glu Glu Cys Lys Met Ala Gly Lys Asp Pro Thr His Gly Cys
            100                 105                 110
Gly Asn Phe Val Arg Val Ile Gln Thr Phe Asn Arg Thr His Leu Tyr
        115                 120                 125
Val Cys Gly Ser Gly Ala Phe Ser Pro Val Cys Thr Tyr Leu Asn Arg
    130                 135                 140
Gly Arg Arg Ser Glu Asp Gln Val Phe Met Ile Asp Ser Lys Cys Glu
145                 150                 155                 160
Ser Gly Lys Gly Arg Cys Ser Phe Asn Pro Asn Val Asn Thr Val Ser
                165                 170                 175
Val Met Ile Asn Glu Glu Leu Phe Ser Gly Met Tyr Ile Asp Phe Met
            180                 185                 190
Gly Thr Asp Ala Ala Ile Phe Arg Ser Leu Thr Lys Arg Asn Ala Val
        195                 200                 205
Arg Thr Asp Gln His Asn Ser Lys Trp Leu Ser Glu Pro Met Phe Val
    210                 215                 220
Asp Ala His Val Ile Pro Asp Gly Thr Asp Pro Asn Asp Ala Lys Val
225                 230                 235                 240
Tyr Phe Phe Phe Lys Glu Lys Leu Thr Asp Asn Asn Arg Ser Thr Lys
                245                 250                 255
Gln Ile His Ser Met Ile Ala Arg Ile Cys Pro Asn Asp Thr Gly Gly
            260                 265                 270
Leu Arg Ser Leu Val Asn Lys Trp Thr Thr Phe Leu Lys Ala Arg Leu
        275                 280                 285
Val Cys Ser Val Thr Asp Glu Asp Gly Pro Glu Thr His Phe Asp Glu
    290                 295                 300
Leu Glu Asp Val Phe Leu Leu Glu Thr Asp Asn Pro Arg Thr Thr Leu
305                 310                 315                 320
Val Tyr Gly Ile Phe Thr Thr Ser Ser Ser Val Phe Lys Gly Ser Ala
                325                 330                 335
Val Cys Val Tyr His Leu Ser Asp Ile Gln Thr Val Phe Asn Gly Pro
            340                 345                 350
Phe Ala His Lys Glu Gly Pro Asn His Gln Leu Ile Ser Tyr Gln Gly
        355                 360                 365
Arg Ile Pro Tyr Pro Arg Pro Gly Thr Cys Pro Gly Gly Ala Phe Thr
    370                 375                 380
Pro Asn Met Arg Thr Thr Lys Glu Phe Pro Asp Asp Val Val Thr Phe
385                 390                 395                 400
Ile Arg Asn His Pro Leu Met Tyr Asn Ser Ile Tyr Pro Ile His Lys
                405                 410                 415
Arg Pro Leu Ile Val Arg Ile Gly Thr Asp Tyr Lys Tyr Thr Lys Ile
            420                 425                 430
```

```
Ala Val Asp Arg Val Asn Ala Asp Gly Arg Tyr His Val Leu Phe
            435                 440                 445

Leu Gly Thr Asp Arg Gly Thr Val Gln Lys Val Val Leu Pro Thr
    450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
            515                 520                 525

Asp Pro Tyr Cys Ala Trp Asp Gly His Ser Cys Ser Arg Phe Tyr Pro
    530                 535                 540

Thr Gly Lys Arg Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Lys Asn Asn Thr Thr Phe Leu Glu Cys
            580                 585                 590

Ala Pro Lys Ser Pro Gln Ala Ser Ile Lys Trp Leu Leu Gln Lys Asp
    595                 600                 605

Lys Asp Arg Arg Lys Glu Val Lys Leu Asn Glu Arg Ile Ile Ala Thr
    610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Thr Asp
                660                 665                 670

Lys Trp Ser Pro Trp Thr Trp Ala Ser Ser Val Arg Ala Leu Pro Phe
    675                 680                 685

His Pro Lys Asp Ile Met Gly Ala Phe Ser His Ser Glu Met Gln Met
    690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser Arg Lys Ser Arg Asn Arg Arg Asn Gln Leu Pro Glu Ser Leu
            740                 745                 750

Glu Asp Lys Thr His Thr Cys Pro Pro Cys Pro Ala Pro Glu Leu Leu
            755                 760                 765

Gly Gly Pro Ser Val Phe Leu Phe Pro Pro Lys Pro Lys Asp Thr Leu
    770                 775                 780

Met Ile Ser Arg Thr Pro Glu Val Thr Cys Val Val Val Asp Val Ser
785                 790                 795                 800

His Glu Asp Pro Glu Val Lys Phe Asn Trp Tyr Val Asp Gly Val Glu
                805                 810                 815

Val His Asn Ala Lys Thr Lys Pro Arg Glu Glu Gln Tyr Asn Ser Thr
            820                 825                 830

Tyr Arg Val Val Ser Val Leu Thr Val Leu His Gln Asp Trp Leu Asn
    835                 840                 845

Gly Lys Glu Tyr Lys Cys Lys Val Ser Asn Lys Ala Leu Pro Ala Pro
```

```
                850                 855                 860
Ile Glu Lys Thr Ile Ser Lys Ala Lys Gly Gln Pro Arg Glu Pro Gln
865                 870                 875                 880

Val Tyr Thr Leu Pro Pro Ser Arg Glu Glu Met Thr Lys Asn Gln Val
                885                 890                 895

Ser Leu Thr Cys Leu Val Lys Gly Phe Tyr Pro Ser Asp Ile Ala Val
                900                 905                 910

Glu Trp Glu Ser Asn Gly Gln Pro Glu Asn Asn Tyr Lys Thr Thr Pro
                915                 920                 925

Pro Val Leu Asp Ser Asp Gly Ser Phe Phe Leu Tyr Ser Lys Leu Thr
                930                 935                 940

Val Asp Lys Ser Arg Trp Gln Gln Gly Asn Val Phe Ser Cys Ser Val
945                 950                 955                 960

Met His Glu Ala Leu His Asn His Tyr Thr Gln Lys Ser Leu Ser Leu
                965                 970                 975

Ser Pro Gly Lys
                980
```

<210> SEQ ID NO 15
<211> LENGTH: 2256
<212> TYPE: DNA
<213> ORGANISM: Homo sapiens

<400> SEQUENCE: 15

```
atggcattcc ggacaatttg cgtgttggtt ggagtattta tttgttctat ctgtgtgaaa      60
ggatcttccc agccccaagc aagagtttat ttaacatttg atgaacttcg agaaaccaag     120
acctctgaat acttcagcct ttcccaccat cctttagact acaggatttt attaatggat     180
gaagatcagg accggatata tgtgggaagc aaagatcaca ttctttccct gaatattaac     240
aatataagtc aagaagcttt gagtgttttc tggccagcat ctacaatcaa agttgaagaa     300
tgcaaaatgg ctggcaaaga tcccacacac ggctgtggga ctttgtccg tgtaattcag      360
actttcaatc gcacacattt gtatgtctgt gggagtggcg ctttcagtcc tgtctgtact     420
tacttgaaca gagggaggag atcagaggac caagttttca tgattgactc caagtgtgaa     480
tctggaaaag acgctgctc tttcaacccc aacgtgaaca cggtgtctgt tatgatcaat     540
gaggagcttt tctctggaat gtatatagat ttcatgggga cagatgctgc tatttttcga     600
agtttaacca gaggaatgc ggtcagaact gatcaacata attccaaatg gctaagtgaa     660
cctatgtttg tagatgcaca tgtcatccca gatggtactg atccaaatga tgctaaggtg     720
tacttcttct tcaaagaaaa actgactgac aataacagga gcacgaaaca gattcattcc     780
atgattgctc gaatatgtcc taatgacact ggtggactgc gtagccttgt caacaagtgg     840
accactttct taaaggcgag gctggtgtgc tcggtaacag atgaagacgg cccagaaaca     900
cactttgatg aattagagga tgtgtttctg ctggaaactg ataacccgag acaacacta     960
gtgtatggca ttttacaac atcaagctca gttttcaaag atcagccgt gtgtgtgtat    1020
catttatctg atatacagac tgtgtttaat gggccttttg cccacaaaga agggcccaat    1080
catcagctga tttcctatca gggcagaatt ccatatcctc gccctggaac ttgtccagga    1140
ggagcattta cacccaatat gcgaaccacc aaggagttcc cagatgatgt tgtcactttt    1200
attcggaacc atcctctcat gtacaattcc atctacccaa tccacaaaag gcctttgatt    1260
gttcgtattg cactgactca agtatacaa agatagctg tggatcgagt gaacgctgct    1320
gatgggagat accatgtcct gtttctcgga acagatcggg gtactgtgca aaaagtggtt    1380
```

```
gttcttccta ctaacaactc tgtcagtggc gagctcattc tggaggagct ggaagtcttt    1440
aagaatcatg ctcctataac aacaatgaaa atttcatcta aaaagcaaca gttgtatgtg    1500
agttccaatg aagggtttc ccaggtatct ctgcaccgct gccacatcta tggtacagcc     1560
tgtgctgact gctgcctggc gcgggaccct tattgcgcct gggatggcca ttcctgttcc    1620
agattctacc caactgggaa acggaggagc cgaagacaag atgtgagaca tggaaaccca    1680
ctgactcaat gcagaggatt taatctaaaa gcatacagaa atgcagctga aattgtgcag    1740
tatggagtaa aaataacac cacttttctg gagtgtgccc ccaagtctcc gcaggcatct     1800
atcaagtggc tgttacagaa agacaaagac aggaggaaag aggttaagct gaatgaacga    1860
ataatagcca cttcacaggg actcctgatc cgctctgttc agggttctga ccaaggactt    1920
tatcactgca ttgctacaga aaatagtttc aagcagacca tagccaagat caacttcaaa    1980
gttttagatt cagaaatggt ggctgttgtg acggacaaat ggtccccatg gacctgggcc    2040
agctctgtga gggctttacc cttccacccg aaggacatca tggggcatt cagccactca    2100 gaaatgcaga tgattaacca atattgcaaa gacactcggc agcaacatca gcagggagat    2160
gaatcacaga aaatgagagg ggactatggc aagttaaagg ccctcatcaa tagtcggaaa    2220
agtagaaaca ggaggaatca gttgccagag tcataa                              2256

<210> SEQ ID NO 16
<211> LENGTH: 12
<212> TYPE: DNA
<213> ORGANISM: Homo sapiens

<400> SEQUENCE: 16
agagggagga ga                                                          12

<210> SEQ ID NO 17
<211> LENGTH: 12
<212> TYPE: DNA
<213> ORGANISM: Homo sapiens

<400> SEQUENCE: 17
aggagccgaa ga                                                          12

<210> SEQ ID NO 18
<211> LENGTH: 12
<212> TYPE: DNA
<213> ORGANISM: Homo sapiens

<400> SEQUENCE: 18
agaaacagga gg                                                          12

<210> SEQ ID NO 19
<211> LENGTH: 66
<212> TYPE: DNA
<213> ORGANISM: Homo sapiens

<400> SEQUENCE: 19
aaaatgagag gggactatgg caagttaaag gccctcatca atagtcggaa aagtagaaac    60
aggagg                                                                66

<210> SEQ ID NO 20
<211> LENGTH: 1644
<212> TYPE: DNA
<213> ORGANISM: Homo sapiens
```

<400> SEQUENCE: 20

```
atggcattcc ggacaatttg cgtgttggtt ggagtattta tttgttctat ctgtgtgaaa      60
ggatcttccc agccccaagc aagagtttat ttaacatttg atgaacttcg agaaaccaag     120
acctctgaat acttcagcct ttcccaccat cctttagact acaggatttt attaatggat     180
gaagatcagg accggatata tgtgggaagc aaagatcaca ttctttccct gaatattaac     240
aatataagtc aagaagcttt gagtgttttc tggccagcat ctacaatcaa agttgaagaa     300
tgcaaaatgg ctggcaaaga tcccacacac ggctgtggga actttgtccg tgtaattcag     360
actttcaatc gcacacattt gtatgtctgt gggagtggcg ctttcagtcc tgtctgtact     420
tacttgaaca gagggaggag atcagaggac caagttttca tgattgactc caagtgtgaa     480
tctggaaaag gacgctgctc tttcaaccnc aacgtgaaca cggtgtctgt tatgatcaat     540
gaggagcttt tctctggaat gtatatagat ttcatgggga cagatgctgc tattttttcga   600
agtttaacca gaggaatgc ggtcagaact gatcaacata attccaaatg ctaagtgaa      660
cctatgtttg tagatgcaca tgtcatccca gatggtactg atccaaatga tgctaaggtg    720
tacttcttct tcaaagaaaa actgactgac aataacagga gcacgaaaca gattcattcc   780
atgattgctc gaatatgtcc taatgacact ggtggactgc gtagccttgt caacaagtgg   840
accactttct taaaggcgag gctggtgtgc tcggtaacag atgaagacgg cccagaaaca    900
cactttgatg aattagagga tgtgtttctg ctggaaactg ataacccgag acaacacta    960
gtgtatggca ttttttacaac atcaagctca gttttcaaag gatcagccgt gtgtgtgtat  1020
catttatctg atatacagac tgtgtttaat gggccttttg cccacaaaga agggcccaat  1080
catcagctga tttcctatca gggcagaatt ccatatcctc gccctggaac ttgtccagga   1140
ggagcattta cacccaatat gcgaaccacc aaggagttcc cagatgatgt tgtcactttt   1200
attcggaacc atcctctcat gtacaattcc atctacccaa tccacaaaag gcctttgatt    1260
gttcgtattg gcactgacta caagtataca aagatagctg tggatcgagt gaacgctgct    1320
gatgggagat accatgtcct gtttctcgga acagatcggg gtactgtgca aaaagtggtt   1380
gttcttccta ctaacaactc tgtcagtggc gagctcattc tggaggagct ggaagtcttt   1440
aagaatcatg ctcctataac aacaatgaaa atttcatcta aaaagcaaca gttgtatgtg   1500
agttccaatg aagggggttc ccaggtatct ctgcaccgct gccacatcta tggtacagcc   1560
tgtgctgact gctgcctggc gcgggaccct tattgcgcct gggatggcca ttcctgttcc   1620
agattctacc caactgggaa acgg                                           1644
```

<210> SEQ ID NO 21
<211> LENGTH: 2334
<212> TYPE: DNA
<213> ORGANISM: Homo sapiens

<400> SEQUENCE: 21

```
atggcattcc ggacaatttg cgtgttggtt ggagtattta tttgttctat ctgtgtgaaa      60
ggatcttccc agccccaagc aagagtttat ttaacatttg atgaacttcg agaaaccaag     120
acctctgaat acttcagcct ttcccaccat cctttagact acaggatttt attaatggat     180
gaagatcagg accggatata tgtgggaagc aaagatcaca ttctttccct gaatattaac     240
aatataagtc aagaagcttt gagtgttttc tggccagcat ctacaatcaa agttgaagaa     300
tgcaaaatgg ctggcaaaga tcccacacac ggctgtggga actttgtccg tgtaattcag     360
actttcaatc gcacacattt gtatgtctgt gggagtggcg ctttcagtcc tgtctgtact     420
```

```
tacttgaaca gagggaggag atcagaggac caagttttca tgattgactc caagtgtgaa    480
tctggaaaag gacgctgctc tttcaacccc aacgtgaaca cggtgtctgt tatgatcaat    540
gaggagcttt tctctggaat gtatatagat ttcatgggga cagatgctgc tattttcga     600 agtttaacca agaggaatgc ggtcagaact gatcaacata attccaaatg ctaagtgaa     660 cctatgtttg tagatgcaca tgtcatccca gatggtactg atccaaatga tgctaaggtg    720
tacttcttct tcaaagaaaa actgactgac aataacagga gcacgaaaca gattcattcc    780
atgattgctc gaatatgtcc taatgacact ggtggactgc gtagccttgt caacaagtgg    840
accactttct taaaggcgag gctggtgtgc tcggtaacag atgaagacgg cccagaaaca    900
cactttgatg aattagagga tgtgtttctg ctggaaactg ataacccgag acaacacta     960 gtgtatggca tttttacaac atcaagctca gttttcaaag gatcagccgt gtgtgtgtat   1020
catttatctg atatacagac tgtgtttaat gggccttttg cccacaaaga agggcccaat   1080
catcagctga tttcctatca gggcagaatt ccatatcctc gccctggaac ttgtccagga   1140
ggagcattta cacccaatat gcgaaccacc aaggagttcc cagatgatgt tgtcactttt   1200
attcggaacc atcctctcat gtacaattcc atctacccaa tccacaaaag gcctttgatt   1260
gttcgtattg gcactgacta caagtataca aagatagctg tggatcgagt gaacgctgct   1320
gatgggagat accatgtcct gtttctcgga acagatcggg gtactgtgca aaaagtggtt   1380
gttcttccta ctaacaactc tgtcagtggc gagctcattc tggaggagct ggaagtcttt   1440
aagaatcatg ctcctataac aacaatgaaa atttcatcta aaaagcaaca gttgtatgtg   1500
agttccaatg aaggggtttc ccaggtatct ctgcaccgct gccacatcta tggtacagcc   1560
tgtgctgact gctgcctggc gcgggaccct tattgcgcct gggatggcca ttcctgttcc   1620
agattctacc caactgggaa acggctcgag gacaaaactc acacatgccc accgtgccca   1680
gcacctgaac tcctggggg accgtcagtc ttcctcttcc ccccaaaacc caaggacacc   1740
ctcatgatct cccggacccc tgaggtcaca tgcgtggtgg tggacgtgag ccacgaagac   1800
cctgaggtca agttcaactg gtacgtggac ggcgtggagg tgcataatgc caagacaaag   1860
ccgcgggagg agcagtacaa cagcacgtac cgtgtggtca gcgtcctcac cgtcctgcac   1920
caggactggc tgaatggcaa ggagtacaag tgcaaggtct ccaacaaagc cctcccagcc   1980
cccatcgaga aaaccatctc caaagccaaa gggcagcccc gagaaccaca ggtgtacacc   2040
ctgcccccat cccgggagga tgaccaag aaccaggtca gcctgacctg cctggtcaaa   2100
ggcttctatc ccagcgacat cgccgtggag tgggagagca tgggcagcc ggagaacaac   2160 tacaagacca cgcctcccgt gctggactcc gacggctcct tcttcctcta tagcaagctc   2220
accgtggaca gagcaggtg gcagcagggg aacgtcttct catgctccgt gatgcatgag   2280
gctctgcaca accactacac gcagaagagc ctctccctgt ccccgggtaa atga         2334
```

<210> SEQ ID NO 22
<211> LENGTH: 2904
<212> TYPE: DNA
<213> ORGANISM: Homo sapiens

<400> SEQUENCE: 22

```
atggcattcc ggacaatttg cgtgttggtt ggagtattta tttgttctat ctgtgtgaaa     60
ggatcttccc agccccaagc aagagtttat ttaacatttg atgaacttcg agaaaccaag    120
acctctgaat acttcagcct ttcccaccat ccttagact acaggatttt attaatggat   180
```

```
gaagatcagg accggatata tgtgggaagc aaagatcaca ttctttccct gaatattaac      240
aatataagtc aagaagcttt gagtgttttc tggccagcat ctacaatcaa agttgaagaa      300
tgcaaaatgg ctggcaaaga tcccacacac ggctgtggga actttgtccg tgtaattcag      360
actttcaatc gcacacattt gtatgtctgt gggagtggcg ctttcagtcc tgtctgtact      420
tacttgaaca gagggaggag atcagaggac caagttttca tgattgactc caagtgtgaa      480
tctggaaaag gacgctgctc tttcaacccc aacgtgaaca cggtgtctgt tatgatcaat      540
gaggagcttt tctctggaat gtatatagat ttcatgggga cagatgctgc tattttcga       600 agtttaacca agaggaatgc ggtcagaact gatcaacata attccaaatg ctaagtgaa       660 cctatgtttg tagatgcaca tgtcatccca gatggtactg atccaaatga tgctaaggtg      720
tacttcttct tcaaagaaaa actgactgac aataacagga gcacgaaaca gattcattcc      780
atgattgctc gaatatgtcc taatgacact ggtggactgc gtagccttgt caacaagtgg      840
accactttct taaaggcgag gctggtgtgc tcggtaacag atgaagacgg cccagaaaca      900
cactttgatg aattagagga tgtgtttctg ctggaaactg ataacccgag acaacacta      960 gtgtatggca ttttacaac atcaagctca gttttcaaag gatcagccgt gtgtgtgtat      1020
catttatctg atatacagac tgtgtttaat gggccttttg cccacaaaga agggcccaat     1080
catcagctga tttcctatca gggcagaatt ccatatcctc gccctggaac ttgtccagga     1140
ggagcattta cacccaatat gcgaaccacc aaggagttcc cagatgatgt tgtcactttt     1200
attcggaacc atcctctcat gtacaattcc atctacccaa tccacaaaag gcctttgatt     1260
gttcgtattg gcactgacta caagtataca agatagctg tggatcgagt gaacgctgct     1320
gatgggagat accatgtcct gtttctcgga acagatcggg gtactgtgca aaaagtggtt     1380
gttcttccta ctaacaactc tgtcagtggc gagctcattc tggaggagct ggaagtcttt     1440
aagaatcatg ctcctataac aacaatgaaa atttcatcta aaaagcaaca gttgtatgtg     1500
agttccaatg aaggggtttc ccaggtatct ctgcaccgct gccacatcta tggtacagcc     1560
tgtgctgact gctgcctggc gcgggaccct tattgcgcct gggatggcca ttcctgttcc     1620
agattctacc caactgggaa acggaagagc aaaaaacaag atgtgagaca tggaaaccca     1680
ctgactcaat gcagaggatt taatctaaaa gcatacagaa atgcagctga aattgtgcag     1740
tatggagtaa aaaataacac cacttttctg gagtgtgccc ccaagtctcc gcaggcatct     1800
atcaagtggc tgttacagaa agacaaagac aggaggaaag aggttaagct gaatgaacga     1860
ataatagcca cttcacaggg actcctgatc cgctctgttc agggttctga ccaaggactt     1920
tatcactgca ttgctacaga aaatagtttc aagcagacca tagccaagat caacttcaaa     1980
gttttagatt cagaaatggt ggctgttgtg acggacaaat ggtccccatg gacctgggcc     2040
agctctgtga gggctttacc cttccacccg aaggacatca tgggggcatt cagccactca     2100
gaaatgcaga tgattaacca atattgcaaa gacactcggc agcaacatca gcagggagat     2160
gaatcacaga aaatgagagg ggactatggc aagttaaagg ccctcatcaa tagtctcgag     2220
gacaaaactc acacatgccc accgtgccca gcacctgaac tcctgggggg accgtcagtc     2280
ttcctcttcc ccccaaaacc caaggacacc ctcatgatct cccggacccc tgaggtcaca     2340
tgcgtggtgg tggacgtgag ccacgaagac cctgaggtca agttcaactg gtacgtggac     2400
ggcgtggagg tgcataatgc caagacaaag ccgcgggagg agcagtacaa cagcacgtac     2460
cgtgtggtca gcgtcctcac cgtcctgcac caggactggc tgaatggcaa ggagtacaag     2520
tgcaaggtct ccaacaaagc cctcccagcc cccatcgaga aaaccatctc caaagccaaa     2580
```

| | |
|---|---|
| gggcagcccc gagaaccaca ggtgtacacc ctgcccccat cccgggagga gatgaccaag | 2640 |
| aaccaggtca gcctgacctg cctggtcaaa ggcttctatc ccagcgacat cgccgtggag | 2700 |
| tgggagagca atgggcagcc ggagaacaac tacaagacca cgcctcccgt gctggactcc | 2760 |
| gacggctcct tcttcctcta tagcaagctc accgtggaca gagcaggtg gcagcagggg | 2820 |
| aacgtcttct catgctccgt gatgcatgag gctctgcaca accactacac gcagaagagc | 2880 |
| ctctcccctgt ccccgggtaa atga | 2904 |

<210> SEQ ID NO 23
<211> LENGTH: 2301
<212> TYPE: DNA
<213> ORGANISM: Homo sapiens

<400> SEQUENCE: 23

| | |
|---|---|
| atggcattcc ggacaatttg cgtgttggtt ggagtattta tttgttctat ctgtgtgaaa | 60 |
| ggatcttccc agccccaagc aagagtttat ttaacatttg atgaacttcg agaaaccaag | 120 |
| acctctgaat acttcagcct ttcccaccat cctttagact acaggatttt attaatggat | 180 |
| gaagatcagg accggatata tgtgggaagc aaagatcaca ttctttccct gaatattaac | 240 |
| aatataagtc aagaagcttt gagtgttttc tggccagcat ctacaatcaa agttgaagaa | 300 |
| tgcaaaatgg ctggcaaaga tcccacacac ggctgtggga ctttgtccg tgtaattcag | 360 |
| actttcaatc gcacacattt gtatgtctgt gggagtggcg ctttcagtcc tgtctgtact | 420 |
| tacttgaaca gagggaggag atcagaggac caagttttca tgattgactc caagtgtgaa | 480 |
| tctggaaaag gacgctgctc tttcaacccc aacgtgaaca cggtgtctgt tatgatcaat | 540 |
| gaggagctttt tctctggaat gtatatagat ttcatgggga cagatgctgc tatttttcga | 600 |
| agtttaacca agaggaatgc ggtcagaact gatcaacata attccaaatg gctaagtgaa | 660 |
| cctatgtttg tagatgcaca tgtcatccca gatggtactg atccaaatga tgctaaggtg | 720 |
| tacttcttct tcaaagaaaa actgactgac aataacagga gcacgaaaca gattcattcc | 780 |
| atgattgctc gaatatgtcc taatgacact ggtggactgc gtagccttgt caacaagtgg | 840 |
| accactttct taaaggcgag gctggtgtgc tcggtaacag atgaagacgg cccagaaaca | 900 |
| cactttgatg aattagagga tgtgtttctg ctggaaactg ataacccgag acaacacta | 960 |
| gtgtatggca ttttacaac atcaagctca gttttcaaag gatcagccgt gtgtgtgtat | 1020 |
| catttatctg atatacagac tgtgtttaat gggcctttg cccacaaaga agggcccaat | 1080 |
| catcagctga tttcctatca gggcagaatt ccatatcctc gccctggaac ttgtccagga | 1140 |
| ggagcattta cacccaatat gcgaaccacc aaggagttcc cagatgatgt tgtcactttt | 1200 |
| attcggaacc atcctctcat gtacaattcc atctacccaa tccacaaaag gcctttgatt | 1260 |
| gttcgtattg gcactgacta caagtataca aagatagctg tggatcgagt gaacgctgct | 1320 |
| gatgggagat accatgtcct gttttctcgga acagatcggg gtactgtgca aaaagtggtt | 1380 |
| gttcttccta ctaacaactc tgtcagtggc gagctcattc tggaggagct ggaagtcttt | 1440 |
| aagaatcatg ctcctataac aacaatgaaa atttcatcta aaaagcaaca gttgtatgtg | 1500 |
| agttccaatg aagggggttc ccaggtatct ctgcaccgct gccacatcta tggtacagcc | 1560 |
| tgtgctgact gctgcctggc gcgggaccct tattgcgcct gggatggcca ttcctgttcc | 1620 |
| agattctacc caactgggaa acggaagagc aaaaaacaag atgtgagaca tggaaaccca | 1680 |
| ctgactcaat gcagaggatt taatctaaaa gcatacagaa atgcagctga aattgtgcag | 1740 |

```
tatggagtaa aaaataacac cacttttctg gagtgtgccc ccaagtctcc gcaggcatct      1800
atcaagtggc tgttacagaa agacaaagac aggaggaaag aggttaagct gaatgaacga      1860
ataatagcca cttcacaggg actcctgatc cgctctgttc agggttctga ccaaggactt      1920
tatcactgca ttgctacaga aaatagtttc aagcagacca tagccaagat caacttcaaa      1980
gttttagatt cagaaatggt ggctgttgtg acggacaaat ggtccccatg gacctgggcc      2040
agctctgtga gggctttacc cttccacccg aaggacatca tgggggcatt cagccactca      2100
gaaatgcaga tgattaacca atattgcaaa gacactcggc agcaacatca gcagggagat      2160
gaatcacaga aaatgagagg ggactatggc aagttaaagg ccctcatcaa tagtctcgag      2220
tctagagggc ccttcgaaca aaaactcatc tcagaagagg atctgaatat gcataccggt      2280
catcatcacc atcaccattg a                                                2301

<210> SEQ ID NO 24
<211> LENGTH: 38
<212> TYPE: DNA
<213> ORGANISM: Homo sapiens

<400> SEQUENCE: 24
gggaaacgga ggagcaaaag acaagatgtg agacatgg                              38

<210> SEQ ID NO 25
<211> LENGTH: 38
<212> TYPE: DNA
<213> ORGANISM: Homo sapiens

<400> SEQUENCE: 25
ccatgtctca catcttgtct tttgctcctc cgtttccc                              38

<210> SEQ ID NO 26
<211> LENGTH: 47
<212> TYPE: DNA
<213> ORGANISM: Homo sapiens

<400> SEQUENCE: 26
tacccaactg ggaaacggaa gagcaaaaga caagatgtga gacatgg                    47

<210> SEQ ID NO 27
<211> LENGTH: 47
<212> TYPE: DNA
<213> ORGANISM: Homo sapiens

<400> SEQUENCE: 27
ccatgtctca catcttgtct tttgctcttc cgtttccag ttgggta                     47

<210> SEQ ID NO 28
<211> LENGTH: 44
<212> TYPE: DNA
<213> ORGANISM: Homo sapiens

<400> SEQUENCE: 28
gggaaacgga agagcaaaaa acaagatgtg agacatggaa accc                       44

<210> SEQ ID NO 29
<211> LENGTH: 44
<212> TYPE: DNA
<213> ORGANISM: Homo sapiens

<400> SEQUENCE: 29
gggtttccat gtctcacatc ttgttttttg ctcttccgtt tccc                       44
```

-continued

<210> SEQ ID NO 30
<211> LENGTH: 29
<212> TYPE: DNA
<213> ORGANISM: Homo sapiens

<400> SEQUENCE: 30
cgggatccac catggcatcg gacaatttg                                29

<210> SEQ ID NO 31
<211> LENGTH: 32
<212> TYPE: DNA
<213> ORGANISM: Homo sapiens

<400> SEQUENCE: 31
cgctcgagac tattgatgag ggcctttaac tt                            32

<210> SEQ ID NO 32
<211> LENGTH: 42
<212> TYPE: DNA
<213> ORGANISM: Homo sapiens

<400> SEQUENCE: 32
cggaaaagta gaaacaggag gaatcagttg ccagagtcat aa                 42

<210> SEQ ID NO 33
<211> LENGTH: 738
<212> TYPE: PRT
<213> ORGANISM: Homo sapiens

<400> SEQUENCE: 33

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val

-continued

```
             210                 215                 220
Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
                260                 265                 270

Leu Arg Ser Leu Val Asn Lys Trp Thr Thr Phe Leu Lys Ala Arg Leu
            275                 280                 285

Val Cys Ser Val Thr Asp Glu Asp Gly Pro Glu Thr His Phe Asp Glu
        290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
            355                 360                 365

Arg Ile Pro Tyr Pro Arg Pro Gly Thr Cys Pro Gly Gly Ala Phe Thr
        370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445

Leu Gly Thr Asp Arg Gly Thr Val Gln Lys Val Val Leu Pro Thr
450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
    530                 535                 540

Thr Gly Lys Arg Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Lys Asn Asn Thr Thr Phe Leu Glu Cys
            580                 585                 590

Ala Pro Lys Ser Pro Gln Ala Ser Ile Lys Trp Leu Leu Gln Lys Asp
        595                 600                 605

Lys Asp Arg Arg Lys Glu Val Lys Leu Asn Glu Arg Ile Ile Ala Thr
    610                 615                 620

Ser Gln Gly Leu Leu Ile Arg Ser Val Gln Gly Ser Asp Gln Gly Leu
625                 630                 635                 640
```

```
Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Val Thr Asp
                660                 665                 670

Lys Trp Ser Pro Trp Thr Trp Ala Ser Ser Val Arg Ala Leu Pro Phe
                675                 680                 685

His Pro Lys Asp Ile Met Gly Ala Phe Ser His Ser Glu Met Gln Met
                690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser

<210> SEQ ID NO 34
<211> LENGTH: 13
<212> TYPE: PRT
<213> ORGANISM: Homo sapiens

<400> SEQUENCE: 34

Arg Lys Ser Arg Asn Arg Arg Asn Gln Leu Pro Glu Ser
1               5                   10

<210> SEQ ID NO 35
<211> LENGTH: 738
<212> TYPE: PRT
<213> ORGANISM: Homo sapiens

<400> SEQUENCE: 35

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
                20                  25                  30

Phe Asp Glu Leu Arg Glu Thr Lys Thr Ser Glu Tyr Phe Ser Leu Ser
                35                  40                  45

His His Pro Leu Asp Tyr Arg Ile Leu Leu Met Asp Glu Asp Gln Asp
        50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
                100                 105                 110

Gly Asn Phe Val Arg Val Ile Gln Thr Phe Asn Arg Thr His Leu Tyr
                115                 120                 125

Val Cys Gly Ser Gly Ala Phe Ser Pro Val Cys Thr Tyr Leu Asn Arg
        130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
                180                 185                 190

Gly Thr Asp Ala Ala Ile Phe Arg Ser Leu Thr Lys Arg Asn Ala Val
                195                 200                 205
```

-continued

```
Arg Thr Asp Gln His Asn Ser Lys Trp Leu Ser Glu Pro Met Phe Val
    210                 215                 220
Asp Ala His Val Ile Pro Asp Gly Thr Asp Pro Asn Asp Ala Lys Val
225                 230                 235                 240
Tyr Phe Phe Phe Lys Glu Lys Leu Thr Asp Asn Asn Arg Ser Thr Lys
                245                 250                 255
Gln Ile His Ser Met Ile Ala Arg Ile Cys Pro Asn Asp Thr Gly Gly
            260                 265                 270
Leu Arg Ser Leu Val Asn Lys Trp Thr Thr Phe Leu Lys Ala Arg Leu
        275                 280                 285
Val Cys Ser Val Thr Asp Glu Asp Gly Pro Glu Thr His Phe Asp Glu
290                 295                 300
Leu Glu Asp Val Phe Leu Leu Glu Thr Asp Asn Pro Arg Thr Leu
305                 310                 315                 320
Val Tyr Gly Ile Phe Thr Thr Ser Ser Val Phe Lys Gly Ser Ala
                325                 330                 335
Val Cys Val Tyr His Leu Ser Asp Ile Gln Thr Val Phe Asn Gly Pro
            340                 345                 350
Phe Ala His Lys Glu Gly Pro Asn His Gln Leu Ile Ser Tyr Gln Gly
        355                 360                 365
Arg Ile Pro Tyr Pro Arg Pro Gly Thr Cys Pro Gly Gly Ala Phe Thr
370                 375                 380
Pro Asn Met Arg Thr Thr Lys Glu Phe Pro Asp Asp Val Val Thr Phe
385                 390                 395                 400
Ile Arg Asn His Pro Leu Met Tyr Asn Ser Ile Tyr Pro Ile His Lys
                405                 410                 415
Arg Pro Leu Ile Val Arg Ile Gly Thr Asp Tyr Lys Tyr Thr Lys Ile
            420                 425                 430
Ala Val Asp Arg Val Asn Ala Ala Asp Gly Arg Tyr His Val Leu Phe
        435                 440                 445
Leu Gly Thr Asp Arg Gly Thr Val Gln Lys Val Val Leu Pro Thr
450                 455                 460
Asn Asn Ser Val Ser Gly Glu Leu Ile Leu Glu Glu Leu Glu Val Phe
465                 470                 475                 480
Lys Asn His Ala Pro Ile Thr Thr Met Lys Ile Ser Ser Lys Lys Gln
                485                 490                 495
Gln Leu Tyr Val Ser Ser Asn Glu Gly Val Ser Gln Val Ser Leu His
            500                 505                 510
Arg Cys His Ile Tyr Gly Thr Ala Cys Ala Asp Cys Cys Leu Ala Arg
        515                 520                 525
Asp Pro Tyr Cys Ala Trp Asp Gly His Ser Cys Ser Arg Phe Tyr Pro
530                 535                 540
Thr Gly Lys Arg Lys Ser Lys Lys Gln Asp Val Arg His Gly Asn Pro
545                 550                 555                 560
Leu Thr Gln Cys Arg Gly Phe Asn Leu Lys Ala Tyr Arg Asn Ala Ala
                565                 570                 575
Glu Ile Val Gln Tyr Gly Val Lys Asn Asn Thr Thr Phe Leu Glu Cys
            580                 585                 590
Ala Pro Lys Ser Pro Gln Ala Ser Ile Lys Trp Leu Leu Gln Lys Asp
        595                 600                 605
Lys Asp Arg Arg Lys Glu Val Lys Leu Asn Glu Arg Ile Ile Ala Thr
610                 615                 620
Ser Gln Gly Leu Leu Ile Arg Ser Val Gln Gly Ser Asp Gln Gly Leu
```

```
                         625                 630                 635                 640

Tyr His Cys Ile Ala Thr Glu Asn Ser Phe Lys Gln Thr Ile Ala Lys
                    645                 650                 655

Ile Asn Phe Lys Val Leu Asp Ser Glu Met Val Ala Val Val Thr Asp
                660                 665                 670

Lys Trp Ser Pro Trp Thr Trp Ala Ser Ser Val Arg Ala Leu Pro Phe
            675                 680                 685

His Pro Lys Asp Ile Met Gly Ala Phe Ser His Ser Glu Met Gln Met
        690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser

<210> SEQ ID NO 36
<211> LENGTH: 10
<212> TYPE: PRT
<213> ORGANISM: Homo sapiens

<400> SEQUENCE: 36

Arg Asn Arg Arg Asn Gln Leu Pro Glu Ser
1               5                   10
```

SEMAPHORIN 3C VARIANTS, COMPOSITIONS COMPRISING SAID VARIANTS AND METHODS OF USE THEREOF

CROSS-REFERENCE TO RELATED APPLICATIONS

This application is a National Phase Application of PCT International Application No. PCT/IL2014/050797, International Filing Date Sep. 7, 2014, entitled "SEMAPHORIN 3C VARIANTS, COMPOSITIONS COMPRISING SAID VARIANTS AND METHODS OF USE THEREOF" published on Mar. 12, 2015 as International Publication No. WO 2015/033345, claiming the benefit of U.S Provisional Patent Application No. 61/875,060, filed Sep. 8, 2013, all of which are hereby incorporated herein in their entirety.

FIELD OF THE INVENTION

The present invention relates, inter alia, to variants of Semaphorin 3C (Sema3C) having amino acid modifications at furin-like pro-protein convertase cleavage sites, rendering these sites resistant to cleavage and methods of using same for treatment of cancer.

BACKGROUND OF THE INVENTION

Semaphorins are a family of membrane bound and soluble proteins classified into eight sub-classes based on their structural domains Semaphorins mainly regulate focal adhesion assembly/disassembly and induce cytoskeletal remodeling, thus affecting cell shape, cell attachment to the extracellular matrix, cell motility, and cell migration. Although originally identified as axon guidance factors that control the development of central nervous system, different Semaphorins have been shown to participate in many other processes, such as immune response, angiogenesis and lymphangiogenesis.

The seven class-3 Semaphorins (Sema3s), designated by the letters A-G, are the only vertebrate secreted Semaphorins. Neuropilins (Nrps) and the type A/D family Plexins (Plexin-A1, -A2, and -A3, and Plexin-D1) act as receptors for Sema3s. Each Sema3 family member shows distinct binding preference for Nrps. Each Sema3-Nrp complex associates with specific plexins to mediate downstream signaling.

Semaphorin 3C (Sema3C), a class-3 Semaphorin, is known to affect neuronal migration, such as by providing chemorepulsive cues to sympathetic neurons or chemoattractive cues to GABAergic neurons. In addition to its role as affecting neuronal migration, Sema3C has been shown to have additional functions. As opposed to most class-3 Semaphorins, found to function as inhibitors of endothelial cell migration and proliferation and as inhibitors of angiogenesis (Neufeld et al., 2008, Nat. Rev. Cancer, 8: 632-645), several studies indicate that Sema3C plays a distinct role in promoting angiogenesis, endothelial cell guidance and vascular morphogenesis. For example, Sema3C has been shown to induce proliferation and adhesion of mouse glomerular endothelial cells (MGEC). Additionally, Sema3C has been shown to induce an increase in MGEC directional migration and to stimulate MGEC capillary-like network formation on Collagen I gels (Banu N. et al., 2006, FASEB J., 20:2150-2152).

Sema3C has also been suggested to be involved in tumor progression, to promote tumor migration and to be highly expressed in metastatic tumor cells. For example, Sema3C was shown to be highly expressed in neoplastic cells of gastric cancer. Additionally, primary stomach tumors, as well as metastatic liver tumors, were significantly suppressed by Sema3C miRNA induced silencing in nude mice (Miyato, H. et al., 2012, Cancer Sci., 103: 1961-1966).

The seven class-3 Semaphorins contain conserved furin like pro-protein convertases (FPPC) cleavage sites. The functional activity of class-3 Semaphorins is subject to regulation by cleavage at the FPPC cleavage sites. furin like pro-protein convertases (FPPC) are a family of proteolytic enzymes which convert proteins from their inactive immature form to their active form through cleavage of the immature proteins at FPPC cleavage sites. furin and six other members of this family (PC2, PC1/3, PACE4, PC4, PC5/6, and PC7) possess a strong preference for substrates containing the multi-basic cleavage motif Arg-X-Arg/Lys-Arg-X (Becker et al., 2010, J. Med. Chem., 53(3):1067-1075). furin and its analogues are responsible for the maturation of a large number of inactive protein precursors and are thus involved in many normal physiological processes. Expression of FPPC is often upregulated in tumors and metastases (Seidah N. G. et al., 2012, Nat. Rev. Drug. Discov., 11:367-383).

In some cases, cleavage of class-3 Semaphorins at FPPC cleavage sites was found to result in the complete inhibition of biological activity, as in the case of Sema3B (Varshaysky et al., 2008, Cancer Res., 68:6922-6931). In another case, cleavage at FPPC cleavage sites of Sema3E was found to result in Sema3E's pro-metastatic activity. The proteolytic processing of Sema3E was found to have no role in regulating its inhibitory activity towards endothelial cells (Casazza et al., 2012, EMBO Mol. Med., 4:234-250).

Sema3C comprises conserved FPPC cleavage sites and further comprises a cleavage site for the ADAMTS1 extracellular metalloprotease. Naturally occurring Sema3C is present as a mixture of the FPPC-cleaved and non-cleaved forms. Cleavage of Semaphorin 3C induced by ADAMTS1 has been shown to promote in-vitro cell migration (Esselens C. et al., 2009, J. Biol. Chem., 285: 2463-2473). However, the functional properties of the various FPPC-cleaved and un-cleaved forms of Sema3C have not been characterized.

U.S. Patent Application Publication No. US2013/0028896 discloses methods, uses and pharmaceutical compositions for treatment of prostate cancer using a Sema 3C inhibitor that may be selected may from: an antibody, a Sema 3C peptide, an antisense RNA, a siRNA, a shRNA or a small molecule.

U.S. Patent Application Publication No. US2012/0101029 by some of the inventors of the present invention discloses a method of treating cancer in a subject in need thereof comprising administering to the subject a therapeutically effective amount of a pro-protein convertase resistant Semaphorin 3E.

There still remains, however, an efficient method of suppressing growth of a cancer-induced tumor and/or reducing the occurrence of metastases.

SUMMARY OF THE INVENTION

The present invention relates to variants of Semaphorin 3C (Sema 3C) comprising modifications in furin-like pro-protein convertase (FPPC) cleavage sites, such that the modifications render the sites resistant to cleavage. The invention further relates to methods for treating cancer, such as, but not limited to, breast cancer, lymphoma and head and neck cancer, by administering a composition comprising the Semaphorin 3C variants of the invention to a subject in need thereof. Treating cancer according to the methods or the uses of the invention may include suppressing growth of a tumor and/or reducing occurrence of metastases, such as, but not limited to, metastases in sentinel lymph nodes. Each possibility represents a separate embodiment of the present invention. The present invention further provides, according to some embodiments, methods of inhibiting or suppressing lymphangiogenesis and/or angiogenesis by administering to a subject a composition comprising the Semaphorin 3C variants of the invention and/or wild-type Semaphorin 3C. Each possibility represents a separate embodiment of the present invention.

In an embodiment of the invention, the invention provides Semaphorin 3C variants of the invention and/or wild-type Semaphorin 3C for use in inhibiting or suppressing lymphangiogenesis and/or angiogenesis. The invention further relates to the Semaphorin 3C variants of the invention and/or wild-type Semaphorin 3C for use tin reating cancer, such as, but not limited to, breast cancer, lymphoma and head and neck cancer.

The present invention is based in part on the unexpected discovery that the wild-type Semaphorin 3C, as well as the Sema 3C variants of the invention are able to inhibit in-vitro blood vessel formation and to induce collapse of lymphatic endothelial cells, as exemplified herein below. As exemplified, a truncated form of Semaphorin 3C (Sema3C-p65-FC, as set forth in SEQ ID NO: 6) was not able to induce these effects. The present invention is further based on the surprising discovery that the Semaphorin 3C variants of the invention were able to reduce the size of induced tumors in mice and prevent metastasis in sentinel lymph nodes, as exemplified herein below. Without wishing to be bound by any theory or mechanism, the ability of wild-type Semaphorin 3C and the Semaphorin 3C variants of the invention to inhibit lymphangiogenesis may greatly contribute to their ability to reduce spreading of metastases to lymph nodes, as well as to treat other diseases such as diabetes, IBD and corneal eye diseases.

As used herein, the terms "the Semaphorin 3C variants of the invention", "Semaphorin 3C variants", "the variants of the invention" and "the variants" are used interchangeably. As used herein, the terms "Semaphorin 3C" and "Sema 3C" are used interchangeably.

According to an aspect of the invention "wild-type Semaphorin 3C" encompass also Semaphorin 3C which has at least 80%, 90%, 95%, 99% or 100% sequence identity with the amino acid set forth in SEQ ID NO: 1.

According to one aspect, the present invention provides a variant of Semaphorin 3C which has at least 80%, 90%, 95%, 99% or 100% sequence identity with the amino acid set forth in SEQ ID NO: 1, wherein the variant comprises at least one modification in furin-like pro-protein convertase (FPPC) cleavage site 2 consisting of amino acid residues 549-552; and wherein the modification renders the variant resistant to cleavage at the cleavage site 2.

According to another aspect, there is provided a variant of Semaphorin 3C which has at least 80%, 90%, 95%, 99% or 100% sequence identity with the amino acid set forth in SEQ ID NO: 1, wherein the variant has at least one modification in furin-like pro-protein convertase cleavage site 3 consisting of amino acid residues 742-745; and wherein the modification renders said variant resistant to cleavage at the cleavage site 3.

According to another aspect, the present invention provides a variant of Semaphorin 3C Semaphorin 3C which has at least 80%, 90%, 95%, 99% or 100% sequence identity with the amino acid set forth in SEQ ID NO: 1, wherein the variant comprises at least one modification in furin-like pro-protein convertase (FPPC) cleavage site 2 consisting of amino acid residues 549-552 and at least one modification in furin-like pro-protein convertase cleavage site 3 consisting of amino acid residues 742-745; and wherein the modifications render the variant resistant to cleavage at the cleavage site 2 and at the cleavage site 3.

According to one aspect, the present invention provides a variant of Semaphorin 3C as set forth in SEQ ID NO: 1, wherein the variant (also termed herein "the variant of the invention") comprises at least one modification in furin-like pro-protein convertase (FPPC) cleavage site 2 consisting of amino acid residues 549-552; and wherein the modification renders said variant resistant to cleavage at said cleavage site 2.

According to some embodiments, a modification which renders an FPPC cleavage site resistant to cleavage prevents cleavage of at least 80% of Sema3C variants harboring the modification, possibly at least 90% of said variants, alternatively at least 95% of said variants as compared to cleavage of wild-type Sema3C. Each possibility represents a separate embodiment of the present invention. As used herein, the phrases "a modification which renders a variant resistant to cleavage" and "a modification which prevents a variant from being cleaved" are used interchangeably. As used herein, an un-cleavable variant refers to a variant resistant to cleavage at a furin-like pro-protein convertase cleavage site. According to some embodiments, a Sema3C variant which is un-cleavable due to a modification rendering an FPPC cleavage site resistant to cleavage retains residual cleavage. According to some embodiments, residual cleavage is cleavage of the variant of the invention to a degree of up to 30%, possibly up to 20%, possibly up to 10%, alternatively up to 5% of as compared to the cleavage of wild-type Sema3C. Each possibility represents a separate embodiment of the present invention. According to some embodiments, residual cleavage is cleavage of less than 50%, possibly less than 40%, alternatively less than 30%, typically less than 20% of the variant of the invention. Each possibility represents a separate embodiment of the present invention. According to some embodiments, the variant of the invention comprises at least one modification in furin-like pro-protein convertase cleavage site 3 consisting of amino acid residues 742-745 of Sema3C as set forth in SEQ ID NO: 1; wherein the modification renders the variant resistant to cleavage at the cleavage site.

According to some embodiments, the modification is selected from the group consisting of: at least one amino-acid substitution, at least one amino-acid deletion and a combination thereof. Each possibility represents a separate embodiment of the present invention. According to some embodiments, the modification is an amino-acid deletion comprising at least part of the amino acids within the furin-like pro-protein convertase cleavage site. According to some embodiments, the modification is a modification of at least one Arginine residue within a furin-like pro-protein convertase cleavage site. According to some embodiments, the modification is a modification of at least one Arginine residue within a furin-like pro-protein convertase cleavage site to a Lysine residue. According to other embodiments, the modification is a modification of all Arginine residues within a furin-like pro-protein convertase cleavage site.

According to some embodiments, the variant of the invention comprises at least one modification in furin-like pro-protein convertase cleavage site 2 consisting of amino acid residues 549-552 of Sema3C as set forth in SEQ ID NO: 1 and at least one modification in furin-like pro-protein convertase cleavage site 3 consisting of amino acid residues 742-745 of Sema3C as set forth in SEQ ID NO: 1; wherein the modifications render the variant resistant to cleavage at the cleavage sites. According to some embodiments, the at least one modification in cleavage site 2 is a modification from the sequence RSRR as set forth in SEQ ID NO: 3 to the sequence KSKK as set forth in SEQ ID NO: 13. According to some embodiments, the at least one modification in cleavage site 3 is a truncation of at least part of the C-terminus of said variant as set forth in SEQ ID NO: 34. According to some embodiments, the at least one modification in cleavage site 3 is a truncation of the entire C-terminus of said variant as set forth in SEQ ID NO: 34. According to some embodiments, the variant of the invention is a variant of Semaphorin 3C as set forth in SEQ ID NO: 1, wherein the variant comprises a modification at furin-like pro-protein convertase (FPPC) cleavage site 2 as set forth in SEQ ID NO: 13 and a truncation of the C-terminus section of said variant as set forth in SEQ ID NO: 34. According to some embodiments, the variant of the invention further comprises at least one modification in a basic domain of said variant, the basic domain having an amino acid sequence as set forth in SEQ ID NO: 5. As used herein, the basic domain of Sema3C as set forth in SEQ ID NO: 5 consists of amino acids 724-745 of Sema3C as set forth in SEQ ID NO: 1.

According to some embodiments, the variant of the invention comprises at least one modification in furin-like pro-protein convertase cleavage site 2 consisting of amino acid residues 549-552 of Sema3C as set forth in SEQ ID NO: 1 or has at least 80%, preferably at least 90%, more preferably at least 95%, even more preferably at least 99% sequence identity) with the amino acid set forth in SEQ ID NO: 1, and at least one modification in furin-like pro-protein convertase cleavage site 3 consisting of amino acid residues 742-745 of Sema3C as set forth in SEQ ID NO: 1; wherein the modifications render the variant resistant to cleavage at the cleavage sites. According to some embodiments, the at least one modification in cleavage site 2 is a modification from the sequence RSRR as set forth in SEQ ID NO: 3 to the sequence KSKK as set forth in SEQ ID NO: 13. According to some embodiments, the at least one modification in cleavage site 3 is a truncation of at least part of the C-terminus of said variant as set forth in SEQ ID NO: 34. According to some embodiments, the at least one modification in cleavage site 3 is a truncation of the entire C-terminus of said variant as set forth in SEQ ID NO: 34. According to some embodiments, the variant of the invention is a variant of Semaphorin 3C as set forth in SEQ ID NO: 1, wherein the variant comprises a modification at furin-like pro-protein convertase (FPPC) cleavage site 2 as set forth in SEQ ID NO: 13 and a truncation of the C-terminus section of said variant as set forth in SEQ ID NO: 34. According to some embodiments, the variant of the invention further comprises at least one modification in a basic domain of said variant, the basic domain having an amino acid sequence as set forth in SEQ ID NO: 5. As used herein, the basic domain of Sema3C as set forth in SEQ ID NO: 5 consists of amino acids 724-745 of Sema3C as set forth in SEQ ID NO: 1.

According to some embodiments, the modification renders the variant of the invention resistant to cleavage by members of the furin-like pro-protein convertases. According to some embodiments, the members of the furin-like pro-protein convertases are selected from the group consisting of: furin, PC 1/3, PC2, PC4, PC 5/6, PACE4, PC7, Site-1 Protease, NARC-1 and a combination thereof. Each possibility represents a separate embodiment of the present invention.

According to some embodiments, the present invention provides a polynucleotide comprising cDNA corresponding to the variant of the invention. According to some embodiments, the present invention provides a polynucleotide encoding cDNA corresponding to the variant of the invention.

According to another aspect, the present invention provides a pharmaceutical composition comprising at least one variant of Semaphorin 3C as set forth in SEQ ID NO: 1, the variant comprising at least one modification in furin-like pro-protein convertase (FPPC) cleavage site 2 consisting of amino acid residues 549-552; and wherein the modification renders said variant resistant to cleavage at said cleavage site.

According to some embodiments, the present invention provides a pharmaceutical composition (also termed herein "the pharmaceutical composition of the invention") comprising at least one variant of the variants of the invention. According to some embodiments, the present invention provides the pharmaceutical composition comprising an effective amount of the variant of Semaphorin 3C or the wild type Semaphorin 3C of the invention for treating cancer in a subject.

According to some embodiments, the present invention provides a pharmaceutical composition comprising at least one variant of Semaphorin 3C as set forth in SEQ ID NO: 1, the variant comprising at least one modification in furin-like pro-protein convertase (FPPC) cleavage site 2 consisting of amino acid residues 549-552 and wherein the modification renders said variant resistant to cleavage at said cleavage site, for treating cancer in a subject.

According to another aspect, the present invention provides a method for treating cancer in a subject in need thereof, the method comprising administering the pharmaceutical composition of the invention to the subject.

According to some embodiments, the present invention provides a method for treating cancer in a subject, the method comprising administering to the subject a pharmaceutical composition comprising at least one variant of Semaphorin 3C as set forth in SEQ ID NO: 1, the variant comprising at least one modification in furin-like pro-protein convertase (FPPC) cleavage site 2 consisting of amino acid residues 549-552 and wherein the modification renders said variant resistant to cleavage at said cleavage site.

According to some embodiments, the present invention provides a pharmaceutical composition comprising an effective amount of at least one variant of Semaphorin 3C as set forth in SEQ ID NO: 1, the variant comprising at least one modification in furin-like pro-protein convertase (FPPC) cleavage site 2 consisting of amino acid residues 549-552 and wherein the modification renders said variant resistant to cleavage at said cleavage site for use for treating cancer.

According to some embodiments, treating is selected from the group consisting of: suppressing growth of a tumor, reducing occurrence of metastases and a combination thereof. Each possibility represents a separate embodiment of the present invention. According to some embodiments, the metastases are metastases in lymph nodes of said subject. According to some embodiments, the lymph nodes are sentinel lymph nodes. As used herein, the term "sentinel lymph nodes" refers to lymph nodes draining a cancer tumor.

According to some embodiments, the cancer is selected from the group consisting of: lymphoma, breast cancer, head and neck cancer, lung cancer, rectal cancer, bile duct cancer, bladder cancer, bone cancer, colon cancer, brain cancer, cervical cancer, ocular melanoma, Kaposi's sarcoma, leukemia, melanoma, myeloma, ovarian cancer, vaginal cancer, prostate cancer, testicular cancer, endometrial cancer, thyroid cancer and thymus cancer. Each possibility represents a separate embodiment of the present invention. According to some embodiments, the cancer is selected from lymphoma, breast cancer and head and neck cancer. Each possibility represents a separate embodiment of the present invention. According to some embodiments, the cancer is breast cancer.

According to some embodiments, administration to the subject is by a route selected from the group consisting of: intravenous, intraarterial, transdermal, subcutaneous, via direct injection into a tissue and via direct injection into a tumor. Each possibility represents a separate embodiment of the present invention.

According to another aspect, the present invention provides a pharmaceutical composition comprising as an active ingredient a therapeutically effective amount of wild-type Semaphorin 3C as set forth in SEQ ID NO: 1.

According to another aspect, the present invention provides a method for inhibiting lymphangiogenesis in a subject, the method comprising administering the pharmaceutical composition of the invention to the subject. According to some embodiments, the present invention provides a method for inhibiting lymphangiogenesis in a subject, the method comprising administering to the subject a pharmaceutical composition comprising at least one variant of Semaphorin 3C as set forth in SEQ ID NO: 1, the variant comprising at least one modification in furin-like pro-protein convertase (FPPC) cleavage site 2 consisting of amino acid residues 549-552; and wherein the modification renders said variant resistant to cleavage at said cleavage site.

According to some embodiments, the present invention provides a method for inhibiting lymphangiogenesis in a subject, the method comprising administering to the subject a pharmaceutical composition comprising as an active ingredient a therapeutically effective amount of wild-type Semaphorin 3C as set forth in SEQ ID NO: 1.

According to some embodiments, the present invention provides the pharmaceutical composition of the invention for inhibiting lymphangiogenesis in a subject. According to some embodiments, the present invention provides a pharmaceutical composition comprising as an active ingredient a therapeutically effective amount of wild-type Semaphorin 3C as set forth in SEQ ID NO: 1 for inhibiting lymphangiogenesis in a subject.

According to another aspect, the present invention provides a method for inhibiting angiogenesis in a subject, the method comprising administering the pharmaceutical composition of the invention to the subject. According to some embodiments, the present invention provides a method for inhibiting angiogenesis in a subject, the method comprising administering to the subject a pharmaceutical composition comprising at least one variant of Semaphorin 3C as set forth in SEQ ID NO: 1, the variant comprising at least one modification in furin-like pro-protein convertase (FPPC) cleavage site 2 consisting of amino acid residues 549-552; and wherein the modification renders said variant resistant to cleavage at said cleavage site.

According to some embodiments, the present invention provides a method for inhibiting angiogenesis in a subject, the method comprising administering to the subject a pharmaceutical composition comprising as an active ingredient a therapeutically effective amount of wild-type Semaphorin 3C as set forth in SEQ ID NO: 1.

According to some embodiments, the present invention provides the pharmaceutical composition of the invention for inhibiting angiogenesis in a subject. According to some embodiments, the present invention provides a pharmaceutical composition comprising as an active ingredient a therapeutically effective amount of wild-type Semaphorin 3C as set forth in SEQ ID NO: 1 for inhibiting angiogenesis in a subject.

According to some embodiments, the present invention provides the pharmaceutical composition of the invention for inhibiting lymphangiogenesis in a subject. According to some embodiments, the present invention provides a pharmaceutical composition comprising as an active ingredient a therapeutically effective amount of wild-type Semaphorin 3C as set forth in SEQ ID NO: 1 for inhibiting lymphangiogenesis in a subject.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 1A-B depict (A) a schematic representation of wild-type Sema3C (marked "Sema3C") and an un-cleavable variant of Sema3C, termed UNCL-Sema3C/FC (marked "UNCL-Sema3C/FC"), as described in Example 1 herein below (BD=Basic Domain; 1, 2, 3=FPPC cleavage sites 1, 2 and 3, respectively; Fc=FC tag), and (B) a western-blot analysis, using an anti-FC antibody, analyzing conditioned media from HEK293 cells transfected with either an empty expression vector (NC), a construct encoding FC-tagged wild type Sema3C (Sema3C-wt) or a construct encoding UNCL-Sema3C/FC (UNCL-Sema3C).

4E-F, termed "Sema3C-p65-FC") at the beginning of the incubation (Time zero) and 1 hour following incubation.

FIGS. 5A-M show micrographs (A-L) and a bar graph (M). FIGS. 5A-L depict micrographs of isolated sentinel lymph nodes which were adjacent to LM2-4 cells-induced tumors in mice visualized using phase contrast (A-D, I-J, marked "phase contrast") or fluorescent microscope detecting tomato-red fluorescence (E-H, K-L, marked "tomato-red fluorescence"). FIGS. 5A-H show lymph nodes extracted from mice in which tumors were induced by LM2-4 cells. FIGS. 5I-L show lymph nodes extracted from mice in which tumors were induced by LM2-4 cells expressing the uncleavable UNCL-Sema3C/myc-His construct, as described in Example 1. FIG. 5M shows a bar graph comparing tumor weights of tumors extracted from mice injected with LM2-4 cells (marked "control") or LM2-4 cells expressing the uncleavable UNCL-Sema3C/myc-His construct, as described in Example 1 (marked "Sema3C").

Figure 6:
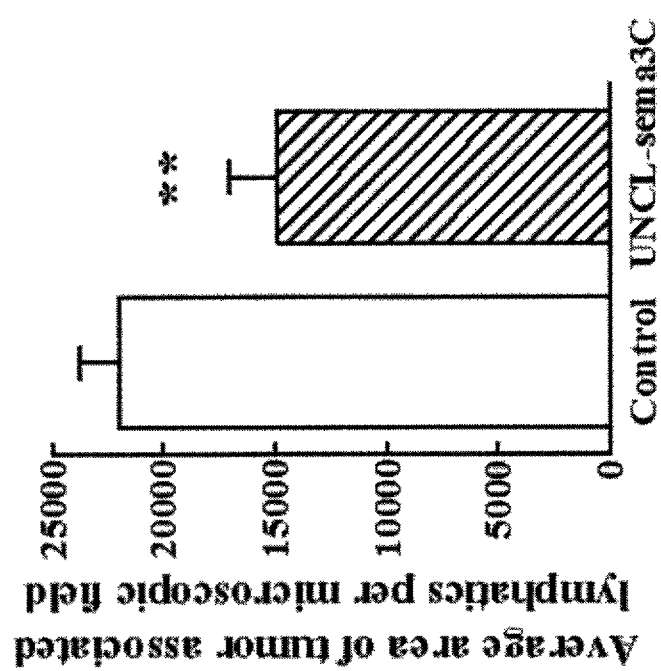

FIG. 6 shows a bar graph comparing the density of tumor associated lymph vessels in sections of tumors extracted from mice injected with LM2-4 cells (marked "control") or LM2-4 cells expressing the uncleavable UNCL-Sema3C/myc-His construct, as described in Example 1 (marked "UNCL-Sema3C").

Figure 7:
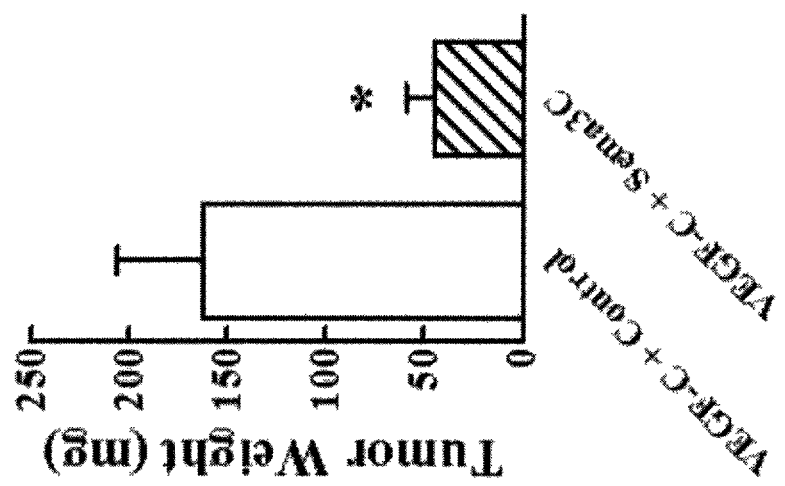

FIG. 7 shows a bar graph comparing tumor weights of tumors extracted from mice injected with MDA-MB-231 cells expressing human VEGF-C (marked "VEGFC+Control") or MDA-MB-231 cells expressing human VEGF-C and the uncleavable UNCL-Sema3C/myc-His construct, as described in Example 1 (marked "VEGF-C+Sema3C").

Figure 8:
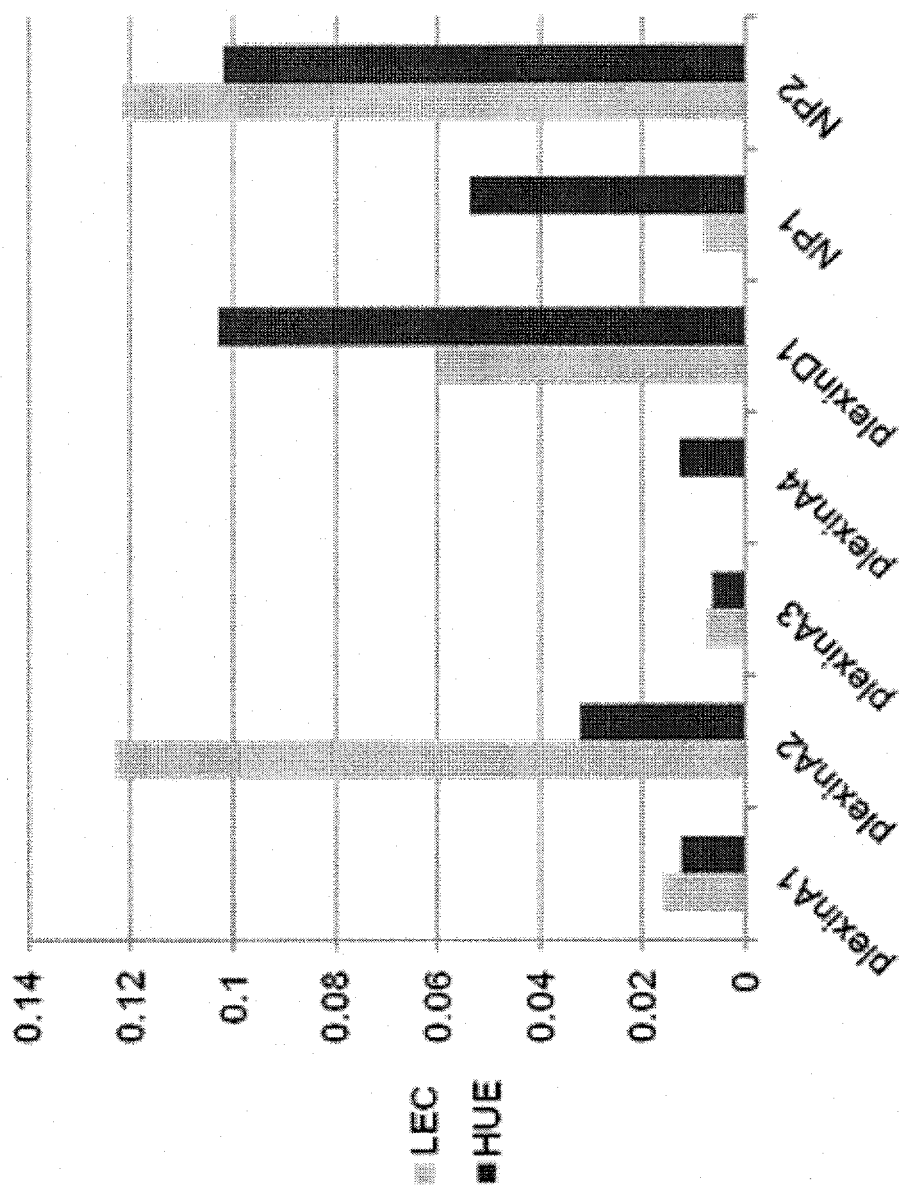

FIG. 8 shows a bar graph comparing real-time PCR quantification of expression for PlexinA1, PlexinA2, PlexinA3, PlexinA4, Plexin D1, NP1 and NP2 in cultured Lymphatic Endothelial Cells (marked "LEC") versus cultured Human Umbilical Vein-derived Endothelial Cells (marked "HUE").

FIGS. 9A-D show micrographs depicting Lymphatic Endothelial Cells (LEC) which were incubated with either elution buffer (A), UNCL-Sema3C-FC (B), Semaphorin 3E-FC (C) or Sema3C-p65-FC (D). The cells were stained with Phalloidin and an anti-Vinculin antibody and visualized using a fluorescent microscope (magnification: ×40).

FIGS. 10 A-F show micrographs and graphs depicting HUVEC or LEC cells. A: HUVEC or LEC were seeded in 12 well dishes ($2\times10^4$ and $5\times10^4$ cells/well respectively) in LEC growth medium in the presence of vehicle (control) or FR-sema3C/Fc (2 µg/ml). Cells were photographed after 72 h. B. LEC and HUVEC were seeded in fibronectin coated 96 well dishes and the effect of FR-sema3C/Fc (2 µg/ml) on their proliferation was measured using the WST-1 proliferation assay kit. Shown is the average of N independent experiments. C. Confluent 6 well dishes containing LEC were incubated with vehicle or FR-Sema3C-Fc and stimulated with VEGF-C. Cell extracts were then subjected to western blot analysis using antibodies directed against phosphorylated VEGFR-3, phosphorylated-ERK1/2 and phosphorylated AKT. The blots were then stripped and re-probed with antibodies against VEGFR-3, ERK1/2 and AKT. Shown is a representative experiment out of several that were performed with similar results F. LEC silenced for the expression of the indicated receptors or control cells expressing a non-targeting shRNA (sh-control) were seeded in wells of the xCELLigence machine ($2\times10^4$ cells/well) and cultured for 24 h. They were subsequently stimulated with FR-sema3C/Fc (1 µg/ml). Cell contraction over time was then measured. Maximal contraction was determined as described in FIG. 10E. *** indicate $P<0.001$. D. The expression of the indicated receptors was silenced in LEC using lentiviral vectors encoding appropriate shRNA species. Total RNA was prepared from cells infected with a non-targeting sh-RNA (Sh-Control) or from cells in which the expression of the indicated receptors was silenced. Quantitative reverse PCR was used to determine the degree of silencing. E. Cells were seeded in wells of an E-plate 24 h prior to the experiment. In this example the cells were then stimulated with FR-sema3C/Fc (1 µg/ml) or with vehicle (Control). The difference between the response to the vehicle and FR-sema3C/Fc was defined as the maximal contraction and as shown by the double headed arrow.

FIGS. 11 A-E show micrographs and graphs showing that FR-sema3C/myc does not affect cultured LM2-4 cells: A. Conditioned medium from LM2-4 cells expressing tomato red RFP and either empty vector (control) or a FR-Sema3C/myc encoding lentiviral vector was subjected to western blot analysis using anti-myc antibodies. B. HUVEC and LM2-4 were seeded in gelatin coated 12 well plates ($10^4$ cells/well). After 24 hours the medium was exchanged with conditioned media from LM2-4 cells infected with empty lentiviruses (control) or with conditioned medium from FR-sema3C/myc expressing LM2-4 cells and cell contraction assayed (mag. ×10). C. LM2-4 cells infected with FR-Sema3C/myc or with empty (Control) lentiviral vectors were seeded in 24 well dishes ($1\times10^5$ cells/well). The number of adherent cells after seeding (Day 0) or after 3 days was determined using a coulter-counter. Error bars represent the standard error of the mean derived from three independent experiments. D. The migration of LM2-4 cells infected with empty lentiviral vector (control) or with lentiviruses directing expression of FR-sema3C/myc was measured using the xCELLigence machine. E. The expression of the neuropilin-1 (NP1), neuropilin-2 (NP2) and plexin-D1 was examined in the indicated cell types using western blot analysis.

Figure 12F:
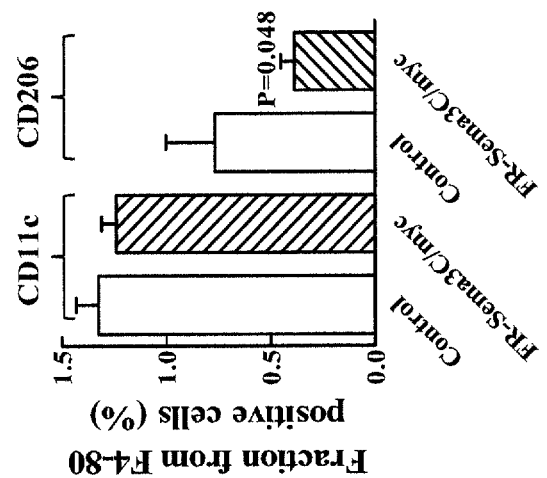

FIGS. 12 A-G show micrographs and graphs demonstrating that FR-sema3C inhibits tumor development, tumor angiogenesis and tumor lymphangiogenesis: A. LM2-4 cells expressing tomato red RFP and either empty vector (control) or a FR-Sema3C/myc encoding lentiviral vector ($2\times106$ cells in 50 µl PBS) were implanted in mammary fat pads of scid/nod mice. Tumors were excised after 30 days. Shown are the average tumor weights from N tumors obtained from three independent experiments. B. Representative paraffin section stained with hematoxilin and an antibody directed against LYVE-1. Arrows indicate intra-tumoral lymph vessels. C. The entire cross-section derived from each tumor was scanned and photographed. The ratio between the average area of LYVE-1 staining and the average area of the tumor sections (derived from N tumors) was determined using ImagePro. D. Representative paraffin section from a control tumor stained with hematoxilin and an antibody directed against CD31. Intra-tumoral blood vessels are indicated (arrows). E. The ratio between the average area of CD31 staining per tumor section from control and FR-sema3C/myc expressing tumors was determined as described under C. F. Single cell suspensions were prepared from control and FR-sema3C/myc expressing tumors. Cells were then incubated with antibodies directed against CD31. Flow cytometry was performed and results analyzed and quantified with Summit Version 4.3. Shown is the percentage of CD31 positive cells out of the total cell population of the tumor. G. The single cell suspensions described under C were incubated with antibodies directed against F4-80, CD11c and CD206. Flow cytometry was performed and results analyzed and quantified with Summit Version 4.3. The percentage of CD11c positive cells and CD206 positive cells out of the total F4-80 positive cells is shown. Error bars represent the standard error of the mean between different tumors.

FIGS. 13 A-D show that FR-sema3C inhibit the spontaneous metastasis of LM2-4 cells to lymph nodes: A. LM2-4 cells expressing tomato red RFP and either empty vector (control) or a FR-Sema3C/myc encoding lentiviral vector were implanted in mammary fat pads. The proper axillary, lumbar aortic, and subiliac lymph nodes were excised after 30 days. The size of metastases in excised lymph nodes was quantified using the IVIS-200 imaging system. Lymph nodes containing metastases (yellow arrows) or not (green arrows) are shown. B. A representative histological section derived from a metastase containing lymph node derived from a mouse harboring a control tumor is shown at two different magnifications (a: 10× and b: 40×). Also shown is a histological sections from a clean lymph node from a mouse harboring a tumor containing FR-sema3C/myc expressing LM2-4 cells (c: ×10 and d: ×40). The sections were stained with Anti human-HLA-1 antibodies and counterstained with hematoxilin. C. The percentage of mice containing detectable metastases in their lymph nodes in two independent experiments is depicted. D. The relative concentration of tomato red expressing LM2-4 cells in lymph nodes containing metastases was determined using the IVIS-200 system by measurement of the normalized photon density (photon/sec/cm2/sr) emitted.

DETAILED DESCRIPTION OF THE INVENTION

The present invention provides, for the first time, variants of Semaphorin 3C (Sema 3C) having modifications in furin-like pro-protein convertase (FPPC) cleavage sites, such that the modifications render the sites resistant to cleavage. Unexpectedly, the un-cleavable Sema 3C variants were found to suppress growth of a breast-cancer-induced tumor and to prevent the spreading of metastases to sentinel lymph nodes surrounding the tumor. Surprisingly, the Sema 3C variants were further found to reduce the formation of tumor associated lymph vessels.

As used herein, the terms "Semaphorin 3C" and "Sema 3C" are used interchangeably and refer to human Semaphorin 3C as set forth in SEQ ID NO: 1. The polynucleotide sequence encoding Sema3C (as set forth in SEQ ID NO: 1) is set forth in SEQ ID NO: 15. Human Semaphorin 3C, as set forth in SEQ ID NO: 1, comprises three furin-like pro-protein convertase (FPPC) cleavage sites, referred to herein as site 1, site 2 and site 3:

1. As used herein, the terms "site 1", "cleavage site 1" and "furin-like pro-protein convertase cleavage site 1" are used interchangeably and refer to a site having SEQ ID NO: 2, consisting of amino acids 144-147 of SEQ ID NO: 1;
2. As used herein, the terms "site 2", "cleavage site 2" and "furin-like pro-protein convertase cleavage site 2" are used interchangeably and refer to a site having SEQ ID NO: 3, consisting of amino acids 549-552 of SEQ ID NO: 1; and
3. As used herein, the terms "site 3", "cleavage site 3" and "furin-like pro-protein convertase cleavage site 3" are used interchangeably and refer to a site having SEQ ID NO: 4, consisting of amino acids 742-745 of SEQ ID NO: 1 within the basic domain of Sema 3C.

As used herein, the basic domain of Sema 3C (referred to herein also as "the basic domain"), as set forth in SEQ ID NO: 5, consists of amino acids 724-745 of SEQ ID NO: 1.

According to some embodiments, the FPPC cleavage sites are cleavable by furin-like pro-protein convertases. According to some embodiments, furin-like pro-protein convertases (FPPCs) able to cleave the FPPC cleavage sites according to the present invention are selected from the group consisting of: furin, PC 1/3, PC2, PC4, PC 5/6, PACE4, PC7, Site-1 Protease, NARC-1 and a combination thereof. Each possibility represents a separate embodiment of the present invention.

Naturally occurring Sema3C is present as a mixture of the FPPC-cleaved and non-cleaved forms. As exemplified herein below, Sema 3C cleaved at site 2 is unable to induce contraction of Vascular Endothelial Cells (VECs) and/or Lymphatic Endothelial Cells (LECs). According to some embodiments, Sema 3C cleaved at site 2 does not possess anti-angiogenic properties and/or anti-lymphangiogenic properties. Each possibility represents a separate embodiment of the present invention. Without wishing to be bound by any theory or mechanism, cleavage of Sema 3C at FPPC cleavage site 2 by FPPCs secreted by cells, such as malignant tumour cells, results in loss or decrease of anti-angiogenic and/or anti-lymphangiogenic properties possessed by un-cleavable Sema 3C variants. It is therefore contemplated, in a non-limiting manner, that the ability of naturally occurring Sema3C (referred to herein also as wild-type Sema3C) to inhibit angiogenic and lymphangiogenic properties is attributed to the non-cleaved form of Sema3C. According to some embodiments, the N-terminal part of Sema 3C which has undergone at site 2 is termed Sema 3C-p65, as set forth in SEQ ID NO: 6. It is to be understood that variants of Sema3C which are cleaved at site 2, such as Sema3C-p65, are not included in the variants of the invention.

According to one aspect, the present invention provides a variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site.

The term "variant" as used herein refers to a polypeptide sequence that possesses some modified structural property of the native Sema3C either as set forth in SEQ ID NO: 1 or which has at least 80%, 90%, 95% or 99% sequence identity) with the amino acid set forth in SEQ ID NO: 1.

According to some embodiments, the term "variant" as used herein refers to native Sema3C as set forth in SEQ ID NO: 1 which possesses at least one modification in FPPC site 2 which renders the variant resistant to cleavage. As used herein, the terms "polypeptide" and "protein" are used interchangeably and refer to a polymer of amino acid residues.

According to some embodiments, the variant of the invention comprises at least one modification in furin-like pro-protein convertase cleavage site 2 consisting of amino acid residues 549-552 of Sema3C as set forth in SEQ ID NO: 1; wherein the modification prevents the variant from being cleaved at cleavage site 2. According to some embodiments, the variant of the invention comprises at least one modification in furin-like pro-protein convertase cleavage site 2 consisting of amino acid residues 549-552 of Sema3C as set forth in SEQ ID NO: 1; wherein the modification prevents the variant from being cleaved at cleavage site 2 by furin-like pro-protein convertases (FPPCs).

According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to RSKR (as set forth in SEQ ID NO: 11), preferably to KSKR (as set forth in SEQ ID NO: 12), most preferably to KSKK (as set forth in SEQ ID NO: 13). Each possibility represents a separate embodiment of the present invention. According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13). According to some embodiments, the variant of the invention comprises a deletion of at least part of furin-like pro-protein convertase cleavage site 2 consisting of amino acid residues 549-552 of Sema3C as set forth in SEQ ID NO: 1.

According to some embodiments, the variant of the invention comprises at least one modification in furin-like pro-protein convertase cleavage site 3 consisting of amino acid residues 742-745 of Sema3C as set forth in SEQ ID NO: 1; wherein the modification renders the variant resistant to cleavage at cleavage site 3. According to some embodiments, the variant of the invention comprises at least one modification in furin-like pro-protein convertase cleavage site 3 consisting of amino acid residues 742-745 of Sema3C as set forth in SEQ ID NO: 1; wherein the modification prevents the variant from being cleaved at cleavage site 3 by furin-like pro-protein convertases (FPPCs). According to some embodiments, a modification in furin-like pro-protein convertase cleavage site 3 of Sema3C as set forth in SEQ ID NO: 1, preventing cleavage at site 3, is a modification selected from the group consisting of: at least one amino-acid substitution within site 3, at least one amino-acid deletion within site 3 and a combination thereof. Each possibility represents a separate embodiment of the present invention.

According to some embodiments, the variant of the invention comprises a deletion of at least part of furin-like pro-protein convertase cleavage site 3 consisting of amino acid residues 742-745 of Sema3C as set forth in SEQ ID NO: 1. According to some embodiments, the variant of the invention comprises a deletion of furin-like pro-protein convertase cleavage site 3 consisting of amino acid residues 742-745 of Sema3C as set forth in SEQ ID NO: 1.

According to some embodiments, the variant of the invention comprises a truncation of at least part of the C-terminus of Sema3C as set forth in SEQ ID NO: 34. According to some embodiments, the variant of the invention comprises a truncation of at least part of the C-terminus of Sema3C from FPPC cleavage site 3 and downstream, as set forth in SEQ ID NO: 36. According to some embodiments, the variant of the invention comprises a truncation of the C-terminus of Sema3C as set forth in SEQ ID NO: 34. According to some embodiments, the variant of the invention comprises a truncation of the C-terminus of Sema3C from FPPC cleavage site 3 and downstream, as set forth in SEQ ID NO: 36. According to some embodiments, a truncation of the C-terminus of Sema3C as set forth in SEQ ID NO: 34 comprises FPPC site 3. According to some embodiments, a truncation of the C-terminus of Sema3C as set forth in SEQ ID NO: 36 comprises FPPC site 3. According to some embodiments, the variant of the invention comprises a truncation of at least part of the C-terminus of said variant, such that at least FPPC cleavage site 3 is truncated.

According to some embodiments, a variant according to the invention is a variant of Sema3C as set forth in SEQ ID NO: 1, the variant comprising a truncation of part of the basic domain such that furin-like pro-protein convertase cleavage site 3 is deleted. According to some embodiments, the variant of the invention in which the C-terminus as set forth in SEQ ID NO: 34 is truncated, is missing both furin-like pro-protein convertase cleavage site 3 and the ADAMTS1 cleavage site.

It is to be understood that the exact amino-acid sequence of the ADAMTS1 cleavage site in Sema3C is unknown, although it is believed to be within the 13 C-terminal amino acids as set forth in SEQ ID NO: 34 (Esselens C. et al., 2009, J. Biol. Chem., 285: 2463-2473). According to some embodiments, the variant of the invention comprises at least one modification of the ADAMTS1 cleavage site. According to some embodiments, the variant of the invention comprises at least one modification of the ADAMTS1 cleavage site rendering the site non-cleavable. According to some embodiments, the variant of the invention comprises at least one modification of the ADAMTS1 cleavage site rendering the site non-cleavable by members of the ADAMTS extracellular metalloproteases. According to some embodiments, the variant of the invention comprises a deletion of at least part of the ADAMTS1 cleavage site. According to some embodiments, the variant of the invention comprises a deletion of the ADAMTS1 cleavage site.

According to some embodiments, the variant of the invention comprises at least one modification in furin-like pro-protein convertase cleavage site 2 consisting of amino acid residues 549-552 of Sema3C as set forth in SEQ ID NO: 1, and at least one modification in furin-like pro-protein convertase cleavage site 3 consisting of amino acid residues 742-745 of Sema3C as set forth in SEQ ID NO: 1; wherein the modifications render the variant resistant to cleavage at the cleavage sites.

According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of the amino acid sequence set forth in SEQ ID NO: 34. According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of at least part of the amino acid sequence set forth in SEQ ID NO: 34. According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of the amino acid sequence set forth in SEQ ID NO: 34; wherein said variant is as set forth in SEQ ID NO: 35.

According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of the amino acid sequence set forth in SEQ ID NO: 36. According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of at least part of the amino acid sequence set forth in SEQ ID NO: 36.

According to some embodiments, a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of the amino acid sequence set forth in SEQ ID NO: 34 is referred to herein as "UNCL-Sema3C" also termed here "FR-Sema3C". According to some embodiments, UNCL-Sema3C comprises a C-terminal tag. According to some embodiments, UNCL-Sema3C comprises a C-terminal FC-tag, having a sequence as set forth in SEQ ID NO: 8. According to some embodiments, UNCL-Sema3C comprises a C-terminal myc-6His tag, having a sequence as set forth in SEQ ID NO: 9.

Bioactivity of Sema 3C variants, as used herein, refers to the ability of Sema3C variants to elicit at least one of Sema 3C's biological responses, such as, but not limited to, the ability to inhibit cell migration or the ability to induce collapse of cellular cytoskeleton in HUVECs. According to some embodiments, the variants of the invention are bioactive. The bioactivity of Sema 3C variants may be assayed by any method known in the art, such as, but not limited to, induction of HUVEC contraction, cell migration assays, immune-staining of cells for cytoskeletal markers and the like.

According to some embodiments, modification in an FPPC cleavage site according to the present invention is a modification which renders said site resistant to cleavage. According to some embodiments, modification in an FPPC cleavage site according to the present invention is a modification which renders said site resistant to cleavage by furin-like pro-protein convertases (FPPCs).

According to some embodiments, a modification according to the invention is selected from the group consisting of: at least one amino-acid substitution, at least one amino-acid deletion and a combination thereof. Each possibility represents a separate embodiment of the present invention. According to some embodiments, a modification according to the invention is at least one amino-acid substitution. According to some embodiments, a modification according to the invention is at least one amino-acid deletion. According to some embodiments, a modification according to the invention is a modification which prevents cleavage at a furin-like pro-protein convertase cleavage site. According to some embodiments, the modification is an amino acid deletion comprising at least part of the amino acids of an FPPC cleavage site. According to some embodiments, the modification is a truncation comprising at least part of the amino acids of the FPPC cleavage site.

According to some embodiments, a modification according to the invention is an amino acid truncation. According to some embodiments, a modification of furin-like pro-protein convertase cleavage site 3 which renders this site non-cleavable is a truncation of at least part of the basic domain as set forth in SEQ ID NO: 5. According to some embodiments, the variant of the invention comprises a truncation of at least part of the basic domain of Sema3C as set forth in SEQ ID NO: 5. According to some embodiments, the Sema3C variant of the invention comprises a complete truncation of the basic domain. According to some embodiments, the variant of the invention comprises at least one modification in the basic domain of Sema3C as set forth in SEQ ID NO: 5.

According to some embodiments, a modification of furin-like pro-protein convertase cleavage site 3 which renders this site non-cleavable is a truncation of at least part of the C-terminus of Sema3C, the C-terminus set forth in SEQ ID NO: 34. According to some embodiments, the variant of the invention comprises a truncation of at least part of the C-terminus of Sema3C, the C-terminus set forth in SEQ ID NO: 34. According to some embodiments, the Sema3C variant of the invention comprises a complete truncation of the C-terminus of Sema3C, the C-terminus set forth in SEQ ID NO: 34. According to some embodiments, the variant of the invention comprises at least one modification in the C-terminus of Sema3C, the C-terminus set forth in SEQ ID NO: 34.

According to some embodiments, the modification is a modification of at least one Arginine residue within a furin-like pro-protein convertase cleavage site. Non-limiting examples of modifications of at least one Arginine residue within furin-like pro protein convertase cleavage site 2 are modifications of site 2 from RSRR (as set forth in SEQ ID NO: 3) to RSKR (as set forth in SEQ ID NO: 11), KSKR (as set forth in SEQ ID NO: 12), or KSKK (as set forth in SEQ ID NO: 13). Each possibility represents a separate embodiment of the present invention.

According to some embodiments, the modification is a modification of at least one Arginine residue within a furin-like pro-protein convertase cleavage site to a Lysine residue. According to other embodiments, the modification is a modification of all Arginine residues within a furin-like pro-protein convertase cleavage site.

According to some embodiments, the modification prevents the variant of the invention from being cleaved at a furin-like pro-protein convertase cleavage site. According to some embodiments, the modification prevents the variant of the invention from being cleaved at a furin-like pro-protein convertase cleavage site by members of the furin-like pro-protein convertases (FPPCs). According to some embodiments, the members of the furin-like pro-protein convertases are selected from the group consisting of: furin, PC 1/3, PC2, PC4, PC 5/6, PACE4, PC7, Site-1 Protease, NARC-1 and a combination thereof. Each possibility represents a separate embodiment of the present invention.

According to some embodiments, the Semaphorin 3C variant of the invention further comprises a protein tag. According to some embodiments, the protein tag is selected from the group consisting of: an N-terminal protein tag, a C-terminal protein tag and a combination thereof. Each possibility represents a separate embodiment of the present invention. According to some embodiments, the Semaphorin 3C variant of the invention is conjugated to a moiety which extends the half-life of said variant. According to some embodiments, wild-type Semaphorin 3C according to the invention is conjugated to a moiety which extends the half-life of said variant. Non-limiting examples of moieties which may extend the half-life of the Semaphorin3C variants of the invention are polyethylene glycol (PEG), polypeptides such as poly-glycine and XTEN (Amunix), hyaluronic acid, albumin and an immunoglobulin or a part thereof, such as, but not limited to, the Fc region.

According to some embodiments, the Semaphorin 3C variant of the invention comprises a protein tag. According to some embodiments, the Semaphorin 3C variant of the invention comprises a protein tag upon production but the tag is cleaved and/or removed from the variant prior to incorporation into the composition of the invention and/or use in treating cancer. Each possibility represents a separate embodiment of the present invention. Cleavage and/or removal of a protein tag may be performed by any methods known in the art, such as, but not limited to, enzymatic and/or chemical cleavage, so as long as the Sema3C variant remains functional. According to some embodiments, a functional Semaphorin3C variant refers to a variant which is able to treat cancer. According to some embodiments, a functional Semaphorin3C variant refers to a variant which is able to suppress growth of a tumor and/or reduce occurrence of metastases. Each possibility represents a separate embodiment of the present invention. According to some embodiments, a functional Semaphorin3C variant refers to a variant which is able to inhibit angiogenesis. According to some embodiments, a functional Semaphorin3C variant refers to a variant which is able to inhibit lymphangiogenesis. According to some embodiments, a functional Semaphorin3C variant refers to a variant which is able to elicit at least one activity selected from the group consisting of: inhibit angiogenesis, inhibit lymphangiogenesis, suppress growth of a cancerous tumor and reduce occurrence of metastases. Each possibility represents a separate embodiment of the present invention. Non-limiting examples of Sema3C variants comprising a protein tag according to the present invention are: UNCL-Sema3C/FC (as set forth in SEQ ID NO: 8) and UNCL-Sema3C/myc-6His (as set forth in SEQ ID NO: 9), produced as described herein below in Example 1.

According to some embodiments, wild-type Semaphorin 3C as set forth in SEQ ID NO: 1 further comprises a protein tag. According to some embodiments, wild-type Semaphorin 3C as set forth in SEQ ID NO: 1 comprises a protein tag upon production but the tag is cleaved and/or removed from the variant prior to incorporation into a pharmaceutical composition of the invention and/or use in inhibiting lymphogenesis and/or angiogenesis. Each possibility represents a separate embodiment of the present invention.

As used herein, the term "protein tag" refers to a peptide sequence bound to the N-terminus or C-terminus of a protein. According to some embodiments, protein tags may comprise glycoproteins. According to some embodiments, protein tags may be used for separation and/or purification and/or visualization of the bound proteins. Each possibility represents a separate embodiment of the present invention. Non-limiting examples of protein tags are: Fc, Myc, Human influenza hemaglutinin (HA), Flag, His, Gluthathione-S-Transferase (GST) and a combination thereof. Each possibility represents a separate embodiment of the present invention. As used herein, an Fc tag refers to a tag encoding at least part of the Fc region of an immunoglobulin G (IgG) class antibody.

According to some embodiments, the Sema3C variant of the invention is an isolated variant. As used herein, the term "isolated" means either: 1) separated from at least some of the components with which it is usually associated in nature; 2) prepared or purified by a process that involves the hand of man; and/or 3) not occurring in nature.

According to some embodiments, the Semaphorin 3C variants of the invention, as disclosed herein, may be produced by recombinant or chemical synthetic methods. According to some embodiments, the Semaphorin 3C variants of the invention, as disclosed herein may be produced by recombinant methods from genetically-modified host cells. Any host cell known in the art for the production of recombinant proteins may be used for the present invention. In some embodiments, the host cell is a prokaryotic cell. Representative, non-limiting examples of appropriate prokaryotic hosts include bacterial cells, such as cells of *Escherictahia coli* and *Bacillus subtilis*. In other embodiments, the host cell is a eukaryotic cell. In some exemplary embodiments, the host cell is a fungal cell, such as yeast. Representative, non-limiting examples of appropriate yeast cells include *Saccharomyces cerevisiae* and *Pichia pastoris*.

In additional exemplary embodiments, the host cell is a plant cell. According to other exemplary embodiments, the host cell is a mammalian cell in culture. Following are non-limiting examples of recombinant and chemical synthetic methods suitable for production of the Semaphorin 3C variants of the invention.

Recombinant Expression

As used herein, the term "gene" has its meaning as understood in the art. In general, a gene is taken to include gene regulatory sequences (e.g. promoters, enhancers, etc.) and/or intron sequences, in addition to coding sequences (open reading frames).

As used herein, the terms "polypeptide" and "protein" are used interchangeably and refer to a polymer of amino acid residues.

As used herein, the term "DNA construct" refers to an artificially assembled or isolated nucleic acid molecule which comprises a gene of interest or a coding region of interest. According to some embodiments, the coding region of interest is cDNA encoding a Sema3C variant of the invention, such as, but not limited to variants set forth in sequences selected from the group consisting of: SEQ ID NO. 8, SEQ ID NO. 9, SEQ ID NO. 10, SEQ ID NO. 35. Each possibility represents a separate embodiment of the present invention.

As used herein, the term "vector" refers to any recombinant polynucleotide construct (such as a DNA construct) that may be used for the purpose of transformation, i.e. the introduction of heterologous DNA into a host cell. One exemplary type of vector is a "plasmid" which refers to a circular double stranded DNA loop into which additional DNA segments can be ligated. Another exemplary type of vector is a viral vector, wherein additional DNA segments can be ligated into the viral genome. Certain vectors are capable of autonomous replication in a host cell into which they are introduced.

As used herein, a "primer" defines an oligonucleotide which is capable of annealing to (hybridizing with) a target nucleotide sequence, thereby creating a double stranded region which can serve as an initiation point for DNA synthesis under suitable conditions.

As used herein, the terms "transformation" refers to the introduction of foreign DNA into cells. The terms "transformants" or "transformed cells" include the primary transformed cell and cultures derived from that cell regardless to the number of transfers. All progeny may not be precisely identical in DNA content, due to deliberate or inadvertent mutations. Mutant progeny that have the same functionality as screened for in the originally transformed cell are included in the definition of transformants.

A Semaphorin 3C variant may be synthesized by expressing a polynucleotide molecule encoding the variant in a host cell, for example, a microorganism cell transformed with the nucleic acid molecule.

DNA sequences encoding wild type polypeptides, such as Semaphorin 3C, may be isolated from any cell producing them, using various methods well known in the art. For example, a DNA encoding the wild-type polypeptide may be amplified from genomic DNA by polymerase chain reaction (PCR) using specific primers, constructed on the basis of the nucleotide sequence of the known wild type sequence. The genomic DNA may be extracted from the cell prior to the amplification using various methods known in the art.

The isolated polynucleotide encoding the wild type polypeptide may be cloned into a vector, such as, but not limited to, the pET28a or pGEM-T easy plasmids.

Upon isolation and cloning of the polynucleotide encoding the wild type polypeptide, desired mutation(s) may be introduced, in order to arrive at a polynucleotide sequence encoding a desired Sema3C variant according to the invention, by modification at one or more base pairs, using methods known in the art. Such methods include, for example, site-specific mutagenesis, cassette mutagenesis, recursive ensemble mutagenesis and gene site saturation mutagenesis. Methods are also well known for introducing multiple mutations into a polynucleotide. For example, introduction of two and/or three mutations can be performed using commercially available kits, such as the QuickChange site-directed mutagenesis kit (Stratagene).

An alternative method to producing a polynucleotide with a desired sequence is the use of a synthetic gene. A polynucleotide encoding a desired polypeptide may be prepared synthetically, for example using the phosphoroamidite method. The polynucleotide thus produced may then be subjected to further manipulations, including one or more of purification, annealing, ligation, amplification, digestion by restriction endonucleases and cloning into appropriate vectors. The polynucleotide may be ligated either initially into a cloning vector, or directly into an expression vector that is appropriate for its expression in a particular host cell type. In the case of a fusion protein, or a protein fused with a protein tag, different polynucleotides may be ligated to form one polynucleotide. For example, different polynucleotides may be ligated into linearized pET21a.

The polynucleotide encoding the Sema3C variant of the invention may be incorporated into a wide variety of expression vectors, which may be transformed into in a wide variety of host cells.

Introduction of a polynucleotide into the host cell can be effected by well-known methods, such as chemical transformation (e.g. calcium chloride treatment), electroporation, conjugation, transduction, calcium phosphate transfection, DEAE-dextran mediated transfection, transvection, microinjection, cationic lipid-mediated transfection, scrape loading, ballistic introduction and infection.

Representative, non-limiting examples of appropriate hosts include bacterial cells, such as cells of *E. coli* and *Bacillus subtilis*. The variants of the invention may be encoded in any vector suitable for expression. The appropriate vector is determined according to the selected host cell. Vectors for expressing proteins in *E. coli*, for example, include, but are not limited to, pET, pK233, pT7 and lambda pSKF. Other expression vector systems are based on beta-galactosidase (pEX); maltose binding protein (pMAL); and glutathione S-transferase (pGST). The polypeptides may be designed to include a protein tag, for example, a His-Tag (six consecutive histidine residues), which can be isolated and purified by conventional methods.

Selection of a host cell transformed with the desired vector may be accomplished using standard selection protocols involving growth in a selection medium which is toxic to non-transformed cells. For example, in the case of *E. coli*, it may be grown in a medium containing an antibiotic selection agent; cells transformed with the expression vector which further provides an antibiotic resistance gene, will grow in the selection medium.

Upon transformation of a suitable host cell, and propagation under conditions appropriate for protein expression, the variant of the invention may be identified in cell extracts of the transformed cells. Transformed hosts expressing the variant of the invention may be identified by analyzing the proteins expressed by the host, for example, using SDS-PAGE and comparing the gel to an SDS-PAGE gel obtained from the host which was transformed with the same vector but not containing a nucleic acid sequence encoding the desired variant.

The desired variants which have been identified in cell extracts may be isolated and purified by conventional methods, including ammonium sulfate or ethanol precipitation, acid extraction, salt fractionation, ion exchange chromatography, hydrophobic interaction chromatography, gel permeation chromatography, affinity chromatography, and combinations thereof.

The isolated variants may be analyzed for their various properties, for example specific activity, using methods known in the art. In a non-limiting example, Semaphorin 3C variants according to the invention may be analyzed for their ability to induce contraction of human umbilical vein-derived endothelial cells (HUVECs). Conditions for carrying out the aforementioned procedures as well as other useful methods are readily determined by those of ordinary skill in the art.

Synthetic Production

Semaphorin 3C variants according to the present invention may also be produced by synthetic means using well known techniques, such as solid phase synthesis. Synthetic polypeptides may be produced using commercially available laboratory peptide design and synthesis kits. In addition, a number of available FMOC peptide synthesis systems are available. Assembly of a polypeptide or fragment can be carried out on a solid support using for example, an Applied Biosystems, Inc. Model 431A automated peptide synthesizer. The polypeptides may be made by either direct synthesis or by synthesis of a series of fragments that can be coupled using other known techniques.

According to some embodiments, the present invention provides a polynucleotide corresponding to the Sema3C variant of the invention. According to some embodiments, the present invention provides a polynucleotide encoding cDNA which corresponds to the Sema3C variant of the invention.

According to some embodiments, the present invention provides a polynucleotide encoding the Sema3C variant of the invention. According to some embodiments, the present invention provides a polynucleotide encoding a variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site.

According to some embodiments, the present invention provides a polynucleotide encoding a variant of Semaphorin 3C as set forth in SEQ ID NO: 1, wherein the variant comprises at least one modification in furin-like pro-protein convertase cleavage site 2 consisting of amino acid residues 549-552 and at least one modification in furin-like pro-protein convertase cleavage site 3 consisting of amino acid residues 742-745; and wherein the modifications render said variant resistant to cleavage at said cleavage sites.

According to some embodiments, the present invention provides a polynucleotide encoding a Sema3C variant according to the invention which comprises a protein-tag, such as, but not limited to, the polynucleotides encoded by SEQ ID NO: 22 and SEQ ID NO: 23 encoding the variants having SEQ ID NO:8 or SEQ ID NO: 9, respectively. According to some embodiments, the present invention provides a polynucleotide encoding the Sema3C variant encoded by SEQ ID NO: 35.

According to some embodiments, the invention provides a vector comprising the polynucleotide of the invention. As used herein, the term "the polynucleotide of the invention" refers to a polynucleotide encoding the variant of the invention. According to some embodiments, the present invention provides a host cell transfected with a vector comprising the polynucleotide of the invention.

According to some embodiments, the present invention provides a pharmaceutical composition comprising a variant of Semaphorin 3C as set forth in SEQ ID NO: 1, wherein the variant comprises at least one modification in furin-like pro-protein convertase cleavage site 2 consisting of amino acid residues 549-552 of Sema3C as set forth in SEQ ID NO: 1; wherein the modification renders the variant resistant to cleavage at cleavage site 2.

According to some embodiments, the present invention provides a pharmaceutical composition comprising a variant of Semaphorin 3C as set forth in SEQ ID NO: 1, wherein the variant comprises at least one modification in furin-like pro-protein convertase cleavage site 2 consisting of amino acid residues 549-552 and at least one modification in furin-like pro-protein convertase cleavage site 3 consisting of amino acid residues 742-745; and wherein the modifications render said variant resistant to cleavage at said cleavage sites.

According to some embodiments, the present invention provides a pharmaceutical composition comprising at least one of the Sema3C variants of the invention. According to some embodiments, the present invention provides a pharmaceutical composition comprising a therapeutically effective amount of at least one of the Sema3C variants of the invention. According to some embodiments, the pharmaceutical composition of the invention further comprises a pharmaceutically acceptable carrier. As used herein, the term "the pharmaceutical composition of the invention" refers to a composition comprising at least one of the Sema3C variants of the invention.

According to another aspect, the present invention provides a pharmaceutical composition comprising as an active ingredient a therapeutically effective amount of wild-type Semaphorin 3C as set forth in SEQ ID NO: 1.

According to another aspect, the present invention provides a method for treating cancer in a subject, the method comprising administering the pharmaceutical composition of the invention to the subject. According to some embodiments, the present invention provides a method for treating cancer in a subject, the method comprising administering to the subject a pharmaceutical composition comprising a therapeutically effective amount of at least one of the Sema3C variants of the invention. According to some embodiments, the present invention provides a method for treating cancer in a subject, the method comprising administering to the subject a pharmaceutical composition comprising as an active ingredient a therapeutically effective amount of wild-type Semaphorin 3C as set forth in SEQ ID NO: 1.

According to some embodiments, the present invention provides a method for treating cancer in a subject, the method comprising administering to the subject a pharmaceutical composition comprising a therapeutically effective amount of at least one variant of Semaphorin 3C as set forth in SEQ ID NO: 1, wherein the variant comprises at least one modification in furin-like pro-protein convertase cleavage site 2 consisting of amino acid residues 549-552 of Sema3C as set forth in SEQ ID NO: 1; wherein the modification renders the variant resistant to cleavage at cleavage site 2.

The experiments in the Examples Section show that the class-3 semaphorin sema3C is the only class-3 semaphorin besides sema3F that is able to induce the collapse of the cytoskeleton of LEC suggesting that sema3C may function as a modulator of lymphangiogenesis and of lymph vessels mediated tumor metastasis. The sema3C cleavage product p65-Sema3C was inactive when its ability to induce the collapse of the cytoskeleton of LEC was examined. Accordingly, the point mutated FR-sema3C variant of sema3C which is resistant to cleavage by FPPC was used in the experiments.

FR-sema3C effectively induced the collapse of the cytoskeleton of LEC and HUVEC. These effects were mediated in LEC by the neuropilin-2 receptor and by the D1 and A1 plexin receptors which form functional class-3 semaphorin receptors when they associate with neuropilins Silencing plexin-A3 had no effect on FR-sema3C/Fc induced contraction of LEC. This is surprising because sema3F, the other semaphorin that induces contraction of LEC is known to transduce signals using neuropilin-2 and plexin-A3. FR-sema3C also inhibited potently the proliferation of LEC and less effectively the proliferation of vascular endothelial cells. Like wild type sema3C, FR-sema3C had no effect either on the proliferation or on the cytoskeletal organization of the highly metastatic LM2-4 breast cancer cells, possibly because these cells do not express the neuropilin-2 receptor. FR-sema3C inhibited VEGF-C induced signal transduction in LEC suggesting that it may indeed function in-vivo as an inhibitor of lymphangiogenesis. FR-sema3C expressing LM2-4 cells formed tumors in mammary fat pads of mice but their growth was inhibited by about 50% as compared with the growth rate of control tumors. This was probably the result of an anti-angiogenic effect because the concentration of blood vessels in tumors formed from FR-sema3C expressing cells was reduced by 50% as compared to their concentration in tumors that developed from control cells. The reduced concentration of blood vessels cannot be explained solely by a direct effect of FR-sema3C on endothelial cells of blood vessels because in-vitro FR-sema3C only inhibited the proliferation of vascular endothelial cells by about 20%. A reduction in the concentration of activated M2 macrophages in the FR-sema3C expressing tumors. M2 tumor associated macrophages were found to enhance angiogenesis and lymphangiogenesis was also observed and it is possible that inhibition of their recruitment by FR-sema3C contributes to the FR-sema3C induced inhibition of angiogenesis and lymphangiogenesis.

The concentration of lymph vessels in the tumors that developed from the FR-sema3C expressing cells was also reduced by about 50% as compared to their density in control tumors, suggesting that FR-sema3C does indeed function as an anti-lymphangiogenic factor. The expression of FR-sema3C in the tumor cells inhibited potently the spread of tumor cells to lymph nodes Similar effects were observed when signal transduction induced by lymphangiogenic factors such as VEGF-C and VEGF-D was inhibited, suggesting that the inhibition of metastasis by FR-sema3C is indeed due to its anti-lymphangiogenic activity. Both the number of metastases containing lymph nodes as well as the size of metastases in metastases containing lymph nodes were reduced in mice harbouring tumors derived from FR-sema3C expressing LM2-4 cells. These results suggest that FR-sema3C may be used to inhibit the metastatic spread of breast cancer tumors and possibly of additional types of tumors that disseminate using the lymphatic system.

According to some embodiments, the present invention provides a method for treating cancer in a subject, the method comprising administering to the subject a pharmaceutical composition comprising a therapeutically effective amount of at least one variant of Semaphorin 3C as set forth in SEQ ID NO: 1, wherein the variant comprises at least one modification in furin-like pro-protein convertase cleavage site 2 consisting of amino acid residues 549-552 and at least one modification in furin-like pro-protein convertase cleavage site 3 consisting of amino acid residues 742-745; and wherein the modifications render said variant resistant to cleavage at said cleavage sites.

According to some embodiments, as used herein, the term "therapeutically effective amount" relates to an amount sufficient to induce at least one of the following clinical effects when administered to a subject: suppression of tumor growth in the subject, reduction of metastases occurrence in the subject, inhibition of lymphangiogenesis, inhibition of angiogenesis and a combination thereof. Each possibility represents a separate embodiment of the present invention.

According to some embodiments, treating is selected from the group consisting of: suppressing growth of a tumor, reducing occurrence of metastases and a combination thereof. Each possibility represents a separate embodiment of the present invention. According to some embodiments, treating is suppressing growth of a tumor in a subject. According to some embodiments, treating is arresting growth of a tumor in a subject. According to some embodiments, a tumor in a subject treated with the composition of the invention according to the methods of the invention is of a smaller size and/or weight than a comparable tumor in a subject not treated with the composition of the invention. Each possibility represents a separate embodiment of the present invention.

According to some embodiments, treating is reducing occurrence of metastases in a subject. According to some embodiments, treating is reducing occurrence of metastases in lymph nodes of a subject. According to some embodiments, treating is reducing occurrence of metastases in sentinel lymph nodes of a subject. As used herein, the term "sentinel lymph nodes" refers to lymph nodes draining a cancer tumor. According to some embodiments, treating is reducing the number of metastases in a subject. According to some embodiments, treating is reducing the size of metastases in a subject. According to some embodiments, metastases are metastases in lymph nodes, preferably metastases in sentinel lymph nodes. According to some embodiments, treating is inhibiting growth of metastases. According to some embodiments, treating is inhibiting or suppressing the spreading of metastases. Each possibility represents a separate embodiment of the present invention. According to some embodiments, treating is inhibiting or suppressing the spreading of metastases to lymph nodes, preferably to sentinel lymph nodes. Each possibility represents a separate embodiment of the present invention. Without wishing to be bound by any theory or mechanism, the ability of the Sema3C variants of the invention to inhibit or suppress lymphangiogenesis may contribute to their ability to suppress or inhibit the spreading of metastases to sentinel lymph nodes of a tumor.

According to some embodiments, treating is inhibiting lymphangiogenesis. According to some embodiments, treating is suppressing lymphangiogenesis. According to some embodiments, treating is inhibiting or suppressing lymphangiogenesis in a tumor. Each possibility represents a separate embodiment of the present invention. According to some embodiments, treating is inducing contraction of lymphatic endothelial cells. According to some embodiments, treating is reducing the density of lymph nodes in a tumor. According to some embodiments, treating is suppressing growth of lymph nodes in a tumor. According to some embodiments, treating is reducing the density of tumor associated lymph vessels. According to some embodiments, treating is suppressing growth of tumor associated lymph vessels. According to some embodiments, treating is reducing lymphatic drainage of a tumor.

According to some embodiments, "tumor" as used herein refers to an abnormal mass of tissue resulting from cancer. According to some embodiments, cancer according to the present invention is selected from the group consisting of: lymphoma, breast cancer, head and neck cancer, squamous carcinomas of the head and neck (HNSCC), lung cancer, rectal cancer, bile duct cancer, bladder cancer, bone cancer, colon cancer, brain cancer, cervical cancer, ocular melanoma, Kaposi's sarcoma, leukemia, melanoma, myeloma, ovarian cancer, vaginal cancer, prostate cancer, testicular cancer, endometrial cancer, thyroid cancer and thymus cancer. Each possibility represents a separate embodiment of the present invention. According to some embodiments, the cancer is breast cancer. According to some embodiments, the cancer is lymphoma. According to some embodiments, the cancer is a cancer which induces tumors that send metastases into lymph nodes. According to some embodiments, the cancer is a cancer which spreads through lymph nodes. According to some embodiments, the cancer is a cancer which spreads through lymph nodes such as, but not limited to, breast cancer, malignant melanoma, lymphoma and head and neck cancer. According to some embodiments, the cancer is a cancer which induces tumors that secrete factors which induce angiogenesis. According to some embodiments, the cancer is a cancer which induces tumors that secrete factors which induce lymphangiogenesis. According to some embodiments, the cancer is a cancer which induces tumors that secrete at least one type of furin-like pro-protein convertase (FPPC). According to some embodiments, the cancer is a cancer which induces tumors that secrete at least one type of furin-like pro-protein convertase (FPPC) known to cleave Sema3C at site 2. According to some embodiments, the cancer is a cancer which induces tumors that secrete at least one type of furin-like pro-protein convertase (FPPC) known to cleave Sema3C at site 2 and/or site 3. Each possibility represents a separate embodiment of the present invention. Without wishing to be bound by any theory or mechanism, the Sema3C variants of the invention are suitable to treat a tumor that secretes at least one type of FPPC known to cleave Sema3C, since they are not susceptible to the effects of the FPPCs.

According to some embodiments, the present invention provides the composition of the invention for treating cancer in a subject. According to some embodiments, the present invention provides a pharmaceutical composition comprising as an active ingredient a therapeutically effective amount of wild-type Semaphorin 3C as set forth in SEQ ID NO: 1 for treating cancer in a subject.

According to another aspect, the present invention provides a method for inhibiting or suppressing lymphangiogensis in a subject, the method comprising administering to a subject a pharmaceutical composition comprising a therapeutically effective amount of at least one of the Sema3C variants of the invention. Each possibility represents a separate embodiment of the present invention. According to some embodiments, the present invention provides a method for inhibiting or suppressing lymphangiogensis in a subject, the method comprising administering to a subject a pharmaceutical composition comprising as an active ingredient a therapeutically effective amount of wild-type Semaphorin 3C as set forth in SEQ ID NO: 1.

According to some embodiments, the present invention provides a method of treatment of a disease or condition which is associated with excessive lymphangiogenesis or which may benefit from inhibition or suppression of lymphangiogenesis, the method comprising administering to a subject a pharmaceutical composition comprising a therapeutically effective amount of at least one of the Sema3C variants of the invention. Each possibility represents a separate embodiment of the present invention. According to some embodiments, the present invention provides a method of treatment of a disease or condition which is associated with excessive lymphangiogenesis or which may benefit from inhibition or suppression of lymphangiogenesis, the method comprising administering to a subject a pharmaceutical composition comprising as an active ingredient a therapeutically effective amount of wild-type Semaphorin 3C as set forth in SEQ ID NO: 1. Each possibility represents a separate embodiment of the present invention. Non-limiting examples of conditions which may benefit from reduced lymphangiogenesis are lymphatic edema and lymphangiomatosis.

As used herein, the term "lymphangiogenesis" refers to formation and/or growth of lymphatic vessels de-novo or from existing lymphatic vessels. As exemplified herein below, aside from Sema3F previously shown as a repellent of lymphatic endothelial cells (LECs), Sema3C was unexpectedly found to be the only class 3 Semaphorin to induce LEC collapse.

According to some embodiments, the present invention provides a method for inhibiting lymphangiogensis in a subject, the method comprising administering to a subject a pharmaceutical composition comprising a therapeutically effective amount of at least one variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site. Each possibility represents a separate embodiment of the present invention. According to some embodiments, a therapeutically effective amount is an amount sufficient for inhibiting lymphangiogenesis in a subject.

According to some embodiments, administration of the pharmaceutical composition of the invention to a subject results in inhibition or suppression of lymphangiogenesis. Each possibility represents a separate embodiment of the present invention. According to some embodiments, administering the composition of the invention to a subject afflicted with cancer results in inhibiting or suppressing lymphangiogenesis in a tumor. Each possibility represents a separate embodiment of the present invention. According to some embodiments, administering the composition of the invention to a subject afflicted with cancer results in inhibiting or suppressing lymphangiogenesis of tumor associated lymph vessels. Each possibility represents a separate embodiment of the present invention. According to some embodiments, inhibition or suppression of lymphangiogenesis refers to inhibition or suppression of at least 50%, possibly at least 70%, alternatively at least 90% of lymphangiogenesis in a subject non-treated with the composition of the invention or a composition comprising wild type Sema3C as set forth in SEQ ID NO: 1. Each possibility represents a separate embodiment of the present invention. According to some embodiments, inhibition or suppression of lymphangiogenesis is local. According to some embodiments, administering the composition of the invention to a subject afflicted with cancer results in reduction in the density of tumor associated lymph vessels. According to some embodiments, administering the composition of the invention to a subject afflicted with cancer results in suppression of tumor associated lymph vessel growth. According to some embodiments, administering the composition of the invention to a subject afflicted with cancer results in reduction of lymphatic drainage of a tumor.

Without wishing to be bound by any theory or mechanism, the ability of the Sema3C variants of the invention to reduce the density of tumor associated lymph vessels, may contribute to their ability to suppress tumor growth and/or suppress the spreading of metastases to sentinel lymph nodes.

According to some embodiments, the variant of the invention is capable of suppressing or inhibiting lymphangiogenesis. Each possibility represents a separate embodiment of the present invention. According to some embodiments, the variant of the invention is capable of suppressing or inhibiting spread of metastases. Each possibility represents a separate embodiment of the present invention. According to some embodiments, the variant of the invention is capable of suppressing or inhibiting spread of metastases to lymph nodes, preferably sentinel lymph nodes. Each possibility represents a separate embodiment of the present invention.

According to some embodiments, the present invention provides the composition of the invention for inhibiting or suppressing lymphangiogenesis. Each possibility represents a separate embodiment of the present invention. According to some embodiments, the present invention provides a pharmaceutical composition comprising as an active ingredient a therapeutically effective amount of wild-type Semaphorin 3C as set forth in SEQ ID NO: 1 for inhibiting or suppressing lymphangiogenesis. Each possibility represents a separate embodiment of the present invention.

According to another aspect, the present invention provides a method for inhibiting or suppressing angiogensis in a subject, the method comprising administering to a subject a pharmaceutical composition comprising a therapeutically effective amount of at least one of the Sema3C variants of the invention. Each possibility represents a separate embodiment of the present invention. According to another aspect, the present invention provides a method for inhibiting or suppressing angiogenesis in a subject, the method comprising administering to a subject a pharmaceutical composition comprising as an active ingredient a therapeutically effective amount of wild-type Semaphorin 3C as set forth in SEQ ID NO: 1.

According to some embodiments, inhibition or suppression of angiogenesis refers to inhibition or suppression of at least 50%, preferably at least 70%, most preferably at least 90% of angiogenesis in a subject non-treated with the composition of the invention. Each possibility represents a separate embodiment of the present invention.

According to some embodiments, the present invention provides a method for inhibiting angiogensis in a subject, the method comprising administering to a subject a pharmaceutical composition comprising a therapeutically effective amount of at least one variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site. Each possibility represents a separate embodiment of the present invention. According to some embodiments, a therapeutically effective amount is an amount sufficient for inhibiting lymphangiogenesis in a subject.

As used herein, the term "angiogenesis" refers to formation of blood-vessels de-novo or from existing blood vessels. According to some embodiments, administration of the composition of the invention results in collapse of blood-vessel endothelial cells. According to some embodiments, administration of the composition of the invention to a subject afflicted with cancer results in inhibition or suppression of angiogenesis of blood cells supplying blood to a tumor and/or metastases. Each possibility represents a separate embodiment of the present invention. Without wishing to be bound by any theory or mechanism, the ability of wild-type Sema3C and the Sema3C variants of the invention to inhibit both angiogenesis and lymphangiogenesis contributes to their ability to suppress the growth of a tumor and/or reduce occurrence of metastases, mostly metastases in lymph nodes. According to some embodiments, the variant of the invention is capable of suppressing or inhibiting angiogenesis. Each possibility represents a separate embodiment of the present invention.

According to some embodiments, the present invention provides the composition of the invention for suppression or inhibition of angiogenesis. Each possibility represents a separate embodiment of the present invention. According to some embodiments, the present invention provides a pharmaceutical composition comprising as an active ingredient a therapeutically effective amount of wild-type Semaphorin 3C as set forth in SEQ ID NO: 1 for suppression or inhibition of angiogenesis. Each possibility represents a separate embodiment of the present invention.

According to some embodiments, as used herein, the terms "subject" or "a subject in need thereof" are used interchangeably and refer to a subject afflicted with a pathology selected from the group consisting of: cancer, a pathology which would benefit from inhibition of lymphangiogenesis, a pathology which would benefit from inhibition of angiogenesis and a combination thereof. Each possibility represents a separate embodiment of the present invention. According to some embodiments, a subject is a subject afflicted with cancer. According to some embodiments, a subject is a subject afflicted with a pathology which would benefit from inhibition of lymphangiogenesis. According to some embodiments, a subject is a subject afflicted with a pathology which would benefit from inhibition of angiogenesis.

Any suitable route of administration to a subject may be used for the composition of the present invention, including but not limited to, topical and systemic routes. According to some embodiments, administering is administering systematically. According to some embodiments, the composition is formulated for systemic administration.

According to another embodiment, administration systemically is through a parenteral route. According to some embodiments, preparations of the composition of the invention for parenteral administration include sterile aqueous or non-aqueous solutions, suspensions, or emulsions, each representing a separate embodiment of the present invention. Non-limiting examples of non-aqueous solvents or vehicles are propylene glycol, polyethylene glycol, vegetable oils such as olive oil and corn oil, gelatin, and injectable organic esters such as ethyl oleate.

According to some embodiments, parenteral administration is administration intravenously, intra-arterially, intra-muscularly, intraperitoneally, intradermally, transdermally, intravitreally, or subcutaneously. Each of the abovementioned administration routes represents a separate embodiment of the present invention. According to another embodiment, parenteral administration is performed by bolus injection. According to another embodiment, parenteral administration is performed by continuous infusion.

According to another embodiment, parenteral administration is transmucosal administration. According to another embodiment, transmucosal administration is transnasal administration. For transmucosal administration, penetrants appropriate to the barrier to be permeated are used in the formulation. Such penetrants are generally known in the art. The preferred mode of administration will depend upon the particular indication being treated and will be apparent to one of skill in the art.

Abnormal lymphangiogenesis is a complicating factor in additional diseases. Abnormal angiogenesis and lymphangiogenesis represents a complication of inflammatory several eye diseases in which new blood vessels and new lymph vessels invade the normally transparent cornea. This can be induced by irritants, limbal insufficiency, or complications of surgical procedures such cornea grafting and cause loss of vision. These observations suggest that inhibitors of lymphangiogenesis could be useful as drugs for the treatment of such eye diseases as well as of additional diseases involving inflammatory lymphangiogenesis such as inflammatory bowel disease or various complications of diabetes. Indeed, some inhibitors targeting the VEGFR-3 receptor which acts as the receptor for the lymphangiogenic factors VEGF-C and VEGF-D are currently in clinical trials. Accordingly, it is intended to determine if injection of FR-sema3C or application of eye drops containing FR-sema3C can be used to treat such corneal diseases in pre-clinical animal models.

Inflammation, neo-lymphangiogenesis and neo-angiogenesis will be induced in the corneas of eyes of c57 black mice or rat eyes using alkali burn or suture placement as described. FR-sema3C/Fc will be applied as drops or by injection in order to determine if it inhibits neo-angiogenesis and neo-lymphangiogenesis. Vehicle alone will be used as a control, and results will be compared to the effects of the VEGF inhibitor Avastin. A positive result will be a significant inhibition of lymphangiogenesis and angiogenesis to the cornea.

In some embodiments of the invention, there is provided a method for reducing corneal lymphangiogenesis in a subject in need thereof, comprising the steps of: (a) identifying a subject with corneal lymphangiogenesis; and (b) locally administering to the cornea of said subject a composition comprising an effective amount of a variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and/or wherein said variant has at least one modification in furin-like pro-protein convertase cleavage site 3 consisting of amino acid residues 742-745; and wherein said modification renders said variant resistant to cleavage at said cleavage site 3, thereby inhibiting the ability of lymphatic vessels to expand within or invade corneal tissue and reducing corneal lymphangiogenesis.

In some embodiments of the invention, there is provided a method for minimizing or preventing corneal lymphangiogenesis in a subject in need thereof, comprising the steps of: (a) identifying said subject at risk of developing lymphangiogenesis onset; and (b) locally administering to the cornea of said subject a composition comprising an effective amount of A variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and/or wherein said variant has at least one modification in furin-like pro-protein convertase cleavage site 3 consisting of amino acid residues 742-745; and wherein said modification renders said variant resistant to cleavage at said cleavage site 3 prior to said development, thereby inhibiting the ability of lymphatic vessels to form or expand within, or to invade corneal tissue.

In some embodiments of the invention, there is provided a method for reducing corneal lymphangiogenesis in a subject in need thereof, comprising the steps of: (a) identifying a subject with corneal lymphangiogenesis; and (b) administering to the subject a composition comprising an effective amount of a variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and/or wherein said variant has at least one modification in furin-like pro-protein convertase cleavage site 3 consisting of amino acid residues 742-745; and wherein said modification renders said variant resistant to cleavage at said cleavage site 3, thereby inhibiting the ability of lymphatic vessels to expand within or invade corneal tissue and reducing corneal lymphangiogenesis.

In some embodiments of the invention, there is provided a method for minimizing or preventing corneal lymphangiogenesis in a subject in risk thereof, comprising the steps of: (a) identifying said subject at risk of developing lymphangiogenesis onset; and (b) administering to the subject a composition comprising an effective amount of A variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and/or wherein said variant has at least one modification in furin-like pro-protein convertase cleavage site 3 consisting of amino acid residues 742-745; and wherein said modification renders said variant resistant to cleavage at said cleavage site 3 prior to said development, thereby inhibiting the ability of lymphatic vessels to form or expand within, or to invade corneal tissue.

According to some embodiments, reduction or prevention of corneal lymphangiogenesis refers to inhibition or suppression of at least 50%, preferably at least 70%, most preferably at least 90% of angiogenesis in a subject non-treated with the composition of the invention. Each possibility represents a separate embodiment of the present invention.

In some embodiments of the invention, there is provided a method for treating diabetes or IBD comprising the steps of administering to a subject in need a composition comprising an effective amount of a variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and/or wherein said variant has at least one modification in furin-like pro-protein convertase cleavage site 3 consisting of amino acid residues 742-745; and wherein said modification renders said variant resistant to cleavage at said cleavage site 3.

In some embodiments of the invention, there is provided a Semaphorin 3C variant according to the embodiments of the invention for use for reducing corneal lymphangiogenesis in a subject in need thereof.

In some embodiments of the invention, there is provided a Semaphorin 3C variant according to the embodiments of the invention for use for preventing or minimizing corneal lymphangiogenesis in a subject in risk thereof.

According to another embodiment, systemic administration of the composition is through injection. For administration through injection, the composition may be formulated in an aqueous solution, for example in a physiologically compatible buffer including but not limited to Hank's solution, Ringer's solution, or physiological salt buffer. Formulations for injection may be presented in unit dosage forms, for example, in ampoules, or in multi-dose containers with, optionally, an added preservative.

Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

According to another embodiment, compositions formulated for injection may be in the form of solutions, suspensions, dispersions or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate or triglycerides.

According to another embodiment, the composition is administered intravenously, and is thus formulated in a form suitable for intravenous administration. According to another embodiment, the composition is administered intra-arterially, and is thus formulated in a form suitable for intra-arterial administration. According to another embodiment, the composition is administered intramuscularly, and is thus formulated in a form suitable for intramuscular administration.

According to some embodiments, the composition is administered through direct injection into a tumor. According to some embodiments, the composition is administered through injection to a tumor's environment. According to some embodiments, the composition is administered by injection to a blood vessel in the tumor's environment. According to some embodiments, the composition is administered by injection into a blood vessel supplying blood to a tumor.

According to certain embodiments, administration systemically is through an enteral route. According to another embodiment, administration through an enteral route is oral administration. According to some embodiments, the composition is formulated for oral administration.

According to some embodiments, oral administration is in the form of hard or soft gelatin capsules, pills, capsules, tablets, including coated tablets, dragees, elixirs, suspensions, liquids, gels, slurries, syrups or inhalations and controlled release forms thereof.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin, for use in a dispenser may be formulated containing a powder mix of the composition of the invention and a suitable powder base, such as lactose or starch.

Solid dosage forms for oral administration include capsules, tablets, pill, powders, and granules. In such solid dosage forms, the composition of the invention is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

Liquid dosage forms for oral administration may further contain adjuvants, such as wetting agents, emulsifying and suspending agents, and sweetening, flavoring and perfuming agents. According to some embodiments, enteral coating of the composition is further used for oral or buccal administration. The term "enteral coating", as used herein, refers to a coating which controls the location of composition absorption within the digestive system. Non-limiting examples for materials used for enteral coating are fatty acids, waxes, plant fibers or plastics.

According to some embodiments, administering is administering topically. According to some embodiments, the composition is formulated for topical administration.

According to some embodiments, administration of the composition of the invention to a subject in need thereof is by a route selected from the group consisting of: intravenous, intraarterial, transdermal, subcutaneous, via direct injection into a tissue and via direct injection into a tumor. Each possibility represents a separate embodiment of the present invention. According to certain embodiments, administration may be orally.

According to some embodiments, the present invention provides the pharmaceutical composition of the invention for use in treating cancer in a subject. According to some embodiments, the present invention provides the pharmaceutical composition of the invention for use in inhibiting lymphangiogenesis. According to some embodiments, the present invention provides the pharmaceutical composition of the invention for use in inhibiting angiogenesis.

According to some embodiments, the present invention provides a pharmaceutical composition comprising at least one variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site, for use in treating cancer in a subject.

According to some embodiments, the present invention provides a pharmaceutical composition comprising at least one variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site, for use in inhibiting lymphangiogenesis in a subject.

According to some embodiments, the present invention provides a pharmaceutical composition comprising at least one variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site, for use in inhibiting angiogenesis in a subject.

In some embodiments, the invention further envisages inclusion of a complex of Semaphorin 3C which has at least 80%, 90%, 95%, 99% or 100% sequence identity with the amino acid set forth in SEQ ID NO: 1 or a variant thereof according to the embodiments of the invention where it is attached to proteinaceous (e.g., heterologous amino acid sequence) or non-proteinaceous moieties (e.g., PEG), each of which being capable of prolonging the half-life of the composition while in circulation.

Such a molecule is highly stable (resistant to in-vivo proteaolytic activity, probably due to steric hindrance conferred by the non-proteinaceous moiety) and may be produced using common solid phase synthesis. Further recombinant techniques may still be used, whereby the recombinant peptide product is subjected to in-vitro modification (e.g., PEGylation as further described hereinbelow).

The phrase "non-proteinaceous moiety" as used herein refers to a molecule not including peptide bonded amino acids that is attached to the above-described Semaphorin 3C which has at least 80%, 90%, 95%, 99% or 100% sequence identity with the amino acid set forth in SEQ ID NO: 1 or a variant thereof according to the embodiments of the invention. According to some embodiments the non-proteinaceous moiety may be a polymer or a co-polymer (synthetic or natural). Non-limiting examples of the non-proteinaceous moiety of the present invention include polyethylene glycol (PEG) or derivative thereof, Polyvinyl pyrrolidone (PVP), divinyl ether and maleic anhydride copolymer (DIVEMA); polysialic acid (PSA) and/or poly (styrene comaleic anhydride) (SMA). Additionally, complexes which can protect Semaphorin 3C which has at least 80%, 90%, 95%, 99% or 100% sequence identity with the amino acid set forth in SEQ ID NO: 1 or a variant thereof according to the embodiments of the invention from the environment and thus keep its stability may be used, including, for example, liposomes or micelles. According to some embodiments of the invention, the Semaphorin 3C which has at least 80%, 90%, 95%, 99% or 100% sequence identity with the amino acid set forth in SEQ ID NO: 1 or a variant thereof according to the embodiments of the invention thereof are attached to a non-proteinaceous moiety, which may act as a sustained-release enhancing agent. Exemplary sustained-release enhancing agents include, but are not limited to hyaluronic acid (HA), alginic acid (AA), polyhydroxyethyl methacrylate (Poly-HEMA), glyme and polyisopropylacrylamide.

Attaching the amino acid sequence component Semaphorin 3C which has at least 80%, 90%, 95%, 99% or 100% sequence identity with the amino acid set forth in SEQ ID NO: 1 or a variant thereof according to the embodiments of the invention to other non-amino acid agents may be by covalent linking or by non-covalent complexion, for example, by complexion to a hydrophobic polymer, which can be degraded or cleaved producing a compound capable of sustained release; by entrapping the amino acid part of Semaphorin 3C which has at least 80%, 90%, 95%, 99% or 100% sequence identity with the amino acid set forth in SEQ ID NO: 1 or a variant thereof according to the embodiments of the invention comprising thereof in liposomes or micelles to produce a complex comprising Semaphorin 3C which has at least 80%, 90%, 95%, 99% or 100% sequence identity with the amino acid set forth in SEQ ID NO: 1 or a variant thereof according to the embodiments of the invention. The association may be by the entrapment of the amino acid sequence within the other component (liposome, micelle) or the impregnation of the amino acid sequence within a polymer to produce the final peptide of the invention.

In some embodiments, the PEG derivative is N-hydroxy-succinimide (NHS) esters of PEG carboxylic acids, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. PEG-maleimide, PEG-vinylsulfone (VS), PEG-acrylate (AC) or PEG-orthopyridyl disulfide may be also used.

Serum albumin can also be engaged in half-life extension through modules with the capacity to non-covalently interact with albumin. In these approaches, an albumin-binding moiety is either conjugated or genetically fused to the therapeutic protein with albumin-binding activity are known from certain bacteria. For example, streptococcal protein G contains several small albumin-binding domains (ABD) composed of roughly 50 amino acid residues (6 kDa). Fusion of an ABD to a protein results in a strongly extended half-life (see Roland E Kontermann, trategies for extended serum half-life of protein therapeutics, Current Opinion in Biotechnology 2011, 22:868-876.

In some embodiments of the invention, the variant of the invention and IgG and/or any other protein that may be used for extending the half-life of the variant of the invention in the serum are linked by a linker. In Some embodiments of the invention, the linker is a sequence of between 2-20 amino acids.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

EXAMPLES

Example 1

Generation of Sema3C Cleavage-Resistant Variants

A polynucleotide construct encoding an un-cleavable variant of Sema 3C was generated in two steps:

1. Site directed mutagenesis was performed on a polynucleotide construct comprising the cDNA of Sema 3C as set forth in SEQ ID NO: 15 in order to generate a construct comprising cDNA encoding for a Sema 3C variant mutated at FPPC cleavage site 2.
2. The 3' of the cDNA encoding the resulting variant was truncated from nucleotide 2215, such that the resulting polynucleotide construct comprised a cDNA encoding for a Sema 3C variant which is mutated at site 2 and has a deletion of site 3 and the ADAMTS1 site.

Site Directed Mutagenesis:

Site directed mutagenesis was performed using the PfuUltraII DNA polymerase (Stratagene), according to the manufacturer's manual. In order to perform site directed mutagenesis each PCR tube contained: 10 ng DNA template (human Sema3C-wt cDNA, as set forth in SEQ ID NO: 15, in a pGEM-T easy plasmid), 1.25 ng of each primer as described below, 5 µl of 10× PfuUltraII DNA polymerase reaction buffer, 2.5 mM dNTPs, 1 µl PfuUltraII DNA polymerase and H$_2$O to a final volume of 50 µl. The PCR program used was: 95° C., 5 minutes, 95° C., 30 seconds, 48° C., 1.5 minute, 72° C., 10 minutes—back to step 2, ×25, 72° C., 5 minutes.

In order to digest the methylated template DNA, 1 µl of the DpnI restriction enzyme was added to each tube following the PCR reaction. Following the restriction digestion, the resulting DNA was transformed into XL-1 Blue competent cells. In order to generate a DNA construct comprising cDNA encoding for a Semaphorin 3C variant having site 2 mutated from RSRR (as set forth in SEQ ID NO: 3) to KSKK (as set forth in SEQ ID NO: 13), three additive rounds of mutagenesis were performed as follows:

1. Step 1—mutating FPPC site 2 having the amino acid sequence RSRR (as set forth in SEQ ID NO: 3) to a site having the amino acid sequence RSKR (as set forth in SEQ ID NO: 11), using the following primers and human Sema3C-wt cDNA as template:

```
5'-primer
                               (SEQ ID NO: 24)
GGGAAACGGAGGAGCAAAAGACAAGATGTGAGACATGG 3'-primer
                               (SEQ ID NO: 25)
CCATGTCTCACATCTTGTCTTTTGCTCCTCCGTTTCCC
```

2. Step 2—mutating the site having the amino acid sequence RSKR (as set forth in SEQ ID NO: 11) to a site having the amino acid sequence KSKR (as set forth in SEQ ID NO: 12), using the following primers and the construct generated in step 1 as template:

```
5'-primer
                               (SEQ ID NO: 26)
TACCCAACTGGGAAACGGAAGAGCAAAAGACAAGATGTGAGACATGG 3'-primer
                               (SEQ ID NO: 27)
CCATGTCTCACATCTTGTCTTTTGCTCTTCCGTTTCCCAGTTGGGTA
```

3. Step 3—mutating the site having the amino acid sequence KSKR (as set forth in SEQ ID NO: 12) to a site having the amino acid sequence KSKK (as set forth in SEQ ID NO: 13), using the following primers and the construct generated in step 2 as template:

```
5'-primer
                                           (SEQ ID NO: 28)
GGGAAACGGAAGAGCAAAAAACAAGATGTGAGACATGGAAACCC 3'-primer
                                           (SEQ ID NO: 29)
GGGTTTCCATGTCTCACATCTTGTTTTTTGCTCTTCCGTTTCCC
```

The resulting DNA construct comprised cDNA encoding a Sema 3C variant mutated in site 2, as set forth in SEQ ID NO: 10.

Truncation of the 3' end of Sema3C cDNA (as Set Forth in SEQ ID NO: 32) from Base 2215:

The DNA construct generated in step 3 above was further subjected to a PCR reaction using the following primers:

```
                                           (SEQ ID NO: 30)
1. 5'-primer CGGGATCCACCATGGCATCGGACAATTTG.
```

The BamHI restriction site is underlined.

2. 3'-primer CG CTCGAGACTATTGATGAGGGCCTTTAACTT (SEQ ID NO: 31). The XhoI restriction site is underlined.

The resulting PCR product was purified from agarose gel and ligated into a pGEM-T easy plasmid. The product was cut from the pGEM-T easy plasmid using the BamHI and XhoI restriction enzymes and ligated into either an NSPI-myc-6His plasmid or an NSPI-Fc plasmid. The resulting plasmids encoded, respectively:

1. UNCL-Sema3C/myc-6His—a variant of Sema 3C un-cleavable in site 2, having a C-terminal deletion comprising site 3 and the ADAMTS1 site and having a C-terminal myc-6His tag. The sequence of the resulting variant is as set forth in SEQ ID NO: 9. The cDNA encoding the resulting variant is as set forth in SEQ ID NO: 23.
2. UNCL-Sema3C/FC—a variant of Sema 3C un-cleavable in site 2, having a C-terminal deletion comprising site 3 and the ADAMTS1 site and having a C-terminal FC tag. The sequence of the resulting variant is as set forth in SEQ ID NO: 8. The cDNA encoding the resulting variant is as set forth in SEQ ID NO: 22.

FIG. 1A depicts wild-type Sema3C (indicated "Sema3C"), having all three FPPC cleavage sites and the basic domain (BD) intact. FIG. 1A further depicts UNCL-Sema3C/FC prepared as described herein above, having site 2 mutated from RSRR to KSKK, having a C-terminal truncation deleting site 3 and the ADAMTS1 site and having a C-terminal FC tag. As can be seen in FIG. 1A, site 1 in UNCL-Sema3C/FC is intact. FIG. 1B shows a western blot staining of conditioned media from HEK293 cells transfected with either an empty expression vector (NC), a construct encoding FC-tagged wild type Sema3C (Sema3C wt) or a construct encoding UNCL-Sema3C/FC (UNCL-Sema3C). As can be seen in FIG. 1B, a western blot using anti-FC antibodies showed that wild type Sema3C is cleaved to a 55 kDa form while UNCL-Sema3C/FC is not.

Example 2

Comparison of the Effect of Truncated Vs. Wild-Type Sema3C on in-Vitro Vessel Formation by Vascular Endothelial Cells In order to examine the effect of uncleavable Semaphorin 3C on angiogenesis, human umbilical vein-derived endothelial cells (HUVECs) were seeded in a liquid laminin/collagen gel (Matrigel). HUVECs seeded in a Matrigel are known to mimic human angiogenesis and to develop vessels within the Matrigel.

Figure 2:
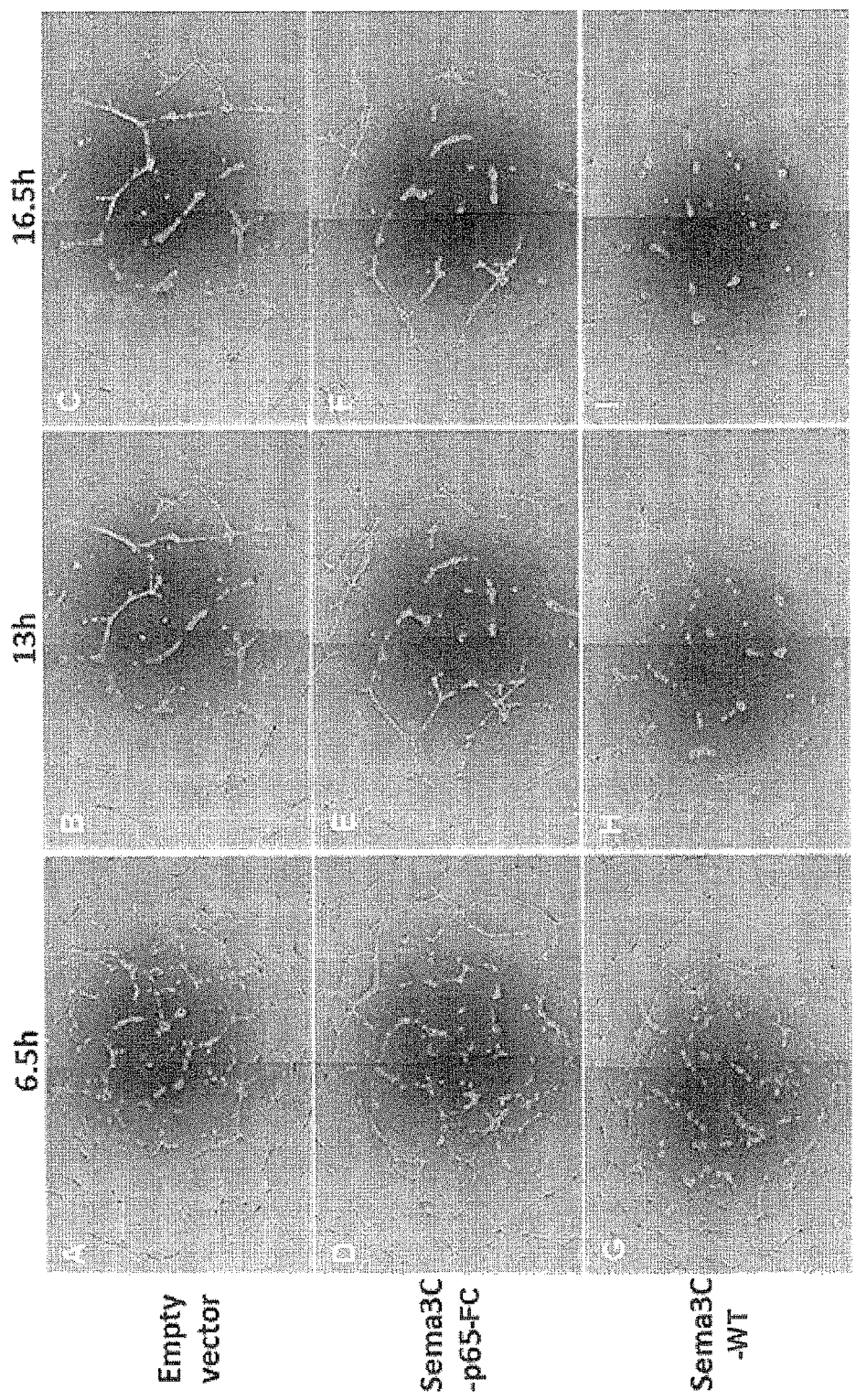
FIGS. 2A-I show micrographs depicting cultures of human umbilical vein-derived endothelial cells (HUVEC) which were incubated with conditioned media from HEK293 cells transfected with either an empty expression vector (FIGS. 2A-C, termed "Empty Vector"), a construct encoding an FC-tagged variant of Sema3C cleaved at FPPC site 2 (FIGS. 2D-F, termed "Sema3C-p65-FC") or a construct encoding FC-tagged wild type Sema3C (FIGS. 2G-I, termed "Sema3C-wt") at 6.5, 13 or 16.5 hours following incubation.

The cells were either left un-treated, treated with the N-terminal part of a Sema3C variant cleaved at site 2 and FC-tagged (termed Sema3C-p65-FC, as set forth in SEQ ID NO: 7) or treated with wild-type Sema3C (termed Sema 3C-WT). As can be seen in FIG. 2, the untreated cells and cells treated with Sema3C-p65-FC formed a network of tubes following incubation (FIGS. 2 B,C,E,F). In contrast, as can be seen in FIG. 2H-I, cells treated with wild-type Sema3C were contracted and failed to form tubes.

Example 3

Semaphorin 3C Induces Contraction of Lymphatic Endothelial Cells

In order to examine the effect of class 3 Semaphorins on lymphangiogenesis the LEC (Lymphatic Endothelial Cells) collapse assay was employed, monitoring the ability of semaphorins to induce LEC collapse. LECs were plated on gelatin coated cover slips (diameter 13 mm, thickness 1 mm), one day before the experiment, so that they would be 50-70% confluent at the day of experiment.

The experiment was initiated by a 25 min incubation of LECs at 37° C. with purified sema3E (1 µg/ml) or conditioned medium of HEK293 cells transfected with an empty vector or a construct encoding wild-type forms of either sema3A, sema3B, sema3C, sema3D, sema3F, sema3G or sema6A. The conditioned media were collected from $6 \times 10^6$ HEK293 cells 48 hours post-seeding. To verify that the semaphorins used are active, they were tested using a collapse assay on HUVEC (Human Vein Endothelial Cells) or human primary glioblastoma cells (U87, ATCC).

Following incubation, LECs were washed once in PBS and permeabilized in 0.5% Triton-X-100 diluted in 4% PFA for 2 minutes in room temperature. The cells were then fixed by incubation in 4% PFA at room temperature for 25 minutes and then washed 5 times in PBS. The cells were labeled with anti-vinculin antibody and diluted in PBS (1:100) at room temperature for 1 hour (20 µl of diluted antibody for each cover slip). The cells were then washed 3 times in PBS for 5 minutes and labeled with the mixture of anti-mouse Cy3 (secondary antibody for vinculin staining) (1:300) and Alexa Flour 488 Phalloidin (1:100, 2 units/ml) (to visualize actin filaments), diluted in PBS, for 45 minutes at room temperature in the dark (for sema3B, sema3D, sema3G, sema3E, sema6A). Or with Cy2 (1:300) and Phalloidin 570 (1:100, 2 units/ml), for sema3C, sema3F, sema3A, and the empty-vector control. The cells were then mounted using Mowiol mounting media (Calbiochem) on glass slides and photographed 24 hours after mounting using an inverted fluorescent microscope (LSM 700) at a 40× magnification.

Figure 3:
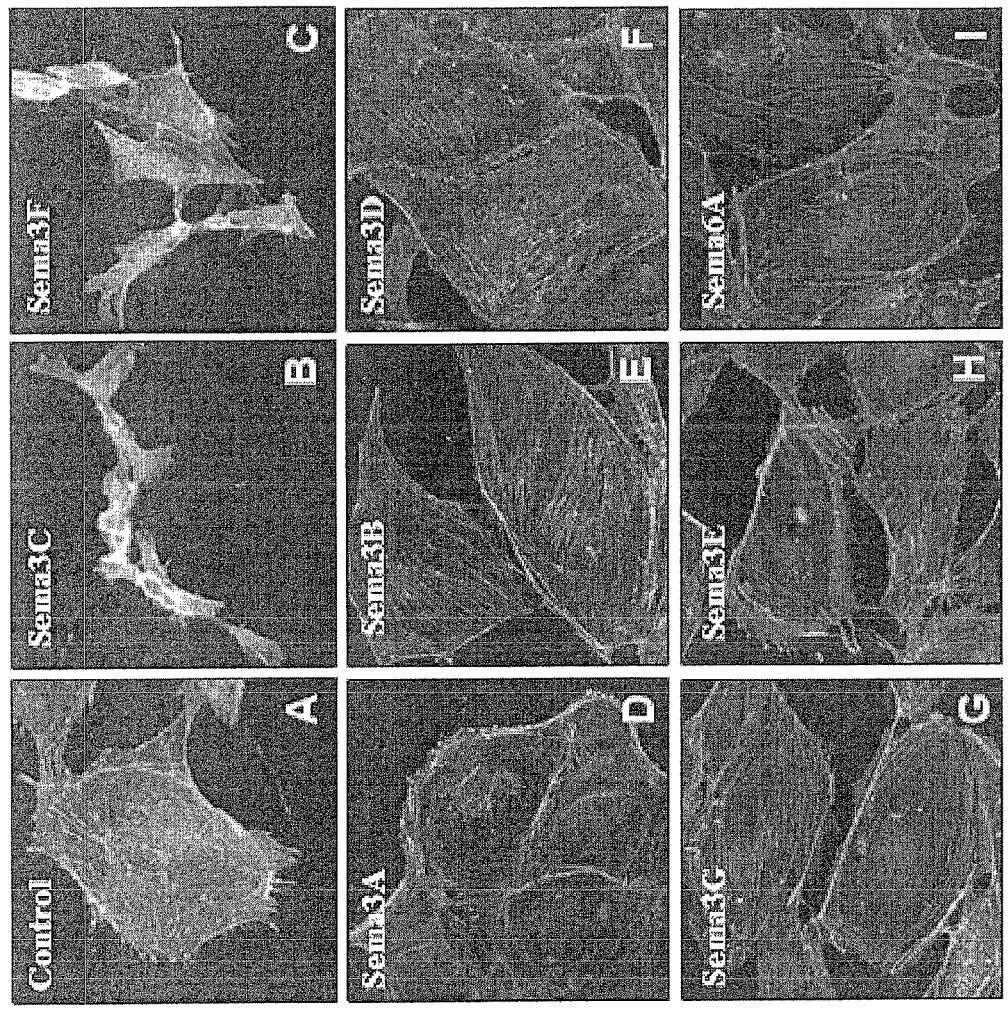
FIGS. 3A-I show micrographs depicting Lymphatic Endothelial Cells (LEC) which were treated for 30 min with purified sema3E (H) or conditioned medium of HEK293 cells transfected with an empty vector (A) or a construct encoding either sema3A (D), sema3B (E), sema3C (B), sema3D (F), sema3F (C), sema3G (G) or sema6A (I). After the semaphorin treatment the cells were fixed and immnostained for actin and vinculin.

As can be seen in FIG. 3, other than Sema 3F (FIG. 3C), previously suggested to inhibit lymphangiogenesis, only Sema 3C conditioned medium induced collapse of the cytoskeleton of Lymphatic Endothelial cells incubated with (FIG. 3B) as opposed to all other tested class 3 Semaphorins or medium conditioned by HEK293 cells transfected by an empty expression vector (FIG. 3A). The results suggest that Sema3C is able to inhibit lymphangiogenesis.

Example 4

Comparison of the Effect of Truncated Vs. Wild-Type Sema3C on Lymphatic Endothelial Cell (LEC) Contraction LECs were plated on gelatin coated cover slips (diameter 13 mm, thickness 1 mm) within 6-well plates, one day before the experiment, so that they would be 50-70% confluent at the day of experiment.

Figure 4:
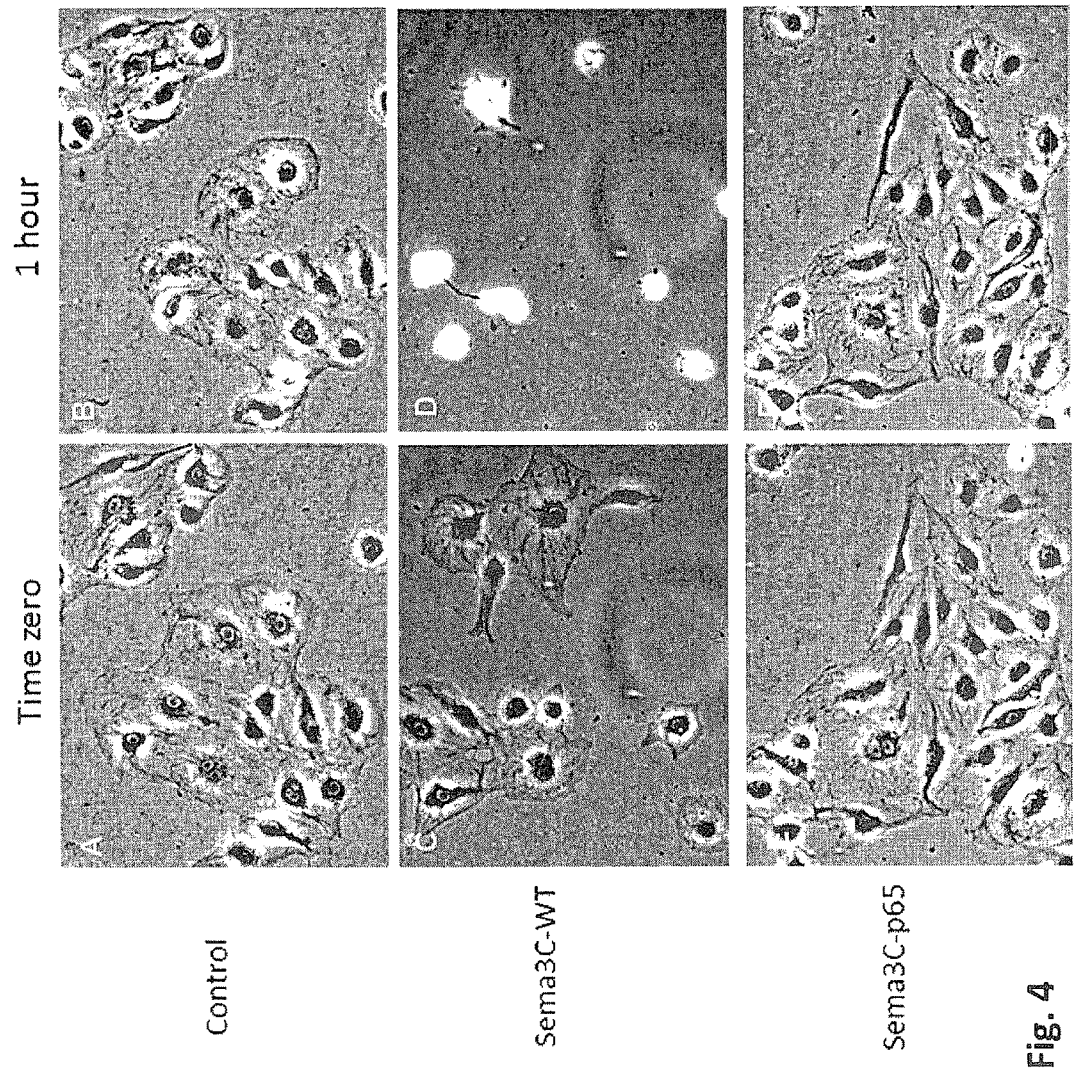
FIGS. 4A-F show micrographs depicting Lymphatic Endothelial Cells (LEC) which were incubated with conditioned media from HEK293 cells transfected with either an empty expression vector (FIGS. 4A-B, termed "Control"), a construct encoding FC-tagged wild type Sema3C (FIGS. 4C-D, termed "Sema3C-wt") or a construct encoding an FC-tagged variant of Sema3C cleaved at FPPC site 2 (FIGS.

LECs were incubated for 25 min at 37° C. with conditioned medium of HEK293 cells transfected with an empty vector or a construct encoding either FC-tagged wild-type sema3C (termed Sema3C-WT) or FC-tagged Sema3C-p65 variant (Sema3C truncated at site 2, termed Sema3C-p65). The Cells were photographed at the time the various conditioned media were added (time zero) and after 1 hour of incubation (1 hour). As can be seen in FIG. 4F, incubation with Sema3C-p65 did not induce LEC contraction, similarly to the control sample (FIG. 4B). Wild-type Sema3C, however, was able to induce LEC contraction (FIG. 4D).

Example 5

Unclevable Semaphorin 3C Prevents the Formation of Metastasis in Sentinel Lymph Nodes of Tumors Induced in Nude Mice In order to follow cancer cells within mice, LM2-4 cells (derived from highly metastatic MDA-MB-231 breast cancer cells) were infected with lentiviruses directing expression of Tomato-red fluorescent protein. Cells were then infected with empty lenti viruses (control cells) or with lenti viruses directing expression of UNCL-sema3C/Myc, as described in Example 1 (UNCL-Sema3C cells).

Control cells and UNCL-Sema3C cells from exponential cultures were dissociated with trypsin/EDTA, washed with PBS and brought to a concentration of $4 \times 10^7$ cells/ml. Each cell suspension ($2 \times 10^6$/0.05 ml) was inoculated in the right mammary fat pad of a 5-weeks old female NOD mice (n=7). After 31 days, mice were sacrificed and xenografts were resected, weighted and fixed in formalin. Sentinel lymph nodes (mesenteric) and axially lymph nodes were removed and photographed using an Olympus SZX9 fluorescent stereomicroscope to detect tomato red expressing cells that metastasized to the lymph node. All animal experiments were approved by the Animal Care Committee of the Technion, Haifa, Israel.

Tumors that developed from UNCL-Sema3C/Myc-expressing cells were about 40% smaller than tumors that developed from control cells. As can be seen in FIG. 5M, the weight of a tumor induced by UNCL-Sema3C cells (marked "Sema3C") was significantly lower (*=p<0.05) than a tumor induced by control cells (marked "control").

Figure 5:
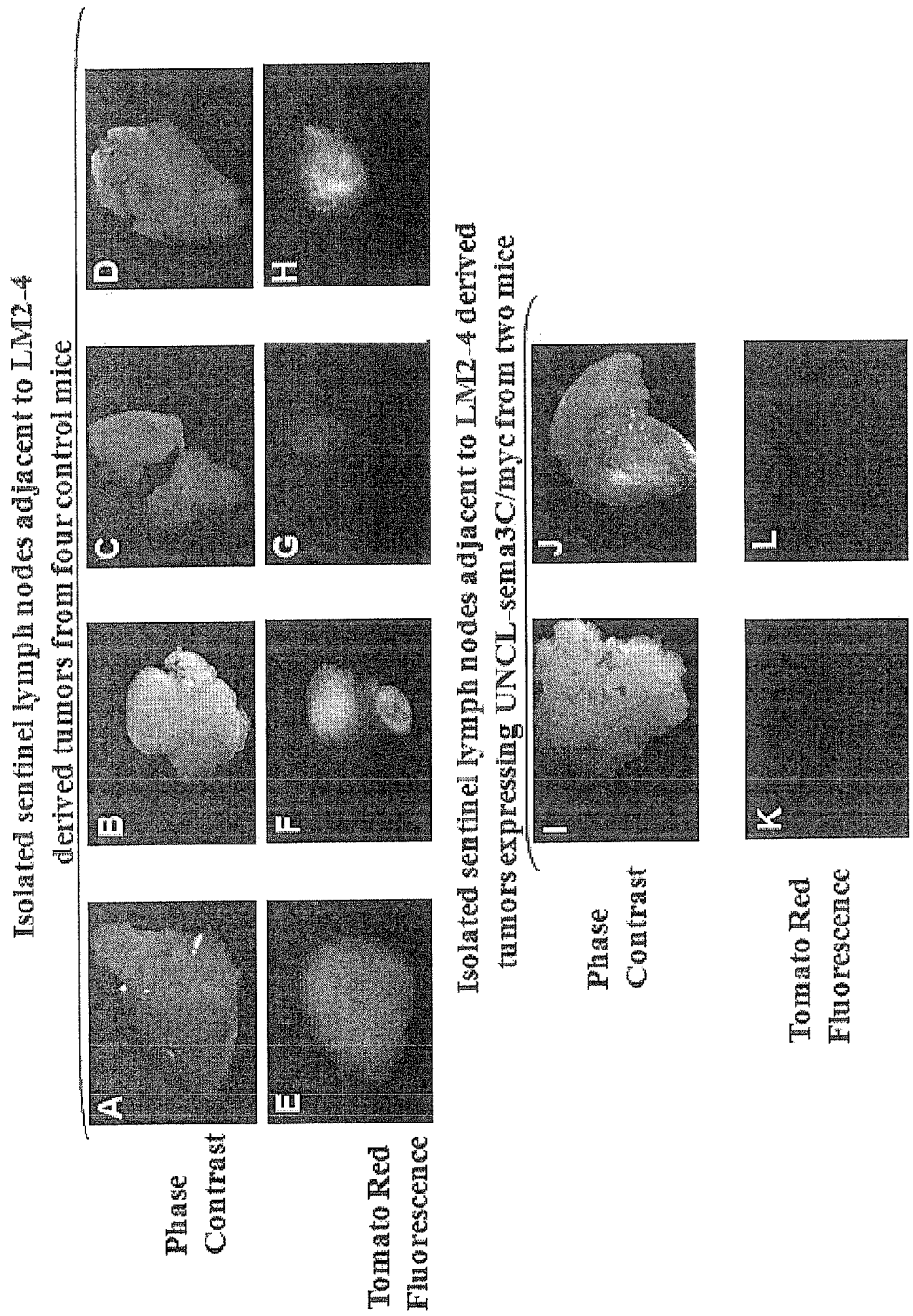
Figure 5M:
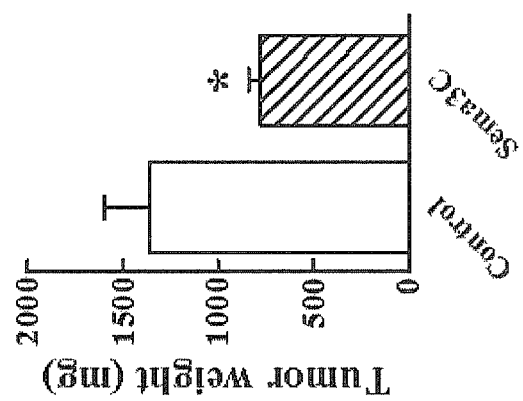
Figure 5M:
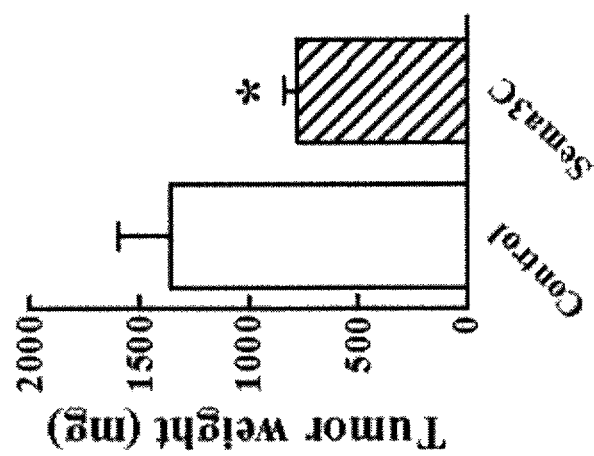

As can be seen in the fluorescent microscope images depicted in FIG. 5, a sentinel lymph nodes taken from an animal having UNCL-Sema3C/Myc-expressing tumors contained no Tomato-red fluorescent protein expressing cells as opposed to sentinel lymph nodes taken from control animals (FIGS. 5K-L and FIGS. 5E-H, respectively). FIGS. 5A-D and 5I-J depict phase contrast pictures of the sentinel lymph nodes depicted in FIGS. 5E-H and 5K-L, respectively.

Example 6

Unclevable Semaphorin 3C Reduces the Density of Tumor Associated Lymph Vessels Tumors formed using LM2-4 cells expressing either UNCL-sema3C/Myc or a control construct were formed in mice, as described in Example 5 (six mice in each group). The tumors were extracted as described in Example 5 and embedded in paraffin. In order to visualize the lymph nodes within the tumors, 5 micron thick sections covering the entire cross section of the tumors were stained for the lymph marker Lymphatic Vessel Endothelial Receptor 1 (LYVE-1) using an anti-LYVE-1 polyclonal antibody (Abcam Inc, Cambridge, Mass.) and the peroxidase-based EnVision™ kit (Daco). The area stained in microscopic fields of equal area covering the entire cross sections were determined using the ImagePro morphometric software. As can be seen in FIG. 6, the lymph node area in sections taken from tumors induced by UNCL-Sema3C/Myc expressing cells (marked "UNCL-Sema3C") was significantly lower (**=p<0.01) than the area in section taken from tumors induced by control cells (marked "Control").

Example 7

Unclevable Semaphorin 3C Reduces Tumor Weight Formed by VEGF-C-Expressing MDA-MB-231 Breast Cancer Cells MDA-MB-231 breast cancer cells were infected with lentiviruss expressing human VEGF-C (Vascular Endothelial Growth Factor C) protein. Following selection, a clone expressing high levels of VEGFC was infected with lentiviruses carrying either control or UNCL-sema3C/myc constructs, as described in Example 5. Cells expressing VEGF-C and either a control construct or UNCL-sema3C/myc were dissociated using trypsin/EDTA, washed with PBS and brought to a concentration of $1 \times 10^7$ cells/ml. Each cell suspension ($1 \times 10^6$/0.1 ml) was inoculated subcutaneously at the right flank of a 5-weeks old female Athymic nude mouse (n=6). After 41 days, mice were sacrificed and xenografts were resected, weighted and fixed in formalin. All animal experiments were approved by the Animal Care Committee of the Technion, Haifa, Israel. As can be seen in FIG. 7, the weight of tumors resulting from MDA-MB-231 cells expressing VEGF-C and UNCL-Sema3C/Myc (marked "VEGF-C+Sema3C") was significantly lower (*=p<0.05) than the weight of tumors resulting from cells expressing VEGF-C and the control construct (marked "VEGF-C+Control").

Example 8

Expression of Class-3 Semaphorin receptors in cultured Lymphatic Endothelial Cells (LEC) and cultured Human Umbilical Vein-derived Endothelial Cells (HUVEC)

In order to assay expression of Class-3 Semaphorin receptors a real-time PCR analysis was conducted. First, cDNAs from LEC and HUVEC were analyzed by AB StepOne Real-Time PCR system (Applied Biosystems) using a TaqMan Gene Expression Assay Mix (Applied Biosystems) specific for PlexinA1, PlexinA2, PlexinA3, PlexinA4, Plexin D1, NP1 and NP2 (hPlexinA1 HS00413698, hPlexinA2 HS00300697, hPlexinA3 HS00250178, hPlexinA4 HS00297356, hPlexinD1 HS00892410, hNP1 HS00826128, hNP2 HS00187290).

The TaqMan PCR reactions for each gene target were performed in duplicates on cDNA samples. For each 10 μl TaqMan reaction, 2.5 μl (25 ng) cDNA was mixed with 2 μl PCR-grade water, 5 μl 2×TaqMan Universal PCR Master Mix (Applied Biosystems) and 0.5 μl primer mix. The PCR parameters used were: 50° C. for 2 min, 95° C. for 10 min, 40 cycles of 95° C. for 15 s and 60° C. for 1 min. The reference gene human RPLPO (hRPLPO HS99999902), a standard endogenous control from ABI's Taqman gene expression assays, was multiplexed with the target gene for every cDNA template as a quality control measure. The resulting data was analyzed by the RQ Manager Software to obtain a relative quantification based on the arithmetical equation $2^{-\Delta Ct}$, in which $\Delta Ct$ is the normalized signal level in a sample relative to the RPLPO signal.

As can be seen in FIG. 8, LEC express NP2 but not NP1 or Plexin-A4. FIG. 8 further shows that LEC express very high levels of Plexin-A2 as compared to HUVEC (marked "HUE" in FIG. 8).

Example 9

UNCL-Sema3C-Fc Induces Collapse of the Cytoskeleton of Lymphatic Endothelial Cells (LECs)

In order to examine whether the ability of wild-type Sema 3C to in induce contraction of LECs is maintained in the cleavage resistant form of Sema3C, LECs were plated on cover slips within 12-well plates. Following 24 hours of incubation, the cells were incubated for 40 minutes at 37° C. with either purified UNCL-Sema3C-FC (SEQ ID NO: 8), purified Sema3C-p65-FC (SEQ ID NO: 7), purified Semaphorin 3E or elution buffer. The cells were then washed, fixed and stained with Phalloidin and an anti-Vinculin antibody, as described in Example 3. The cells were visualized using an inverted fluorescent microscope (LSM 700) at a 400× magnification.

Figure 9:
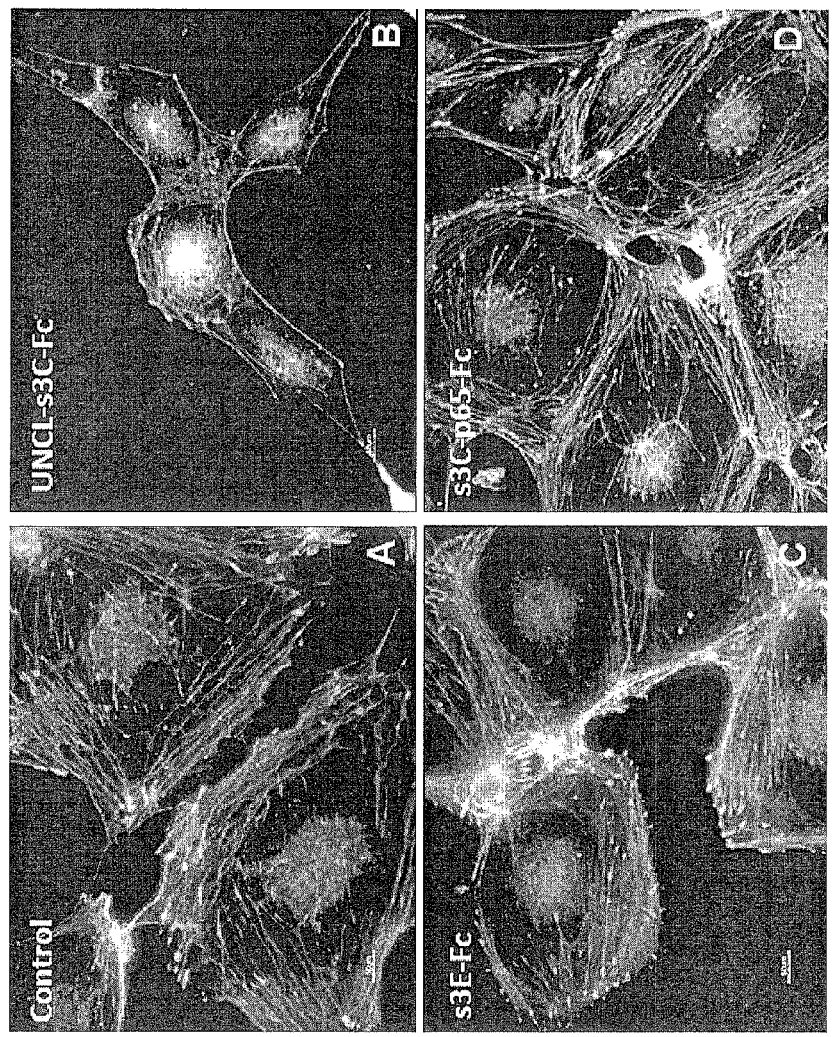

As can be seen in FIG. 9, UNCL-Sema3C-FC was able to induce cytoskeleton collapse in LECs (B), while cells incubated with elution buffer (A), Semaphorin 3E-FC (B) or Sema3C-p65-FC (D) were not able to induce cytoskeleton collapse. This result suggests that the ability of wild-type Semaphorin 3C to induce LEC collapse is derived from the activity of the uncleaved form of Sema 3C.

Example 10

Figure 10B:
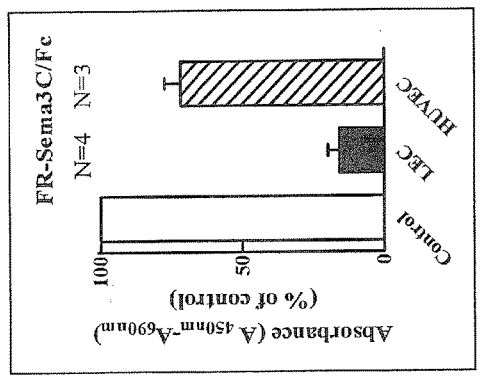
Figure 10A:
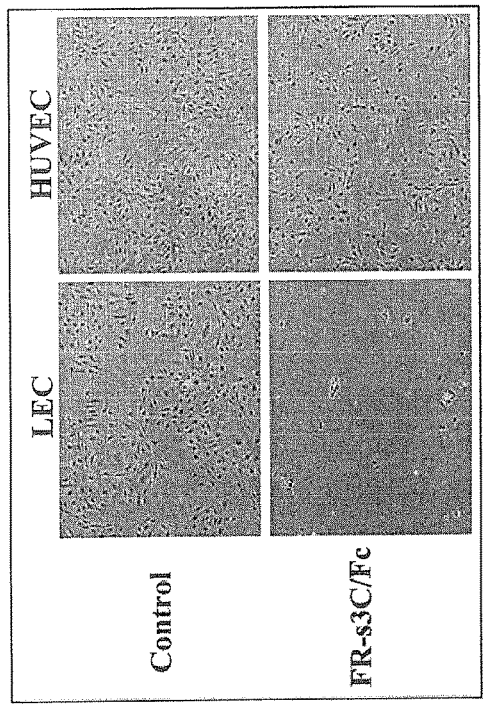

FR-Sema3C/Fc (Also Termed Herein UNCL-Sema3C/Fc–) Strongly Inhibits the Proliferation of LEC and VEGF-C Induced Signal Transduction To better characterize FR-sema3C, the effect of purified FR-sema3C/Fc on the proliferation of HUVEC and LEC was assessed. HUVEC (2×104 cells/well) or LEC (4×104 cells/well) were seeded in LEC medium in the presence or absence of semaphorins (2 µg/ml). Cells were photographed after 72 h. FR-sema3C/Fc inhibited strongly the proliferation of LEC and the cells eventually died. In contrast, although FR-sema3C/Fc inhibited the proliferation of HUVEC, the inhibition did not result in cell death and was much less potent that the inhibition of LEC proliferation (FIG. 10A). These results were confirmed by WST-1 proliferation kit. LEC and HUVEC were seeded in fibronectin coated 96 well dishes and the effect of FR-sema3C/Fc (2 µg/ml) on their proliferation was measured according to the instructions of the vendor. Shown is the average of N independent experiments (FIG. 10B).

Figure 10C:
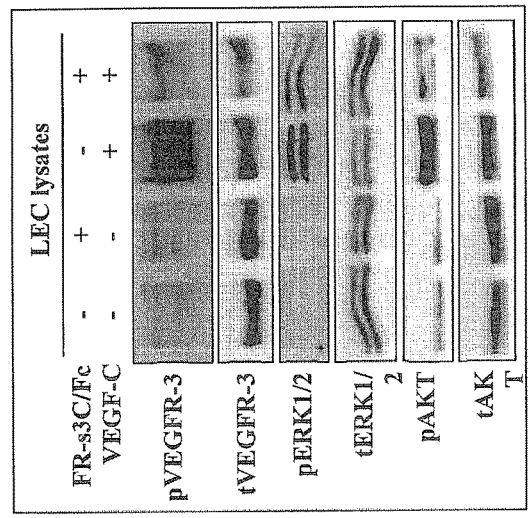
Figure 10E:
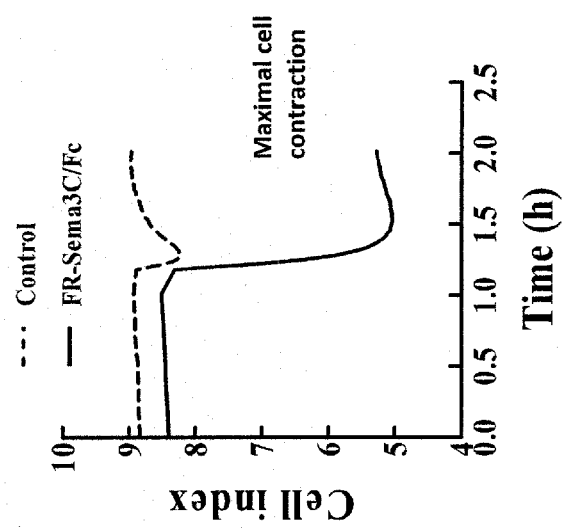
Figure 10D:
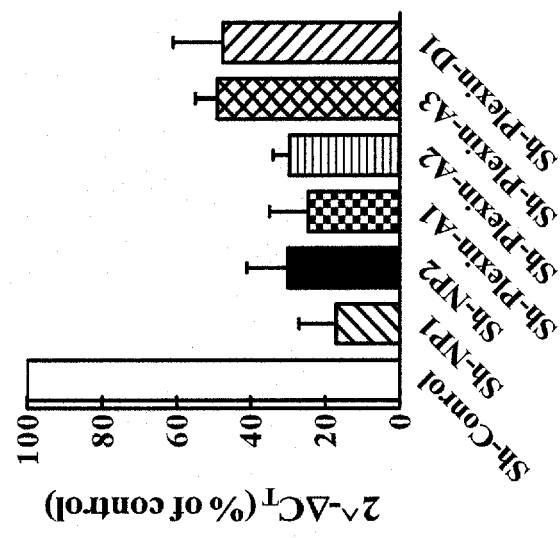

VEGF-C promotes the proliferation of LEC and is a potent lymphangiogenic factor. Accordingly the effect of FR-sema3C/Fc on VEGF-C induced signaling in LEC was assessed. LEC were grown to 90% confluence in growth medium and then shifted to LEC medium lacking growth factors and containing 0.5% FCS for 16 h. The cells were then incubated with vehicle or FR-sema3C/Fc (1 g/ml) for 15 minutes followed by a 10 min stimulation with VEGF-C (200 ng/ml). VEGFR-3, ERK1/2 and AKT phosphorylation levels were determined essentially as previously described for ERK1/2 phosphorylation. Stimulation by FR-sema3C/Fc inhibited VEGF-C induced phosphorylation of the VEGFR-3 receptor of LEC (Tyr-1230/1231), and also inhibited VEGF-C induced phosphorylation of ERK1/2 and Akt (FIG. 10C). These results suggest that FR-sema3C may inhibit the proliferation of LEC by inhibition of VEGF-C signaling and that FR-sema3C may compete with VEGF-C for binding to the VEGF-C co-receptor neuropilin-2 to inhibit the phosphorylation of VEGFR-3. To determine the relative contribution of the different neuropilins and plexins of LEC to FR-sema3C signal transduction the expression of these receptors in LEC was silenced (FIG. 10D) and the effects on FR-sema3C/Fc induced cell contraction were quantified using the xCELLigence dual plate (RTCA) machine as shown in FIG. 10E. The Inhibition of plexin expression with shRNA expressing lentiviruses was done by MISSION shRNA plasmids directing expression of various shRNAs that were purchased from Sigma Aldrich. The production of the lentiviruses in HEK293FT cells was performed as previously described (Varshaysky et al., 2008). LEC were seeded in 35 mm dishes, infected with the different silencing lentiviruses for 16 hours. 72 hours after infection the cells were used for contraction experiments and RNA silencing was detected by qRT-PCR. The plasmids purchased were: PlexinA1—TRCN0000078734, PlexinA2—TRCN0000061499, PlexinA3—TRCN0000047678, PlexinA4—TRCN0000078683, PlexinD1—TRCN0000061548, NP1—TRCN0000063526, NP2—TRCN0000063312 (Sigma Aldrich).

Figure 10F:
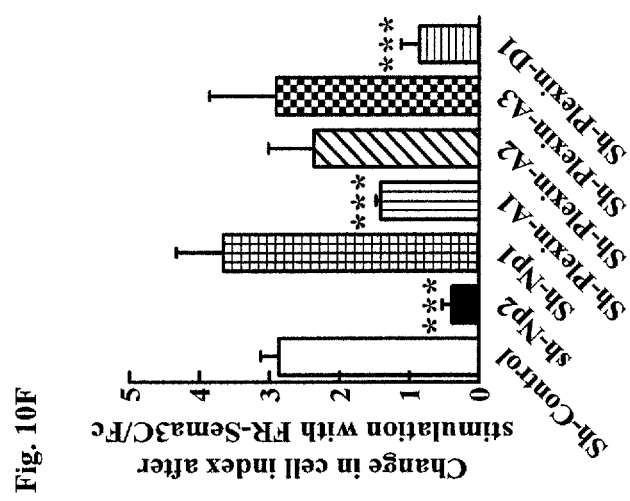

FR-sema3C/Fc induced contraction of the actin cytoskeleton of the LEC was strongly and significantly inhibited in LEC silenced for the expression of either neuropilin-2 (P<0.001), or plexin-D1 (P<0.001). FR-sema3C/Fc induced contraction was also inhibited by plexin-A1 silencing although somewhat less potently (P<0.001) while the silencing of neuropilin-1, and of the other plexins had no effect (FIG. 10F).

Example 11

Figure 11A:
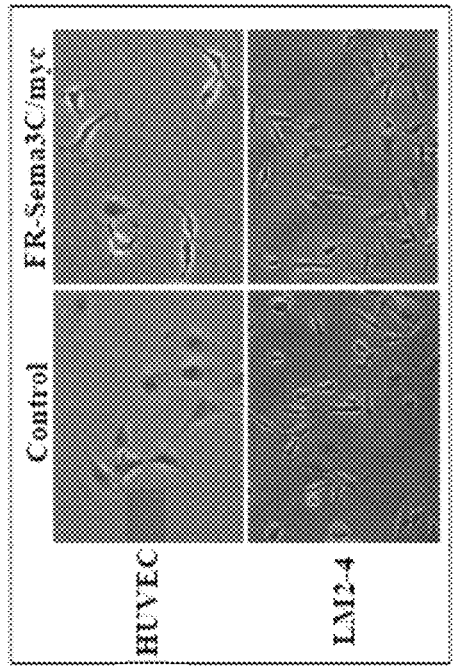
Figure 11B:
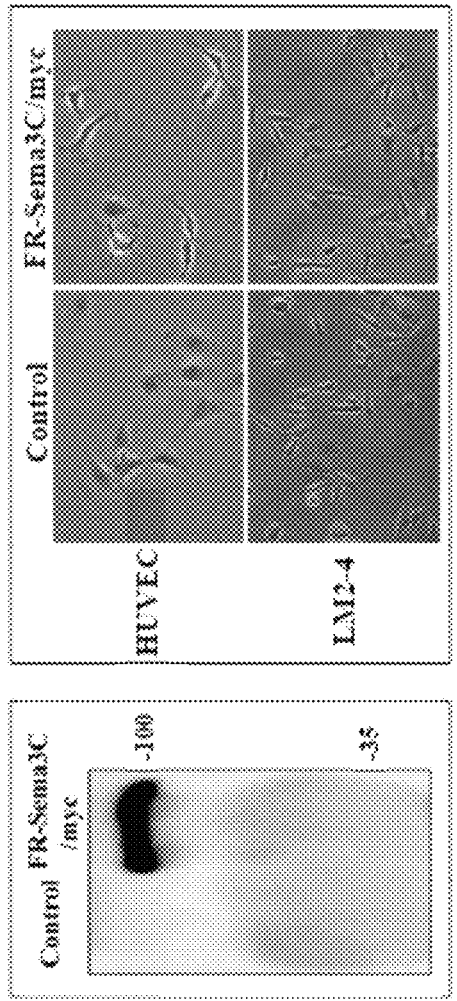
Figure 11C:
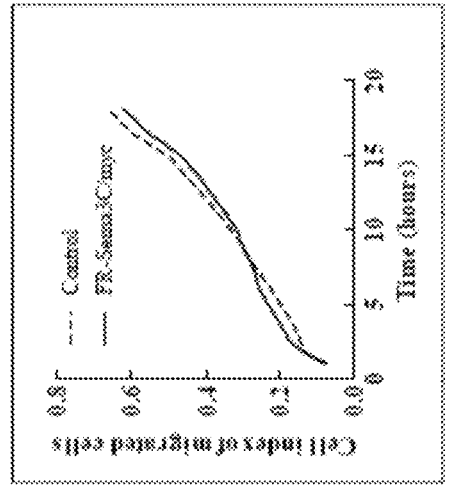
Figure 11D:
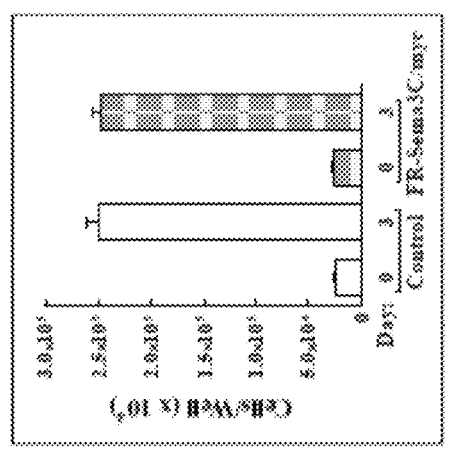

FR-Sema3C (Also Termed Here UNCL-Sema3C) does not Affect the Proliferation or Migration of LM2-4 Breast Cancer Cells but Strongly Inhibits the Progression of Tumors Derived from these Cells LM2-4 breast cancer cells were derived from triple negative MDA-MB-231 breast cancer cells by repeated isolation of metastasized cells from lungs. Recombinant tomato red RFP was expressed in them and in addition either empty expression vector (control) or FR-sema3C/myc. Conditioned medium from FR-sema3C/myc expressing LM2-4 cells contained almost exclusively full length FR-sema3C/myc (FIG. 11A). FR-sema3C/myc was biologically active and induced the contraction of HUVEC (FIG. 11B). However, FR-sema3C/myc failed to induce contraction of LM2-4 cells (FIG. 11B) nor expression of FR-sema3C/myc in the cells inhibit their proliferation or migration (FIGS. 11C & 11D). LM2-4 cells express neuropilin-1 and plexin-D1 but express very little neuropilin-2 which may perhaps explain why they do not respond to FR-sema3C/Fc (FIG. 11E). It is noted that FR-sema3C/myc is identical to FR-sema3C/myc6His.

Nevertheless, even though the expression of FR-sema3C/myc in LM2-4 cells did not change their behaviour in-vitro, expression of FR-sema3C/myc inhibited significantly (P=0.009) the development of tumors from these cells following their implantation in the mammary fat pads of scid/nod mice (FIG. 12A). Tomato red RFP expressing LM2-4 cells infected with empty lentiviral vector (control) or with lentiviruses directing expression of FR-sema3C/myc were washed, suspended in 50 μl of PBS and injected into the mammary fat pads of 6-7 week old female scid/nod mice (2×106 cells/mouse). Tumor size was monitored once a week. After 30 days, tumors and lymph nodes were excised and weighted. All the animal experiments were approved by the Technion ethics committee.

Figure 12G:
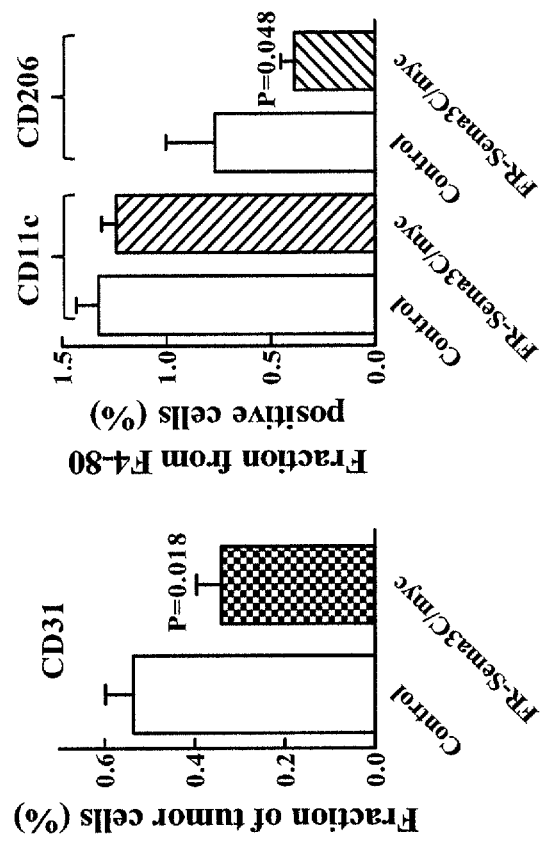
Figure 13B:
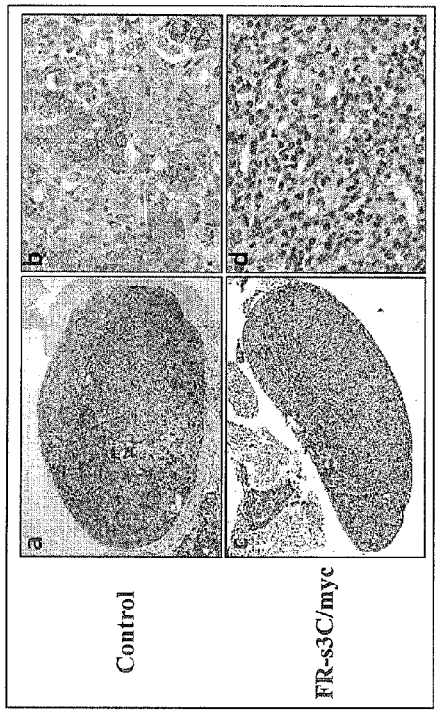
Figure 13D:
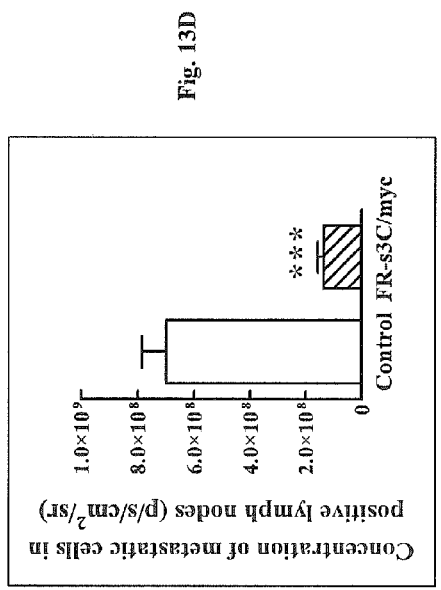
Figure 13A:
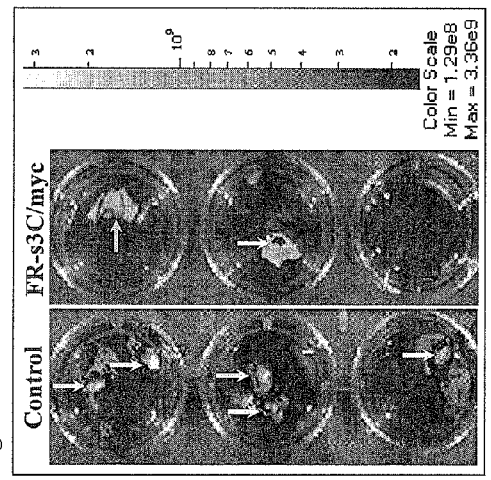
Figure 13C:
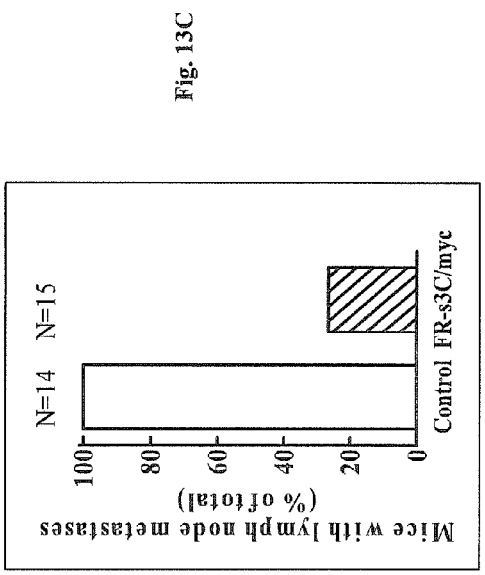

The density of lymph vessels in the primary tumors that developed from FR-sema3C/myc expressing cells was significantly lower (about ~50% lower, P=0.05) as compared to the density of lymph vessels in tumors that developed from control cells (FIGS. 12B & 12C), indicating that FR-sema3C/myc inhibits tumor lymphangiogenesis. In addition tumors derived from FR-sema3C/myc expressing LM2-4 cells also contained about half the density of blood vessels (P=0.05) as revealed by the staining of tumor sections with antibodies directed against CD31 (FIGS. 12D & 12E) should be and by FACS analysis (P=0.0018) (FIG. 12F) suggesting that FR-sema3C also functions as an inhibitor of tumor angiogenesis, which may explain why these tumors were smaller Notably, the density of blood vessels in control tumors was about 10 fold higher than the density of lymph vessels. The lymph vessels in the control tumors and in the tumors that developed from FR-sema3C/myc expressing cells were not present in necrotic regions but were present in all the other areas of the tumors. The concentration of tumor associated M1 and M2 macrophages using FACS analysis of single cell suspensions prepared from excised tumors was also determined. These experiments indicate that the concentration of the F4-80+/CD206+ positive M2 macrophage subpopulation is significantly reduced by about 50% in the FR-sema3C/myc expressing tumors (P=0.048) while the concentration of F4-80+/CD11-C+ M1 subpopulation was not altered (FIG. 12G). The proper axillary, lumbar aortic, and subiliac lymph nodes from mice harbouring tumors derived from control and FR-sema3C/myc expressing LM2-4 cells was excised Metastases in excised lymph nodes were detected using the IVIS-200 imaging system (FIG. 13A). The presence of metastases in lymph nodes was also verified by staining lymph node sections with antibodies directed against human class-1 HLA (FIG. 13B). While all the mice harbouring tumors derived from control cells developed metastases in their lymph nodes, only 26% of the mice harbouring tumors derived from FR-sema3C/myc expressing cells had lymph nodes that contained detectable metastases (FIG. 13C). Only 19% of the lymph nodes excised from mice harbouring FR-sema3C/myc expressing tumors contained detectable metastases while 70% of the lymph nodes excised from mice harbouring control tumors contained metastases. Furthermore, the average size of metastases found in lymph nodes of mice harbouring FR-sema3C/myc expressing tumors was only 15% of the average size of metastases found in lymph nodes derived from mice harbouring control tumors (P<0.001) (FIG. 13D). These results were obtained from three independent experiments. Taken together, these results suggest that FR-sema3C inhibits metastasis to lymph nodes.

Example 12

Use of FR-Sema3C (Also Termed Here UNCL-Sema3C) in Eye Diseases

Abnormal lymphangiogenesis is a complicating factor in additional diseases. Abnormal angiogenesis and lymphangiogenesis represents a complication of inflammatory several eye diseases in which new blood vessels and new lymph vessels invade the normally transparent cornea. This can be induced by irritants, limbal insufficiency, or complications of surgical procedures such cornea grafting and cause loss of vision. These observations suggest that inhibitors of lymphangiogenesis could be useful as drugs for the treatment of such eye diseases. Indeed, some inhibitors targeting the VEGFR-3 receptor which acts as the receptor for the lymphangiogenic factors VEGF-C and VEGF-D are currently in clinical trials. Accordingly, it is intended to determine if injection of FR-sema3C or application of eye drops containing FR-sema3C can be used to treat such corneal diseases in pre-clinical animal models.

Inflammation, neo-lymphangiogenesis and neo-angiogenesis will be induced in the corneas of eyes of c57 black mice or rat eyes using alkali burn or suture placement as described. FR-sema3C/Fc will be applied as drops or by injection in order to determine if it inhibits neo-angiogenesis and neo-lymphangiogenesis. Vehicle alone will be used as a control, and results will be compared to the effects of the VEGF inhibitor Avastin. A positive result will be a significant inhibition of lymphangiogenesis and angiogenesis to the cornea.

Sequence Table

| SEQ ID # | Sequenct Identity | Sequence |
|---|---|---|
| SEQ ID NO: 1 | Human wild-type Semaphorin 3C | MAFRTICVLVGVFICSICVKGSSQPQARVYLT FDELRETKTSEYFSLSHHPLDYRILLMDEDQD RIYVGSKDHILSLNINNISQEALSVFWPASTIK VEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKWT TFLKARLVCSVTDEDGPETHFDELEDVFLLE TDNPRTTLVYGIFTTSSSVFKGSAVCVYHLSD IQTVFNGPFAHKEGPNHQLISYQGRIPYPRPG TCPGGAFTPNMRTTKEFPDDVVTFIRNHPLM YNSIYPIHKRPLIVRIGTDYKYTKIAVDRVNA |

| SEQ ID # | Sequenct Identity | Sequence |
|---|---|---|
| | | ADGRYHVLFLGTDRGTVQKVVVLPTNNSVS<br>GELILEELEVFKNHAPITTMKISSKKQQLYVS<br>SNEGVSQVSLHRCHIYGTACADCCLARDPYC<br>AWDGHSCSRFYPTGKRRSRRQDVRHGNPLT<br>QCRGFNLKAYRNAAEIVQYGVKNNTTFLEC<br>APKSPQASIKWLLQKDKDRRKEVKLNERIIA<br>TSQGLLIRSVQGSDQGLYHCIATENSFKQTIA<br>KINFKVLDSEMVAVVTDKWSPWTWASSVR<br>ALPFHPKDIMGAFSHSEMQMINQYCKDTRQ<br>QHQQGDESQKMRGDYGKLKALINSRKSRNR<br>RNQLPES |
| SEQ ID NO: 2 | Furin-like pro-protein convertase cleavage site 1. Amino acids 144-147 of SEQ ID NO: 1. | RGRR |
| SEQ ID NO: 3 | Furin-like pro-protein convertase cleavage site 2. Amino acids 549-552 of SEQ ID NO: 1. | RSRR |
| SEQ ID NO: 4 | Furin-like pro-protein convertase cleavage site 3. Amino acids 742-745 of SEQ ID NO: 1. | RNRR |
| SEQ ID NO: 5 | The basic domain of Sema 3C. Amino acids 724-745 of SEQ ID NO: 1. | KMRGDYGKLKALINSRKSRNRR |
| SEQ ID NO: 6 | Sema 3C cleaved at site 2 (Sema 3C-p65) | MAFRTICVLVGVFICSICVKGSSQPQARVYLT<br>FDELRETKTSEYFSLSHHPLDYRILLMDEDQD<br>RIYVGSKDHILSLNINNISQEALSVFWPASTIK<br>VEECKMAGKDPTHGCGNFVRVIQTFNRTHL<br>YVCGSGAFSPVCTYLNRGRRSEDQVFMIDSK<br>CESGKGRCSFNPNVNTVSVMINEELFSGMYI<br>DFMGTDAAIFRSLTKRNAVRTDQHNSKWLS<br>EPMFVDAHVIPDGTDPNDAKVYFFFKEKLTD<br>NNRSTKQIHSMIARICPNDTGGLRSLVNKWT<br>TFLKARLVCSVTDEDGPETHFDELEDVFLLE<br>TDNPRTTLVYGIFTTSSSVFKGSAVCVYHLSD<br>IQTVFNGPFAHKEGPNHQLISYQGRIPYPRPG<br>TCPGGAFTPNMRTTKEFPDDVVTFIRNHPLM<br>YNSIYPIHKRPLIVRIGTDYKYTKIAVDRVNA<br>ADGRYHVLFLGTDRGTVQKVVVLPTNNSVS<br>GELILEELEVFKNHAPITTMKISSKKQQLYVS<br>SNEGVSQVSLHRCHIYGTACADCCLARDPYC<br>AWDGHSCSRFYPTGKR |
| SEQ ID NO: 7 | FC-tagged Sema 3C cleaved at site 2 (Sema 3 C-p65-FC) | MAFRTICVLVGVFICSICVKGSSQPQARVYLT<br>FDELRETKTSEYFSLSHHPLDYRILLMDEDQD<br>RIYVGSKDHILSLNINNISQEALSVFWPASTIK<br>VEECKMAGKDPTHGCGNFVRVIQTFNRTHL<br>YVCGSGAFSPVCTYLNRGRRSEDQVFMIDSK<br>CESGKGRCSFNPNVNTVSVMINEELFSGMYI<br>DFMGTDAAIFRSLTKRNAVRTDQHNSKWLS<br>EPMFVDAHVIPDGTDPNDAKVYFFFKEKLTD<br>NNRSTKQIHSMIARICPNDTGGLRSLVNKWT<br>TFLKARLVCSVTDEDGPETHFDELEDVFLLE<br>TDNPRTTLVYGIFTTSSSVFKGSAVCVYHLSD<br>IQTVFNGPFAHKEGPNHQLISYQGRIPYPRPG<br>TCPGGAFTPNMRTTKEFPDDVVTFIRNHPLM<br>YNSIYPIHKRPLIVRIGTDYKYTKIAVDRVNA<br>ADGRYHVLFLGTDRGTVQKVVVLPTNNSVS<br>GELILEELEVFKNHAPITTMKISSKKQQLYVS<br>SNEGVSQVSLHRCHIYGTACADCCLARDPYC<br>AWDGHSCSRFYPTGKRLEDKTHTCPPCPAPE<br>LLGGPSVFLFPPKPKDTLMISRTPEVTCVVVD<br>VSHEDPEVKFNWYVDGVEVHNAKTKPREEQ |

Sequence Table

| SEQ ID # | Sequenct Identity | Sequence |
|---|---|---|
| | | YNSTYRVVSVLTVLHQDWLNGKEYKCKVS NKALPAPIEKTISKAKGQPREPQVYTLPPSRE EMTKNQVSLTCLVKGFYPSDIAVEWESNGQP ENNYKTTPPVLDSDGSFFLYSKLTVDKSRWQ QGNVFSCSVMHEALHNHYTQKSLSLSPGK |
| SEQ ID NO: 8 | UNCL-Sema3C-Fc (as described in Example 1) | MAFRTICVLVGVFICSICVKGSSQPQARVYLT FDELRETKTSEYFSLSHHPLDYRILLMDEDQD RIYVGSKDHILSLNINNISQEALSVFWPASTIK VEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKW TTFLKARLVCSVTDEDGPETHFDELEDVFLL ETDNPRTTLVYGIFTTSSSVFKGSAVCVYHLS DIQTVFNGPFAHKEGPNHQLISYQGRIPYPRP GTCPGGAFTPNMRTTKEFPDDVVTFIRNHPL MYNSIYPIHKRPLIVRIGTDYKYTKIAVDRVN AADGRYHVLFLGTDRGTVQKVVVLPTNNSV SGELILEELEVFKNHAPITTMKISSKKQQLYV SSNEGVSQVSLHRCHIYGTACADCCLARDPY CAWDGHSCSRFYPTGKRKSKKQDVRHGNP LTQCRGFNLKAYRNAAEIVQYGVKNNTTFL ECAPKSPQASIKWLLQKDKDRRKEVKLNERI IATSQGLLIRSVQGSDQGLYHCIATENSFKQTI AKINFKVLDSEMVAVVTDKWSPWTWASSV RALPFHPKDIMGAFSHSEMQMINQYCKDTR QQHQQGDESQKMRGDYGKLKALINSLEDKT HTCPPCPAPELLGGPSVFLFPPKPKDTLMISRT PEVTCVVVDVSHEDPEVKFNWYVDGVEVH NAKTKPREEQYNSTYRVVSVLTVLHQDWLN GKEYKCKVSNKALPAPIEKTISKAKGQPREP QVYTLPPSREEMTKNQVSLTCLVKGFYPSDI AVEWESNGQPENNYKTTPPVLDSDGSFFLYS KLTVDKSRWQQG NVFSCSVMHEALHNHYTQKSLSLSPGK |
| SEQ ID NO: 9 | UNCL-Sema3C-myc-6His (as described in Example 1) | MAFRTICVLVGVFICSICVKGSSQPQARVYLT FDELRETKTSEYFSLSHHPLDYRILLMDEDQD RIYVGSKDHILSLNINNISQEALSVFWPASTIK VEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKW TTFLKARLVCSVTDEDGPETHFDELEDVFLL ETDNPRTTLVYGIFTTSSSVFKGSAVCVYHLS DIQTVFNGPFAHKEGPNHQLISYQGRIPYPRP GTCPGGAFTPNMRTTKEFPDDVVTFIRNHPL MYNSIYPIHKRPLIVRIGTDYKYTKIAVDRVN AADGRYHVLFLGTDRGTVQKVVVLPTNNSV SGELILEELEVFKNHAPITTMKISSKKQQLYV SSNEGVSQVSLHRCHIYGTACADCCLARDPY CAWDGHSCSRFYPTGKRKSKKQDVRHGNPL TQCRGFNLKAYRNAAEIVQYGVKNNTTFLE CAPKSPQASIKWLLQKDKDRRKEVKLNERII ATSQGLLIRSVQGSDQGLYHCIATENSFKQTI AKINFKVLDSEMVAVVTDKWSPWTWASSV RALPFHPKDIMGAFSHSEMQMINQYCKDTR QQHQQGDESQKMRGDYGKLKALINSLESRG PFEQKLISEEDLNMHTGHHHHHH |
| SEQ ID NO: 10 | Sema3C having cleavage site 2 modified to KSKK, preventing it from being cleaved at site 2 (As described in Example 1). | MAFRTICVLVGVFICSICVKGSSQPQARVYLT FDELRETKTSEYFSLSHHPLDYRILLMDEDQD RIYVGSKDHILSLNINNISQEALSVFWPASTIK VEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKWT |

Sequence Table

| SEQ ID # | Sequenct Identity | Sequence |
|---|---|---|
| | | TFLKARLVCSVTDEDGPETHFDELEDVFLLE TDNPRTTLVYGIFTTSSSVFKGSAVCVYHLSD IQTVFNGPFAHKEGPNHQLISYQGRIPYPRPG TCPGGAFTPNMRTTKEFPDDVVTFIRNHPLM YNSIYPIHKRPLIVRIGTDYKYTKIAVDRVNA ADGRYHVLFLGTDRGTVQKVVVLPTNNSVS GELILEELEVFKNHAPITTMKISSKKQQLYVS SNEGVSQVSLHRCHIYGTACADCCLARDPYC AWDGHSCSRFYPTGKRKSKKQDVRHGNPLT QCRGFNLKAYRNAAEIVQYGVKNNTTFLEC APKSPQASIKWLLQKDKDRRKEVKLNERIIA TSQGLLIRSVQGSDQGLYHCIATENSFKQTIA KINFKVLDSEMVAVVTDKWSPWTWASSVR ALPFHPKDIMGAFSHSEMQMINQYCKDTRQ QHQQGDESQKMRGDYGKLKALINSRKSRNR RNQLPES |
| SEQ ID NO: 11 | Site 2 after step 1 of mutagenesis, as described in Example 1 | RSKR |
| SEQ ID NO: 12 | Site 2 after steps 1 + 2 of mutagenesis, as described in Example 1 | KSKR |
| SEQ ID NO: 13 | Mutated un-cleavable site 2 after steps 1-3 of mutagenesis, as described in Example 1 | KSKK |
| SEQ ID NO: 14 | FC-tagged Human wild-type Semaphorin 3C | MAFRTICVLVGVFICSICVKGSSQPQARVYLT FDELRETKTSEYFSLSHHPLDYRILLMDEDQD RIYVGSKDHILSLNINNISQEALSVFWPASTIK VEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKWT TFLKARLVCSVTDEDGPETHFDELEDVFLLE TDNPRTTLVYGIFTTSSSVFKGSAVCVYHLSD IQTVFNGPFAHKEGPNHQLISYQGRIPYPRPG TCPGGAFTPNMRTTKEFPDDVVTFIRNHPLM YNSIYPIHKRPLIVRIGTDYKYTKIAVDRVNA ADGRYHVLFLGTDRGTVQKVVVLPTNNSVS GELILEELEVFKNHAPITTMKISSKKQQLYVS SNEGVSQVSLHRCHIYGTACADCCLARDPYC AWDGHSCSRFYPTGKRRSRRQDVRHGNPLT QCRGFNLKAYRNAAEIVQYGVKNNTTFLEC APKSPQASIKWLLQKDKDRRKEVKLNERIIA TSQGLLIRSVQGSDQGLYHCIATENSFKQTIA KINFKVLDSEMVAVVTDKWSPWTWASSVR ALPFHPKDIMGAFSHSEMQMINQYCKDTRQ QHQQGDESQKMRGDYGKLKALINSRKSRNR RNQLPESLEDKTHTCPPCPAPELLGGPSVFLF PPKPKDTLMISRTPEVTCVVVDVSHEDPEVK FNWYVDGVEVHNAKTKPREEQYNSTYRVVS VLTVLHQDWLNGKEYKCKVSNKALPAPIEK TISKAKGQPREPQVYTLPPSREEMTKNQVSL TCLVKGFYPSDIAVEWESNGQPENNYKTTPP VLDSDGSFFLYSKLTVDKSRWQQGNVFSCSV MHEALHNHYTQKSLSLSPGK |
| SEQ ID NO: 15 | cDNA corresponding to human wild-type Semaphorin 3C (SEQ ID NO: 1) | ATGGCATTCCGGACAATTTGCGTGTTGGTT GGAGTATTTATTTGTTCTATCTGTGTGAAA GGATCTTCCCAGCCCCAAGCAAGAGTTTAT TTAACATTTGATGAACTTCGAGAAACCAAG ACCTCTGAATACTTCAGCCTTTCCCACCAT CCTTTAGACTACAGGATTTTATTAATGGAT GAAGATCAGGACCGGATATATGTGGGAAG CAAAGATCACATTCTTTCCCTGAATATTAA |

Sequence Table

| SEQ ID # | Sequenct Identity | Sequence |
|---|---|---|
| | | CAATATAAGTCAAGAAGCTTTGAGTGTTTT |
| | | CTGGCCAGCATCTACAATCAAAGTTGAAG |
| | | AATGCAAAATGGCTGGCAAAGATCCCACA |
| | | CACGGCTGTGGGAACTTTGTCCGTGTAATT |
| | | CAGACTTTCAATCGCACACATTTGTATGTC |
| | | TGTGGGAGTGGCGCTTTCAGTCCTGTCTGT |
| | | ACTTACTTGAACAGAGGGAGGAGATCAGA |
| | | GGACCAAGTTTTCATGATTGACTCCAAGTG |
| | | TGAATCTGGAAAAGGACGCTGCTCTTTCAA |
| | | CCCCAACGTGAACACGGTGTCTGTTATGAT |
| | | CAATGAGGAGCTTTTCTCTGGAATGTATAT |
| | | AGATTTCATGGGACAGATGCTGCTATTTT |
| | | TCGAAGTTTAACCAAGAGGAATGCGGTCA |
| | | GAACTGATCAACATAATTCCAAATGGCTAA |
| | | GTGAACCTATGTTTGTAGATGCACATGTCA |
| | | TCCCAGATGGTACTGATCCAAATGATGCTA |
| | | AGGTGTACTTCTTCTTCAAAGAAAAACTGA |
| | | CTGACAATAACAGGAGCACGAAACAGATT |
| | | CATTCCATGATTGCTCGAATATGTCCTAAT |
| | | GACACTGGTGGACTGCGTAGCCTTGTCAAC |
| | | AAGTGGACCACTTTCTTAAAGGCGAGGCTG |
| | | GTGTGCTCGGTAACAGATGAAGACGGCCC |
| | | AGAAACACACTTTGATGAATTAGAGGATG |
| | | TGTTTCTGCTGGAAACTGATAACCCGAGGA |
| | | CAACACTAGTGTATGGCATTTTTACAACAT |
| | | CAAGCTCAGTTTTCAAAGGATCAGCCGTGT |
| | | GTGTGTATCATTTATCTGATATACAGACTG |
| | | TGTTTAATGGGCCTTTTGCCCACAAAGAAG |
| | | GGCCCAATCATCAGCTGATTTCCTATCAGG |
| | | GCAGAATTCCATATCCTCGCCCTGGAACTT |
| | | GTCCAGGAGGAGCATTTACACCCAATATGC |
| | | GAACCACCAAGGAGTTCCCAGATGATGTT |
| | | GTCACTTTTATTCGGAACCATCCTCTCATGT |
| | | ACAATTCCATCTACCCAATCCACAAAAGGC |
| | | CTTTGATTGTTCGTATTGGCACTGACTACA |
| | | AGTATACAAAGATAGCTGTGGATCGAGTG |
| | | AACGCTGCTGATGGGAGATACCATGTCCTG |
| | | TTTCTCGGAACAGATCGGGGTACTGTGCAA |
| | | AAAGTGGTTGTTCTTCCTACTAACAACTCT |
| | | GTCAGTGGCGAGCTCATTCTGGAGGAGCTG |
| | | GAAGTCTTTAAGAATCATGCTCCTATAACA |
| | | ACAATGAAAATTTCATCTAAAAAGCAACA |
| | | GTTGTATGTGAGTTCCAATGAAGGGGTTTC |
| | | CCAGGTATCTCTGCACCGCTGCCACATCTA |
| | | TGGTACAGCCTGTGCTGACTGCTGCCTGGC |
| | | GCGGGACCCTTATTGCGCCTGGGATGGCCA |
| | | TTCCTGTTCCAGATTCTACCCAACTGGGAA |
| | | ACGGAGGAGCCGAAGACAAGATGTGAGAC |
| | | ATGGAAACCCACTGACTCAATGCAGAGGA |
| | | TTTAATCTAAAAGCATACAGAAATGCAGCT |
| | | GAAATTGTGCAGTATGGAGTAAAAAATAA |
| | | CACCACTTTTCTGGAGTGTGCCCCCAAGTC |
| | | TCCGCAGGCATCTATCAAGTGGCTGTTACA |
| | | GAAAGACAAAGACAGGAGGAAAGAGGTT |
| | | AAGCTGAATGAACGAATAATAGCCACTTC |
| | | ACAGGGACTCCTGATCCGCTCTGTTCAGGG |
| | | TTCTGACCAAGGACTTTATCACTGCATTGC |
| | | TACAGAAAATAGTTTCAAGCAGACCATAG |
| | | CCAAGATCAACTTCAAAGTTTTAGATTCAG |
| | | AAATGGTGGCTGTTGTGACGGACAAATGG |
| | | TCCCCATGGACCTGGGCCAGCTCTGTGAGG |
| | | GCTTTACCCTTCCACCCGAAGGACATCATG |
| | | GGGGCATTCAGCCACTCAGAAATGCAGAT |
| | | GATTAACCAATATTGCAAAGACACTCGGC |
| | | AGCAACATCAGCAGGGAGATGAATCACAG |
| | | AAAATGAGAGGGGACTATGGCAAGTTAAA |
| | | GGCCCTCATCAATAGTCGGAAAAGTAGAA |
| | | ACAGGAGGAATCAGTTGCCAGAGTCATAA |

-continued

| Sequence Table | | |
|---|---|---|
| SEQ ID # | Sequenct Identity | Sequence |
| SEQ ID NO: 16 | Polynucleotide sequence corresponding to site 1 of Sema3C. Bases 430-441 of SEQ ID NO: 15. | AGAGGGAGGAGA |
| SEQ ID NO: 17 | Polynucleotide sequence corresponding to site 2 of Sema3C. Bases 1645-1656 of SEQ ID NO: 15. | AGGAGCCGAAGA |
| SEQ ID NO: 18 | Polynucleotide sequence corresponding to site 3 of Sema3C. Bases 2224-2235 of SEQ ID NO: 15. | AGAAACAGGAGG |
| SEQ ID NO: 19 | Polynucleotide sequence corresponding to basic domain of Sema3C (SEQ ID NO: 5) | AAAATGAGAGGGGACTATGGCAAGTTAAA GGCCCTCATCAATAGTCGGAAAAGTAGAA ACAGGAGG |
| SEQ ID NO: 20 | cDNA sequence of Sema3C-p65 (SEQ ID NO: 6) | ATGGCATTCCGGACAATTTGCGTGTTGGTT GGAGTATTTATTTGTTCTATCTGTGTGAAA GGATCTTCCCAGCCCCAAGCAAGAGTTTAT TTAACATTTGATGAACTTCGAGAAACCAAG ACCTCTGAATACTTCAGCCTTTCCCACCAT CCTTTAGACTACAGGATTTTATTAATGGAT GAAGATCAGGACCGGATATATGTGGGAAG CAAAGATCACATTCTTTCCCTGAATATTAA CAATATAAGTCAAGAAGCTTTGAGTGTTTT CTGGCCAGCATCTACAATCAAAGTTGAAG AATGCAAAATGGCTGGCAAAGATCCCACA CACGGCTGTGGGAACTTTGTCCGTGTAATT CAGACTTTCAATCGCACACATTTGTATGTC TGTGGGAGTGGCGCTTTCAGTCCTGTCTGT ACTTACTTGAACAGAGGGAGGAGATCAGA GGACCAAGTTTTCATGATTGACTCCAAGTG TGAATCTGGAAAAGGACGCTGCTCTTTCAA CCCCAACGTGAACACGGTGTCTGTTATGAT CAATGAGGAGCTTTTCTCTGGAATGTATAT AGATTTCATGGGGACAGATGCTGCTATTTT TCGAAGTTTAACCAAGAGGAATGCGGTCA GAACTGATCAACATAATTCCAAATGGCTAA GTGAACCTATGTTTGTAGATGCACATGTCA TCCCAGATGGTACTGATCCAAATGATGCTA AGGTGTACTTCTTCTTCAAAGAAAAACTGA CTGACAATAACAGGAGCACGAAACAGATT CATTCCATGATTGCTCGAATATGTCCTAAT GACACTGGTGGACTGCGTAGCCTTGTCAAC AAGTGGACCACTTTCTTAAAGGCGAGGCTG GTGTGCTCGGTAACAGATGAAGACGGCCC AGAAACACACTTTGATGAATTAGAGGATG TGTTTCTGCTGGAAACTGATAACCCGAGGA CAACACTAGTGTATGGCATTTTTACAACAT CAAGCTCAGTTTTCAAAGGATCAGCCGTGT GTGTGTATCATTTATCTGATATACAGACTG TGTTTAATGGCCTTTTGCCCACAAAGAAG GGCCCAATCATCAGCTGATTTCCTATCAGG GCAGAATTCCATATCCTCGCCCTGGAACTT GTCCAGGAGGAGCATTTACACCCAATATGC GAACCACCAAGGAGTTCCCAGATGATGTT GTCACTTTTATTCGGAACCATCCTCTCATGT ACAATTCCATCTACCCAATCCACAAAAGGC CTTTGATTGTTCGTATTGGCACTGACTACA AGTATACAAAGATAGCTGTGGATCGAGTG AACGCTGCTGATGGGAGATACCATGTCCTG |

Sequence Table

| SEQ ID # | Sequenct Identity | Sequence |
|---|---|---|
| | | TTTCTCGGAACAGATCGGGGTACTGTGCAA AAAGTGGTTGTTCTTCCTACTAACAACTCT GTCAGTGGCGAGCTCATTCTGGAGGAGCTG GAAGTCTTTAAGAATCATGCTCCTATAACA ACAATGAAAATTTCATCTAAAAAGCAACA GTTGTATGTGAGTTCCAATGAAGGGGTTTC CCAGGTATCTCTGCACCGCTGCCACATCTA TGGTACAGCCTGTGCTGACTGCTGCCTGGC GCGGGACCCTTATTGCGCCTGGGATGGCCA TTCCTGTTCCAGATTCTACCCAACTGGGAA ACGG |
| SEQ ID NO: 21 | cDNA sequence of Sema3C-p65-FC (SEQ ID NO: 7) | ATGGCATTCCGGACAATTTGCGTGTTGGTT GGAGTATTTATTTGTTCTATCTGTGTGAAA GGATCTTCCCAGCCCCAAGCAAGAGTTTAT TTAACATTTGATGAACTTCGAGAAACCAAG ACCTCTGAATACTTCAGCCTTTCCCACCAT CCTTTAGACTACAGGATTTTATTAATGGAT GAAGATCAGGACCGGATATATGTGGGAAG CAAAGATCACATTCTTTCCCTGAATATTAA CAATATAAGTCAAGAAGCTTTGAGTGTTTT CTGGCCAGCATCTACAATCAAAGTTGAAG AATGCAAAATGGCTGGCAAAGATCCCACA CACGGCTGTGGGAACTTTGTCCGTGTAATT CAGACTTTCAATCGCACACATTTGTATGTC TGTGGGAGTGGCGCTTTCAGTCCTGTCTGT ACTTACTTGAACAGAGGGAGGAGATCAGA GGACCAAGTTTTCATGATTGACTCCAAGTG TGAATCTGGAAAAGGACGCTGCTCTTTCAA CCCCAACGTGAACACGGTGTCTGTTATGAT CAATGAGGAGCTTTCTCTGGAATGTATAT AGATTTCATGGGACAGATGCTGCTATTTT TCGAAGTTTAACCAAGAGGAATGCGGTCA GAACTGATCAACATAATTCCAAATGGCTAA GTGAACCTATGTTTGTAGATGCACATGTCA TCCCAGATGGTACTGATCCAAATGATGCTA AGGTGTACTTCTTCTTCAAAGAAAAACTGA CTGACAATAACAGGAGCACGAAACAGATT CATTCCATGATTGCTCGAATATGTCCTAAT GACACTGGTGGACTGCGTAGCCTTGTCAAC AAGTGGACCACTTTCTTAAAGGCGAGGCTG GTGTGCTCGGTAACAGATGAAGACGGCCC AGAAACACACTTTGATGAATTAGAGGATG TGTTTCTGCTGGAAACTGATAACCCGAGGA CAACACTAGTGTATGGCATTTTTACAACAT CAAGCTCAGTTTTCAAAGGATCAGCCGTGT GTGTGTATCATTTATCTGATATACAGACTG TGTTTAATGGGCCTTTTGCCCACAAAGAAG GGCCCAATCATCAGCTGATTTCCTATCAGG GCAGAATTCCATATCCTCGCCCTGGAACTT GTCCAGGAGGAGCATTTACACCCAATATGC GAACCACCAAGGAGTTCCCAGATGATGTT GTCACTTTTATTCGGAACCATCCTCTCATGT ACAATTCCATCTACCCAATCCACAAAAGGC CTTTGATTGTTCGTATTGCjCACTGACTACA ACTATACAAAGATAGCTGTGGATCGAGTG AACGCTGCTGATGGGAGATACCATGTCCTG TTTCTCGGAACAGATCGGGGTACTGTGCAA AAAGTGGTTGTTCTTCCTACTAACAACTCT GTCAGTGGCGAGCTCATTCTGGAGGAGCTG GAAGTCTTTAAGAATCATGCTCCTATAACA ACAATGAAAATTTCATCTAAAAAGCAACA GTTGTATGTGAGTTCCAATGAAGGGGTTTC CCAGGTATCTCTGCACCGCTGCCACATCTA TGGTACAGCCTGTGCTGACTGCTGCCTGGC GCGGGACCCTTATTGCGCCTGGGATGGCCA TTCCTGTTCCAGATTCTACCCAACTGGGAA ACGGCTCGAGGACAAAACTCACACATGCC CACCGTGCCCAGCACCTGAACTCCTGGGGG GACCGTCAGTCTTCCTCTTCCCCCCAAAAC CCAAGGACACCCTCATGATCTCCCGGACCC CTGAGGTCACATGCGTGGTGGTGGACGTG AGCCACGAAGACCCTGAGGTCAAGTTCAA CTGGTACGTGGACGGCGTGGAGGTGCATA |

Sequence Table

| SEQ ID # | Sequenct Identity | Sequence |
|---|---|---|
| | | ATGCCAAGACAAAGCCGCGGGAGGAGCAG<br>TACAACAGCACGTACCGTGTGGTCAGCGTC<br>CTCACCGTCCTGCACCAGGACTGGCTGAAT<br>GGCAAGGAGTACAAGTGCAAGGTCTCCAA<br>CAAAGCCCTCCCAGCCCCCATCGAGAAAA<br>CCATCTCCAAAGCCAAAGGGCAGCCCCGA<br>GAACCACAGGTGTACACCCTGCCCCCATCC<br>CGGGAGGAGATGACCAAGAACCAGGTCAG<br>CCTGACCTGCCTGGTCAAAGGCTTCTATCC<br>CAGCGACATCGCCGTGGAGTGGGAGAGCA<br>ATGGGCAGCCGGAGAACAACTACAAGACC<br>ACGCCTCCCGTGCTGGACTCCGACGGCTCC<br>TTCTTCCTCTATAGCAAGCTCACCGTGGAC<br>AAGAGCAGGTGGCAGCAGGGGAACGTCTT<br>CTCATGCTCCGTGATGCATGAGGCTCTGCA<br>CAACCACTACACGCAGAAGAGCCTCTCCCT<br>GTCCCCGGGTAAATGA |
| SEQ ID NO: 22 | cDNA sequence of UNCL-Sema3C-Fc (SEQ ID NO: 8) | ATGGCATTCCGGACAATTTGCGTGTTGGTT<br>GGAGTATTTATTTGTTCTATCTGTGTGAAA<br>GGATCTTCCCAGCCCCAAGCAAGAGTTTAT<br>TTAACATTTGATGAACTTCGAGAAACCAAG<br>ACCTCTGAATACTTCAGCCTTTCCCACCAT<br>CCTTTAGACTACAGGATTTTATTAATGGAT<br>GAAGATCAGGACCGGATATATGTGGGAAG<br>CAAAGATCACATTCTTTCCCTGAATATTAA<br>CAATATAAGTCAAGAAGCTTTGAGTGTTTT<br>CTGGCCAGCATCTACAATCAAAGTTGAAG<br>AATGCAAAATGGCTGGCAAAGATCCCACA<br>CACGGCTGTGGGAACTTTGTCCGTGTAATT<br>CAGACTTTCAATCGCACACATTTGTATGTC<br>TGTGGGAGTGGCGCTTTCAGTCCTGTCTGT<br>ACTTACTTGAACAGAGGGAGGAGATCAGA<br>GGACCAAGTTTTCATGATTGACTCCAAGTG<br>TGAATCTGGAAAAGGACGCTGCTCTTTCAA<br>CCCCAACGTGAACACGGTGTCTGTTATGAT<br>CAATGAGGAGCTTTTCTCTGGAATGTATAT<br>AGATTTCATGGGGACAGATGCTGCTATTTT<br>TCGAAGTTTAACCAAGAGGAATGCGGTCA<br>GAACTGATCAACATAATTCCAAATGGCTAA<br>GTGAACCTATGTTTGTAGATGCACATGTCA<br>TCCCAGATGGTACTGATCCAAATGATGCTA<br>AGGTGTACTTCTTCTTCAAAGAAAAACTGA<br>CTGACAATAACAGGAGCACGAAACAGATT<br>CATTCCATGATTGCTCGAATATGTCCTAAT<br>GACACTGGTGGACTGCGTAGCCTTGTCAAC<br>AAGTGGACCACTTTCTTAAAGGCGAGGCTG<br>GTGTGCTCGGTAACAGATGAAGACGGCCC<br>AGAAACACACTTTGATGAATTAGAGGATG<br>TGTTTCTGCTGGAAACTGATAACCCGAGGA<br>CAACACTAGTGTATGGCATTTTTACAACAT<br>CAAGCTCAGTTTTCAAAGGATCAGCCGTGT<br>GTGTGTATCATTTATCTGATATACAGACTG<br>TGTTTAATGGGCCTTTTGCCCACAAAGAAG<br>GGCCCAATCATCAGCTGATTTCCTATCAGG<br>GCAGAATTCCATATCCTCGCCCTGGAACTT<br>GTCCAGGAGGAGCATTTACACCCAATATGC<br>GAACCACCAAGGAGTTCCCAGATGATGTT<br>GTCACTTTTATTCGGAACCATCCTCTCATGT<br>ACAATTCCATCTACCCAATCCACAAAAGGC<br>CTTTGATTGTTCGTATTGGCACTGACTACA<br>AGTATACAAAGATAGCTGTGGATCGAGTG<br>AACGCTGCTGATGGGAGATACCATGTCCTG<br>TTTCTCGGAACAGATCGGGTACTGTGCAA<br>AAAGTGGTTGTTCTTCCTACTAACAACTCT<br>GTCAGTGGCGAGCTCATTCTGGAGGAGCTG<br>GAAGTCTTTAAGAATCATGCTCCTATAACA<br>ACAATGAAAATTTCATCTAAAAAGCAACA<br>GTTGTATGTGAGTTCCAATGAAGGGGTITC<br>CCAGGTATCTCTGCACCGCTGCCACATCTA<br>TGGTACAGCCTGTGCTGACTGCTGCCTGGC<br>GCGGGACCCTTATTGCGCCTGGGATGGCCA<br>TTCCTGTTCCAGATTCTACCCAACTGGGAA<br>ACGGAAGAGCAAAAAACAAGATGTGAGAC |

-continued

Sequence Table

| SEQ ID # | Sequenct Identity | Sequence |
|---|---|---|
| | | ATGGAAACCCACTGACTCAATGCAGAGGA<br>TTTAATCTAAAAGCATACAGAAATGCAGCT<br>GAAATTGTGCAGTATGGAGTAAAAAATAA<br>CACCACTTTTCTGGAGTGTGCCCCCAAGTC<br>TCCGCAGGCATCTATCAAGTGGCTGTTACA<br>GAAAGACAAAGACAGGAGGAAAGAGGTT<br>AAGCTGAATGAACGAATAATAGCCACTTC<br>ACAGGGACTCCTGAICCGCICTGTTCAGGG<br>TTCTGACCAAGGACTTTATCACTGCATTGC<br>TACAGAAAATAGTTTCAAGCAGACCATAG<br>CCAAGATCAACTTCAAAGTTTTAGATTCAG<br>AAATGGTGGCTGTTGTGACGGACAAATGG<br>TCCCCATGGACCTGGGCCAGCTCTGTGAGG<br>GCTTTACCCTTCCACCCGAAGGACATCATG<br>GGGGCATTCAGCCACTCAGAAATGCAGAT<br>GATTAACCAATATTGCAAAGACACTCGGC<br>AGCAACATCAGCAGGGAGATGAATCACAG<br>AAAATGAGAGGGGACTATGGCAAGTTAAA<br>GGCCCTCATCAATAGTCTCGAGGACAAAA<br>CTCACACATGCCCACCGTGCCCAGCACCTG<br>AACTCCTGGGGGACCGTCAGTCTTCCTCT<br>TCCCCCCAAAACCCAAGGACACCCTCATGA<br>TCTCCCGGACCCCTGAGGTCACATGCGTGG<br>TGGTGGACGTGAGCCACGAAGACCCTGAG<br>GTCAAGTTCAACTGGTACGTGGACGGCGTG<br>GAGGTGCATAATGCCAAGACAAAGCCGCG<br>GGAGGAGCAGTACAACAGCACGTACCGTG<br>TGGTCAGCGTCCTCACCGTCCTGCACCAGG<br>ACTGGCTGAATGGCAAGGAGTACAAGTGC<br>AAGGTCTCCAACAAAGCCCTCCCAGCCCCC<br>ATCGAGAAAACCATCTCCAAAGCCAAAGG<br>GCAGCCCCGAGAACCACAGGTGTACACCC<br>TGCCCCCATCCCGGGAGGAGATGACCAAG<br>AACCAGGTCAGCCTGACCTGCCTGGTCAAA<br>GGCTTCTATCCCAGCGACATCGCCGTGGAG<br>TGGGAGAGCAATGGGCAGCCGGAGAACAA<br>CTACAAGACCACGCCTCCCGTGCTGGACTC<br>CGACGGCTCCTTCTTCCTCTATAGCAAGCT<br>CACCGTGGACAAGAGCAGGTGGCAGCAGG<br>GGAACGTCTTCTCATGCTCCGTGATGCATG<br>AGGCTCTGCACAACCACTACACGCAGAAG<br>AGCCTCTCCCTGTCCCCGGGTAAATGA |
| SEQ ID NO: 23 | cDNA sequence of UNCL-Sema3C-myc-6His (SEQ ID NO: 9) | ATGGCATTCCGGACAATTTGCGTGTTGGTT<br>GGAGTATTTATTTGTTCTATCTGTGTGAAA<br>GGATCTTCCCAGCCCCAAGCAAGAGTTTAT<br>TTAACATTTGATGAACTTCGAGAAACCAAG<br>ACCTCTGAATACTTCAGCCTTTCCCACCAT<br>CCTTTAGACTACAGGATTTTATTAATGGAT<br>GAAGATCAGGACCGGATATATGTGGGAAG<br>CAAAGATCACATTCTTTCCCTGAATATTAA<br>CAATATAAGTCAAGAAGCTTTGAGTGTTTT<br>CTGGCCAGCATCTACAATCAAAGTTGAAG<br>AATGCAAAATGGCTGGCAAAGATCCCACA<br>CACGGCTGTGGGAACTTTGTCCGTGTAATT<br>CAGACTTTCAATCGCACACATTTGTATGTC<br>TGTGGGAGTGGCGCTTTCAGTCCTGTCTGT<br>ACTTACTTGAACAGAGGGAGGAGATCAGA<br>GGACCAAGTTTTCATGATTGACTCCAAGTG<br>TGAATCTGGAAAAGGACGCTGCTCTTTCAA<br>CCCCAACGTGAACACGGTGTCTGTTATGAT<br>CAATGAGGAGCTTTTCTCTGGAATGTATAT<br>AGATTTCATGGGACAGATGCTGCTATTTT<br>TCGAAGTTTAACCAAGAGGAATGCGGTCA<br>GAACTGATCAACATAATTCCAAATGGCTAA<br>GTGAACCTATGTTTGTAGATGCACATGTCA<br>TCCCAGATGGTACTGATCCAAATGATGCTA<br>AGGTGTACTTCTTCTTCAAAGAAAAACTGA<br>CTGACAATAACAGGAGCACGAAACAGATT<br>CATTCCATGATTGCTCGAATATGTCCTAAT<br>GACACTGGTGGACTGCGTAGCCTTGTCAAC<br>AAGTGGACCACTTTCTTAAAGGCGAGGCTG<br>GTGTGCTCGGTAACAGATGAAGACGGCCC<br>AGAAACACACTTTGATGAATTAGAGGATG |

Sequence Table

| SEQ ID # | Sequenct Identity | Sequence |
|---|---|---|
| | | TGTTTCTGCTGGAAACTGATAACCCGAGGA<br>CAACACTAGTGTATGGCATTTTTACAACAT<br>CAAGCTCAGTTTTCAAAGGATCAGCCGTGT<br>GTGTGTATCATTTATCTGATATACAGACTG<br>TGTTTAATGGGCCTTTTGCCCACAAAGAAG<br>GGCCCAATCATCAGCTGATTTCCTATCAGG<br>GCAGAATTCCATATCCTCGCCCTGGAACTT<br>GTCCAGGAGGAGCATTTACACCCAATATGC<br>GAACCACCAAGGAGTTCCCAGATGATGTT<br>GTCACTTTTATTCGGAACCATCCTCTCATGT<br>ACAATTCCATCTACCCAATCCACAAAAGGC<br>CTTTGATTGTTCGTATTGGCACTGACTACA<br>AGTATACAAAGATAGCTGTGGATCGAGTG<br>AACGCTGCTGATGGGAGATACCATGTCCTG<br>TTTCTCGGAACAGATCGGGGTACTGTGCAA<br>AAAGTGGTTGTTCTTCCTACTAACAACTCT<br>GTCAGTGGCGAGCTCATTCTGGAGGAGCTG<br>GAAGTCTTTAAGAATCATGCTCCTATAACA<br>ACAATGAAAATTTCATCTAAAAAGCAACA<br>GTTGTATGTGAGTTCCAATGAAGGGGTTTC<br>CCAGGTATCTCTGCACCGCTGCCACATCTA<br>TGGTACAGCCTGTGCTGACTGCTGCCTGGC<br>GCGGGACCCTTATTGCGCCTGGGATGGCCA<br>TTCCTGTTCCAGATTCTACCCAACTGGGAA<br>ACGGAAGAGCAAAAAACAAGATGTGAGAC<br>ATGGAAACCCACTGACTCAATGCAGAGGA<br>TTTAATCTAAAAGCATACAGAAATGCAGCT<br>GAAATTGTGCAGTATGGAGTAAAAAATAA<br>CACCACTTTTCTGGAGTGTGCCCCCAAGTC<br>TCCGCAGGCATCTATCAAGTGGCTGTTACA<br>GAAAGACAAAGACAGGAGGAAAGAGGTT<br>AAGCTGAATGAACGAATAATAGCCACTTC<br>ACAGGGACTCCTGATCCGCTCTGTTCAGGG<br>TTCTGACCAAGGACTTTATCACTGCATTGC<br>TACAGAAAATAGTTTCAAGCAGACCATAG<br>CCAAGATCAACTTCAAAGTTTTAGATTCAG<br>AAATGGTGGCTGTTGTGACGGACAAATGG<br>TCCCCATGGACCTGGGCCAGCTCTGTGAGG<br>GCTTTACCCTTCCACCCGAAGGACATCATG<br>GGGGCATTCAGCCACTCAGAAATGCAGAT<br>GATTAACCAATATTGCAAAGACACTCGGC<br>AGCAACATCAGCAGGGAGATGAATCACAG<br>AAAATGAGAGGGGACTATGGCAAGTTAAA<br>GGCCCTCATCAATAGTCTCGAGTCTAGAGG<br>GCCCTTCGAACAAAAACTCATCTCAGAAG<br>AGGATCTGAATATGCATACCGGTCATCATC<br>ACCATCACCATTGA |
| SEQ ID NO: 24 | 5'-primer according to step 1 of Example 1 | GGGAAACGGAGGAGCAAAAGACAAGATGT<br>GAGACATGG |
| SEQ ID NO: 25 | 3'-primer according to step 1 of Example 1 | CCATGTCTCACATCTTGTCTTTTGCTCCTCC<br>GTTTCCC |
| SEQ ID NO: 26 | 5'-primer according to step 2 of Example 1 | TACCCAACTGGGAAACGGAAGAGCAAAAG<br>ACAAGATGTGAGACA TGG |
| SEQ ID NO: 27 | 3'-primer according to step 2 of Example 1 | CCATGTCTCACATCTTGTCTTTTGCTCTTCC<br>GTTTCCCAGTTGGGTA |
| SEQ ID NO: 28 | 5'-primer according to step 3 of Example 1 | GGGAAACGGAAGAGCAAAAACAAGATGT<br>GAGACATGGAAACCC |
| SEQ ID NO: 29 | 3'-primer according to step 3 of Example 1 | GGGTTTCCATGTCTCACATCTTGTTTTTTGC<br>TCTTCCGTTTCCC |

Sequence Table

| SEQ ID # | Sequenct Identity | Sequence |
|---|---|---|
| SEQ ID NO: 30 | 5'-primer for ligation to pGem T-easy according to Example 1 | CGGGATCCACCATGGCATCGGACAATTTG |
| SEQ ID NO: 31 | 3'-primer for ligation to pGem T-easy according to Example 1 | CGCTCGAGACTATTGATGAGGGCCTTTAACTT |
| SEQ ID NO: 32 | C-terminus of SEQ ID NO: 15 truncated in UNCL-Sema3C/FC | CGGAAAAGTAGAAACAGGAGGAATCAGTTGCCAGAGTCATAA |
| SEQ ID NO: 33 | Sema3C with a C-terminus truncation deleting FPPC cleavage site 3 | MAFRTICVLVGVFICSICVKGSSQPQARVYLTFDELRETKTSEYFSLSHHPLDYRILLMDEDQDRIYVGSKDHILSLNINNISQEALSVFWPASTIKVEECKMAGKDPTHGCGNFVRVIQTFNRTHLYVCGSGAFSPVCTYLNRGRRSEDQVFMIDSKCESGKGRCSFNPNVNTVSVMINEELFSGMYIDFMGTDAAIFRSLTKRNAVRTDQHNSKWLSEPMFVDAHVIPDGTDPNDAKVYFFFKEKLTDNNRSTKQIHSMIARICPNDTGGLRSLVNKWTTFLKARLVCSVTDEDGPETHFDELEDVFLLETDNPRTTLVYGIFTTSSSVFKGSAVCVYHLSDIQTVFNGPFAHKEGPNHQLISYQGRIPYPRPGTCPGGAFTPNMRTTKEFPDDVVTFIRNHPLMYNSIYPIHKRPLIVRIGTDYKYTKIAVDRVNAADGRYHVLFLGTDRGTVQKVVVLPTNNSVSGELILEELEVFKNHAPITTMKISSKKQQLYVSSNEGVSQVSLHRCHIYGTACADCCLARDPYCAWDGHSCSRFYPTGKRRSRRQDVRHGNPLTQCRGFNLKAYRNAAEIVQYGVKNNTTFLECAPKSPQASIKWLLQKDKDRRKEVKLNERIIATSQGLLIRSVQGSDQGLYHCIATENSFKQTIAKINFKVLDSEMVAVVTDKWSPWTWASSVRALPFHPKDIMGAFSHSEMQMINQYCKDTRQQHQQGDESQKMRGDYGKLKALINS |
| SEQ ID NO: 34 | C-terminus of SEQ ID NO: 1 truncated in UNCL-Sema3C/FC | RKSRNRRNQLPES |
| SEQ ID NO: 35 | Sema3C with a C-terminus truncation deleting FPPC cleavage site 3 and a modification of FPPC cleavage site 2 | MAFRTICVLVGVFICSICVKGSSQPQARVYLTFDELRETKTSEYFSLSHHPLDYRILLMDEDQDRIYVGSKDHILSLNINNISQEALSVFWPASTIKVEECKMAGKDPTHGCGNFVRVIQTFNRTHLYVCGSGAFSPVCTYLNRGRRSEDQVFMIDSKCESGKGRCSFNPNVNTVSVMINEELFSGMYIDFMGTDAAIFRSLTKRNAVRTDQHNSKWLSEPMFVDAHVIPDGTDPNDAKVYFFFKEKLTDNNRSTKQIHSMIARICPNDTGGLRSLVNKWTTFLKARLVCSVTDEDGPETHFDELEDVFLLETDNPRTTLVYGIFTTSSSVFKGSAVCVYHLSDIQTVFNGPFAHKEGPNHQLISYQGRIPYPRPGTCPGGAFTPNMRTTKEFPDDVVTFIRNHPLMYNSIYPIHKRPLIVRIGTDYKYTKIAVDRVNAADGRYHVLFLGTDRGTVQKVVVLPTNNSVSGELILEELEVFKNHAPITTMKISSKKQQLYVSSNEGVSQVSLHRCHIYGTACADCCLARDPYCAWDGHSCSRFYPTGKRKSKKQDVRHGNPLTQCRGFNLKAYRNAAEIVQYGVKNNTTFLECAPKSPQASIKWLLQKDKDRRKEVKLNERIIATSQGLLIRSVQGSDQGLYHCIATENSFKQTIAKINFKVLDSEMVAVVTDKWSPWTWASSVRALPFHPKDIMGAFSHSEMQMINQYCKDTRQQHQQGDESQKMRGDYGKLKALINS |

-continued

| Sequence Table | | |
|---|---|---|
| SEQ ID # | Sequenct Identity | Sequence |
| SEQ ID NO: 36 | C-terminus of SEQ ID NO: 1 from FPPC cleavage site 3 and downstream | RNRRNQLPES |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. It is to be understood that further trials are being conducted to establish clinical effects.

The invention claimed is:

1. A variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2.

2. The variant of claim 1, wherein said modification is a modification of at least one arginine residue within said furin-like pro-protein convertase cleavage site 2.

3. The variant of claim 1, wherein said modification is a modification of at least one arginine residue within said furin-like pro-protein convertase cleavage site to a lysine residue.

4. The variant of claim 1, wherein said variant further comprises at least one modification in a basic domain of said variant, the basic domain having an amino acid sequence as set forth in SEQ ID NO: 5.

5. The variant of claim 1, wherein said at least one modification in cleavage site 2 is a modification as set forth in SEQ ID NO: 13.

6. The variant of claim 4, wherein said at least one modification is a truncation of at least part of the C-terminus of said variant as set forth in SEQ ID NO: 34.

7. The variant of claim 5, wherein said variant further comprises a modification which is a truncation of at least part of the C-terminus of said variant as set forth in SEQ ID NO: 34.

8. The variant of claim 1, wherein said modification renders said variant resistant to cleavage at said cleavage site by members of the furin-like pro-protein convertases.

9. A complex comprising the variant of claim 1 and non-proteinaceous or proteinaceous moiety.

10. The complex of claim 9, wherein the non proteinaceous moiety is polyethylene glycol (PEG) or derivative thereof, polyvinyl pyrrolidone (PVP), divinyl ether, maleic anhydride copolymer (DIVEMA), polysialic acid (PSA), poly(styrene comaleic anhydride) (SMA), hyaluronic acid (HA), alginic acid (AA), polyhydroxyethyl methacrylate (Poly-HEMA), glyme or polyisopropylacrylamide or any combination thereof.

11. The complex of claim 10, wherein the proteinaceous moiety is a peptide, polypeptide or an immunoglobulin or a part thereof.

12. The complex of claim 11, wherein the immunoglobulin is Fc region.

13. A pharmaceutical composition comprising at least one of the variants of claim 1.

14. A pharmaceutical composition comprising the amino acid sequence as set forth in SEQ ID NO: 8.

15. A method for treating cancer in a subject in need thereof, the method comprising administering a pharmaceutical composition according claim 13 to said subject.

16. The method of claim 15, wherein treating is selected from the group consisting of: suppressing growth of a tumor, reducing occurrence of metastases and a combination thereof.

17. The method of claim 15, wherein said cancer is selected from the group consisting of: lymphoma, breast cancer, head and neck cancer, squamous carcinomas of the head and neck (HNSCC), lung cancer, rectal cancer, bile duct cancer, bladder cancer, bone cancer, colon cancer, brain cancer, cervical cancer, ocular melanoma, Kaposi's sarcoma, leukemia, melanoma, myeloma, ovarian cancer, vaginal cancer, prostate cancer, testicular cancer, endometrial cancer, thyroid cancer and thymus cancer.

18. The method of claim 17, wherein said cancer is breast cancer.

19. The method of claim 16, wherein said metastases are metastases in lymph nodes of said subject.

20. The method of claim 13, wherein administration to said subject is by a route selected from the group consisting of: intravenous, intraarterial, transdermal, subcutaneous, via direct injection into a tissue and via direct injection into a tumor.

21. A pharmaceutical composition, the composition comprising as an active ingredient a therapeutically effective amount of wild-type Semaphorin 3C as set forth in SEQ ID NO: 1 or has at least 80%, 90%, 95%, or 99% sequence identity with the amino acid set forth in SEQ ID NO: 1.

22. A method for inhibiting lymphangiogenesis in a subject, the method comprising administering a pharmaceutical composition according claim 13 to said subject.

23. A method for inhibiting lymphangiogenesis in a subject, the method comprising administering a pharmaceutical composition according claim 21 to said subject.

24. A method for inhibiting angiogenesis in a subject, the method comprising administering a pharmaceutical composition according claim 13 to said subject.

25. A method for inhibiting angiogenesis in a subject, the method comprising administering a pharmaceutical composition according claim 21 to said subject.

* * * * *